US011162119B2

(12) United States Patent
Nielsen et al.

(10) Patent No.: US 11,162,119 B2
(45) **Date of Patent: *Nov. 2, 2021**

(54) METHODS AND PRODUCTS FOR PRODUCTION OF WAX ESTERS

(71) Applicant: Melt & Marble AB, Gothenburg (SE)

(72) Inventors: Jens Nielsen, Gothenburg (SE); Shuobo Shi, Gothenburg (SE)

(73) Assignee: Melt & Marble AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,399

(22) Filed: Dec. 18, 2019

(65) Prior Publication Data

US 2020/0231997 A1 Jul. 23, 2020

Related U.S. Application Data

(63) Continuation of application No. 15/927,483, filed on Mar. 21, 2018, now Pat. No. 10,533,198, which is a continuation of application No. 13/814,694, filed as application No. PCT/EP2011/063542 on Aug. 5, 2011, now abandoned.

(60) Provisional application No. 61/401,026, filed on Aug. 6, 2010.

(51) Int. Cl.

| | |
|---|---|
| ***C12N 1/18*** | (2006.01) |
| ***C12N 9/16*** | (2006.01) |
| ***C12N 9/10*** | (2006.01) |
| ***C12P 7/64*** | (2006.01) |
| ***C12N 15/81*** | (2006.01) |

(52) U.S. Cl.

CPC ............ *C12P 7/649* (2013.01); *C12N 9/1029* (2013.01); *C12N 15/81* (2013.01); *C12Y 602/01001* (2013.01); *Y02E 50/10* (2013.01)

(58) Field of Classification Search

CPC ...... C12N 15/815; C12N 9/0042; C12N 9/16; C12Y 602/01001; C12P 7/6472

USPC ............ 435/254.2, 254.22, 254.21, 134, 142

See application file for complete search history.

(56) References Cited

U.S. PATENT DOCUMENTS

| | | | |
|---|---|---|---|
| 2006/0051847 | A1 | 3/2006 | Gunnarsson |
| 2009/0117629 | A1 | 5/2009 | Schmidt-Dannert et al. |
| 2013/0197248 | A1 | 8/2013 | Nielsen et al. |

FOREIGN PATENT DOCUMENTS

| | | |
|---|---|---|
| CA | 2650773 | 11/2007 |
| WO | WO 03/074676 | 9/2003 |
| WO | WO 05/118814 | 12/2005 |
| WO | WO 08/119082 | 10/2008 |
| WO | WO 11/157848 | 12/2011 |

OTHER PUBLICATIONS

Beopoulos et al. "Yarrowía lipolytica: A model and a tool to understand the mechanisms implicated in lipid accumulation", Biochimie, 91:692-696 (2009).

C Espaux et al. "Engineering high-level production of fatty alcohols by *Saccharomyces cerevisiae* from lignocellulosic feedstocks", (Metab. Eng. 42:115-125 (2017).

Devos, D. et al. Practical Limits of Function Prediction, *Proteins: Structure, Function and Genetics*. 41:98-107 (2000).

Gustafsson, C. et al. "Codon bias and heterologous protein expression", *Trends in Biotechnology*, Jul. 2004, vol. 22, No. 7, pp. 346-353, Abstract.

International Search Report and Written Opinion Corresponding to International Application No. PCT/EP2011/083542: dated Feb. 6, 2013: 13 Pages.

Kalscheuer, R. "Microdiesel: *Escherichia coli* engineered for fuel production", *Society for General Microbiology*. Jan. 2006, pp. 2529-2536.

Kalscheuer, Rainer "Synthesis of Novel Lipids in *Saccharomyces cerevisiae* by Heterologous Expression of an Unspecific Bacterial Acyltransferase" *Applied Environmental Microbiology*, Dec. 2004, pp. 7119-7125.

Kisselev L., "Polypeptide Release Factors in Prokaryotes and Eukaryotes: Same Function Different Structure", *Structure*, 10:8-9, (2002).

Lanfranconi, Mariana "Indentification of genes coding for putative wax ester synthase/diacylglycerol acyltransferase enzymes in terrestrial and marine environments" *AMB Express, a SpringerOpen Journal*, Jul. 2015, 13 pages.

Li, Fengling, "Identification of the wax ester sythase/acyl-coenzyme A: diacylglycerol acyltransferase WSD1 required for stem wax ester biosynthesis in *Arabidopsis*", *Plant Physiology*, Sep. 2008, vol. 148, pp. 97-107.

Mandrup, Susanne, et al. "Effect of heterologous expression of acyl-CoA-binding protein on acyl-CoA level and composition in yeast", *Biochem*, J. (1993) pp. 369-374.

Michell, Belinda et al. "Isoform-Specific Purification and Substrate Specificity of the 5'-AMP-activated Protein Kinase", *The Journal of Biological Chemistry*, 271.28445-28450 (1996).

(Continued)

*Primary Examiner* — Robert B Mondesi
*Assistant Examiner* — Mohammad Y Meah
(74) *Attorney, Agent, or Firm* — Myers Bigel, P.A.

(57) ABSTRACT

The present invention relates to the provision of genetically modified fungal cells, such as yeast cells with an improved ability for producing different fatty acids and specifically fatty acid ethyl esters (FAEE), the main components of biodiesel. An increased in fatty acid production, and hence in FAEE, is obtained in the first place by expressing different heterologous polypeptides in combination with the down-regulation, attenuation, deletion or over-expression of specially selected genes, wherein said genes encode enzymes involved in the fatty acids synthesizing pathway, fatty acid consuming pathways, carbohydrate biosynthesis pathways or enzyme acting as wax ester transporters or a combination thereof. The methods and products of the invention would allow large-scale production of FAEE with carbohydrates as the only externally-supplied substrate.

8 Claims, 17 Drawing Sheets

Specification includes a Sequence Listing.

(56) References Cited

OTHER PUBLICATIONS

Saerens, Sofie et al. "The *Saccharomyces cerevisiae*EHT1 and EEB1 Genes Encode Novel Enzymes with Medium-chain Fatty Acid Ethyl Ester Synthesis and Hydrolysis Capacity", *The Journal of Biological Chemistry*, 281:4446-4455 (2006).

Sorgei, D. "A Yeast Strain Lacking Lipid Particles Bears a Defect in Ergosterol Formation", *Journal of Biological Chemistry*, Jan. 2004, vol. 279, No. 30, 7 pages.

Trotter, Pamela, "The Genetics of Fatty Acid Metabolism in *Saccharomyces cerevisiae*", *Annual Review of Nutrition*, Jan. 2001, pp. 97-119.

Villa, Juan "Use of Limited Proteolysis and Mutagenesis To Identify Folding Domains and Sequence Motifs Critical for Wax Ester Synthase/Acyl Coenzyme A Diacyiglycerol Acyltransferase Activity" *Applied and Environmental Microbiology*, Feb. 2014, vol. 80, No. 3, 10 pages.

Waltermann, Marc "Key enzymes for biosynthesis of neutral lipid storage compounds in prokaryotes: Properties, function and occurrence of wax ester synthases/acyl-CoA:diacylglycerol acyltransferases" *Biochimie* vol. 89 (2007) pp. 230-242.

Whisstock, James et al., "Prediction of protein function from protein sequence and structure", *Quarterly Reviews of Biophysics*, 36:307-340 (2003).

Witkowski, A. et al. "Conversion of β-Ketoacyl Synthase to a Malonyl Decarboxylase by Replacement of the Active-Site Cysteine with Glutamine", *Biochemistry*, 38:11643-11650.

Zhou, Y. et al. "Production of fatty acid-derived oleochemicals and biofuels by synthetic yeast cell factories", Nat. Comm., 25(7):11709 (2016).

METHODS AND PRODUCTS FOR PRODUCTION OF WAX ESTERS

STATEMENT OF PRIORITY

This application is a continuation application and claims priority to U.S. patent application Ser. No. 15/927,483, filed Mar. 21, 2018, which is a continuation application of U.S. patent application Ser. No. 13/814,694, filed Apr. 19, 2013, which is a 35 U.S.C. § 371 national phase application of International Application Serial No. PCT/EP2011/063542, filed Aug. 5, 2011, which claims the benefit, under 35 U.S.C. § 119 (a) of U.S. Provisional Patent Application Ser. No. 61/401,026, filed Aug. 6, 2010, the entire contents of each of which are incorporated by reference herein.

FIELD OF THE INVENTION

The present invention relates to the development of genetically engineered microorganisms that can produce wax esters in a controllable and economic fashion. More specifically the invention relates to the production of liquid wax esters that can be used for biofuel, lubricants, cosmetics, linoleum, printing inks as well as products related thereto, and for the production of solid wax esters used for candles and polishes as well as products related thereto.

DESCRIPTION OF THE RELATED ART

Fossil fuels, such as coal, oil, and natural gas, have been powering modem society for more than one century. However, fresh discoveries of deposits are on the wane and demands are increasing. The world's demand of fossil fuels will soon outweigh the current supply. An innovative approach offering some solution comes from the biotechnology industries. Efforts have made biodiesel as one of the most thoroughly developed and promising alternative fuels on the market. It works well in conventional diesel engines, with less hazardous emissions, and is consumed at greater than 3.5 billion gallons per year.

Biodiesel is generally composed of fatty acid methyl esters (FAMEs) or fatty acid ethyl esters (FAEE), and is mostly derived from vegetable oil or animal fat by chemically transesterification with methanol or ethanol. Despite the fact that ethanol-yielded FAEEs have better performances, for cost reasons methanol is the reagent most frequently used for triglyceride transesterification. The current process has several drawbacks, including energy intensiveness, consuming edible feedstocks, difficulty of removal of the catalyst from the product and treatment of toxic waste-water, as well as geographical and seasonal restrictions.

To overcome the problems related to the use of catalysts people have been exploring new alternatives such as enzymatic conversion using lipases (EC 3.1.1.3, triacylglycerol hydrolases). Lipases can break down neutral lipids such as triglycerides and perform a transesterification reaction in a solvent system (i.e. tert-butanol). Enzymatic production of biodiesel can be carried out at moderate reaction conditions and at a lower alcohol to oil ratio. The main drawbacks with this kind of enzymatic catalysis are the strong inactivation effect caused by alcohols (i.e. methanol) and the high enzyme costs.

Both chemical and enzymatic transesterification require the use of toxic, petrochemically-derived alcohols and expensive feedstocks. Thus, transesterification-based biodiesel becomes unsustainable when fossil fuel derived products are used. As a result, the current feedstocks for biodiesel are mainly derived from plant oils like rapeseed oil.

However such plant oils are inherently limited by supply of water and land, and subsequently, they cannot produce enough biofuel without threatening food supplies and/or native biodiversity. Algae are a promising choice as an alternative feedstock. Nevertheless, there are problems with surface usage and oil extraction from algae based production. Everyone agrees that fuels derived from biomass are one of the best alternatives to fossil fuels. Thus, genetically manipulation of microorganisms to produce fatty acid esters, will substantially contribute to produce environmentally friendlier, sustainable, and cost-effective biodiesels.

In this regard, it was previously shown that an engineered *E. coli* strain expressing the wax synthase (WS) from *Acinetobacter baylyi* ADP1 and ethanol-production genes from *Z. mobilis*, could produce fatty acid ethyl esters by esterifying exogenously added fatty acids (Kalscheuer, Stolting et al. 2006). The research is an excellent demonstration of feasibility for microbial production of fatty acid esters. Recently, researchers from the Keasling group and the company LS9 Inc. (South San Francisco, USA) developed this idea further by constructing an engineered *E. coli* that can produce fatty-acid-derived fuels and chemicals from simple sugars and plant-derived biomass, without the need for fatty acid feeding (Steen, Kang et al. 2010). Production of fatty acid derivatives as biofuels has also been reported in recent patent applications WO2009/009391, WO2007136762 and WO2008119082, all owned by LS9 Inc. Briefly, the metabolically engineered *E. coli* strain was manipulated to be able to produce fatty (acid) esters and derivatives thereof (short and long chain alcohols, hydrocarbons, fatty alcohols, waxes, etc.) through the introduction of several genes encoding for enzymes such as thioesterase, wax synthase, alcohol acyltransferase, alcohol dehydrogenase, and different kinds of fatty alcohol forming acyl-CoA reductases. In U.S. patent publication 2010/0071259, inventors from the same company teach that by adding a mixture of at least two different alcohols to a medium containing the engineered *E. coli* strain that produces fatty esters, at least two different fatty esters could be produced.

The afore-mentioned biodiesel producing methods are all based on the use of the bacterium *E. coli*. However, *E. coli* is unable to naturally overproduce the two substrates of biodiesel, fatty acids and alcohol (i.e. ethanol), and this organism is not suitable for large-scale production that often involves harsh environmental conditions. Furthermore, *E. coli* is sensitive to phage contamination often resulting in substantial economic losses. The patents of the prior art successfully teach several strategies to enhance fatty acids biosynthesis in *E. coli*. Nevertheless, and apart from the drawbacks associated with the use of this host, it should be noted that strategies working in *E. coli* might not be appropriate when applied in other microorganisms.

A far better choice of microbial cell factory for industrial production of biodiesel would be the yeast *Saccharomyces cerevisiae*. This yeast is already widely used in industry, including for large-scale bioethanol production, but also for a range of specialty chemicals. The development of *S. cerevisiae* as a cell factory for biodiesel production would represent a major contribution as this could represent a plug and play solution where current infrastructures used for production of bioethanol could be used for production of far more valuable biodiesels. In contrast to the insufficient ethanol productivity of *E. coli, S. cerevisiae* is already a good ethanol producer.

In fact, production of FAEEs and fatty acid isoamyl esters (FAIEs) has been achieved in recombinant *S. cerevisiae* with oleic acid addition by expressing the *A. baylyi* bifunctional WS/DGAT enzyme (Kalscheuer, Luftmann et al. 2004). A recent patent application, namely US patent application 2009/0117629 by Schmidt-dannert and Holtzapple, also describes a method for the production of esters, including isoprenoid wax esters and fatty acid alkyl esters, such as FAME and FAEE, by heterologous expression of *Marinobacter hydrocarbonoclasticus* wax synthase (WS2) in *S. cerevisiae*. The invention is however, limited to the use of specific isolated polynucleotides from *Marinobacter hydrocarbonoclasticus*, and its application in e.g. producing biodiesel). Moreover this method requires exogenous supply of fatty acids as the endogeneous production of fatty acids by yeast is too low to ensure economically viable production of FAEEs.

A modified strain carrying the genes encoding the wax synthase from *Marinobacter hydrocarbonoclasticus* could be considered a potential host for biodiesel production in yeasts. Nonetheless, while this product is very suitable for the particular purpose it addresses, it is not the ideal option when the synthesis of other esters is desired. The knowledge of the preferred substrates for each wax synthase allows the use of yeast cells in applications other than biodiesel production. Moreover there is still a need for methods and products allowing large-scale production of fatty acid esters.

Thus it is an object of the present invention to provide an improved fungal cell factory, such as a yeast cell factory that can be used for fermentation based production of FAEEs, that is not dependent on the addition of exogenous fatty acids to the yeast culture and that possess an increased flux towards fatty acid biosynthesis and where high level production of FAEEs is obtained.

SUMMARY OF THE INVENTION

The above presented problems have now been solved by providing a fungal cell system for producing fatty acyl ethyl esters (FAEE), said system comprising a fungal cell and an expression vector encoding at least one wax synthase, wherein the metabolism of said fungal cell is additionally modified, said modification providing for down-regulation, attenuation, deletion and/or over-expression of one or more gene(s) selected from the group consisting of genes encoding one or more enzyme(s) involved in at least one of said fungal cell's fatty acid synthesizing pathways, fatty acid consuming pathways and carbohydrate biosynthesis pathways, and/or selected from the group consisting of genes encoding one or more enzyme(s) acting as wax ester transporter(s) of said fungal cell. Such a fungal cell system provides for an increased flux towards fatty acid biosynthesis and thereby a high level production of FAEEs. Examples of fungal cells applicable to the present invention can be selected from *Saccharomyces, Saccharomyces cerevisae Hansenula polymorpha, Kluyveromyces, Pichia, Candida albicans, Aspergilli, Rhodotorula rubra, Torulopsis, Trichosporon cutaneum, Trichoderma reesei, Apiofrichum curvafum, Yarrowia lipolytica*, and *Cryptococcus curvatus*.

Accordingly, a primary object of the present invention is to provide an advance in the microorganism fermentation method for producing wax esters, which include, but is not limited to, the liquid waxes used for biofuel, lubricants, cosmetics, linoleum and printing inks, and the solid waxes used for candles, polishes etc. The fungal cell system and the method disclosed herein combine the expression of different wax syntheses with metabolic engineering modifications to ensure a high flux to biosynthesize wax esters. The high flux described herein means at least 2-fold increase in the fatty acids flux compared with flux towards fatty acids in the reference yeast.

In one embodiment, the invention disclosure provides different nucleotide sequences encoding the polypeptides having wax synthase activity with differences in specificity towards different-chain-length substrates. Examples of different wax syntheses applicable within the scope of the present invention are *Mycobacterium, Rhodococcus, Acinetobacter, Mus Musculus* and/or *Marinobacter*, such as *Acinetobacter baylyi* ADP1, *Marinobacter hydrocarbonoclasticus* DSM 8798, *Rhodococcus opacus* PD630, *Mus musculus* C57BL/6, and *Psychrobacter articus* 273-4.

In another embodiment, the present invention provides a wax ester composition in the different production hosts expressing different wax synthases, wherein the wax ester with preferred carbon chain length could be produced according to the method disclosed herein.

Accordingly, the present invention also relates to a method for producing FAEE, said method comprising providing a fungal cell system as defined herein in a culture broth, adding one or more sources of carbohydrates as an external substrate to said fungal system, and wherein said FAEE are thereafter retrieved by extraction from said culture broth.

In particular implementations, the produced wax ester includes fatty acid ethyl esters that can be used as biofuels. In such an example, the only externally supplied substrates are carbohydrates, which can be transformed into ethanol and fatty acids, which can then be combined into esters.

In yet another embodiment, the invention provides a method of overproducing fatty acids. The microorganism can have ACBP (acyl-CoA-binding protein) over-expressed to deregulate the activity of enzymes involved in lipid metabolism (e.g., acetyl-CoA carboxylase).

In a further embodiment, the invention disclosure provides a method to overproduce fatty acids, in addition to over-expressing ACBP. The ACBP over-expressing microorganism can have one or more pathway modified, e.g., fatty acids synthesizing pathway, fatty acids consuming pathways, wax ester transporters, and engineering of the central carbon metabolism.

In a preferred embodiment the present invention provides a *Saccharomyces cerevisae* yeast cell with increased metabolic flux towards fatty acid ester biosynthesis. This in-house developed host cell expresses at least one (*Acinetobacter baylyi* ADP1, *Marinobacter hydrocarbonoclasticus* DSM 8798, *Rhodococcus opacus* PD630, *Mus musculus* C57BL/6 or *Psychrobacter articus* 273-4) specifically selected wax synthase in combination with an over-expressed ACBP.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

DETAILED DESCRIPTION OF THE INVENTION AND PREFERRED EMBODIMENTS THEREOF

Figure 1:
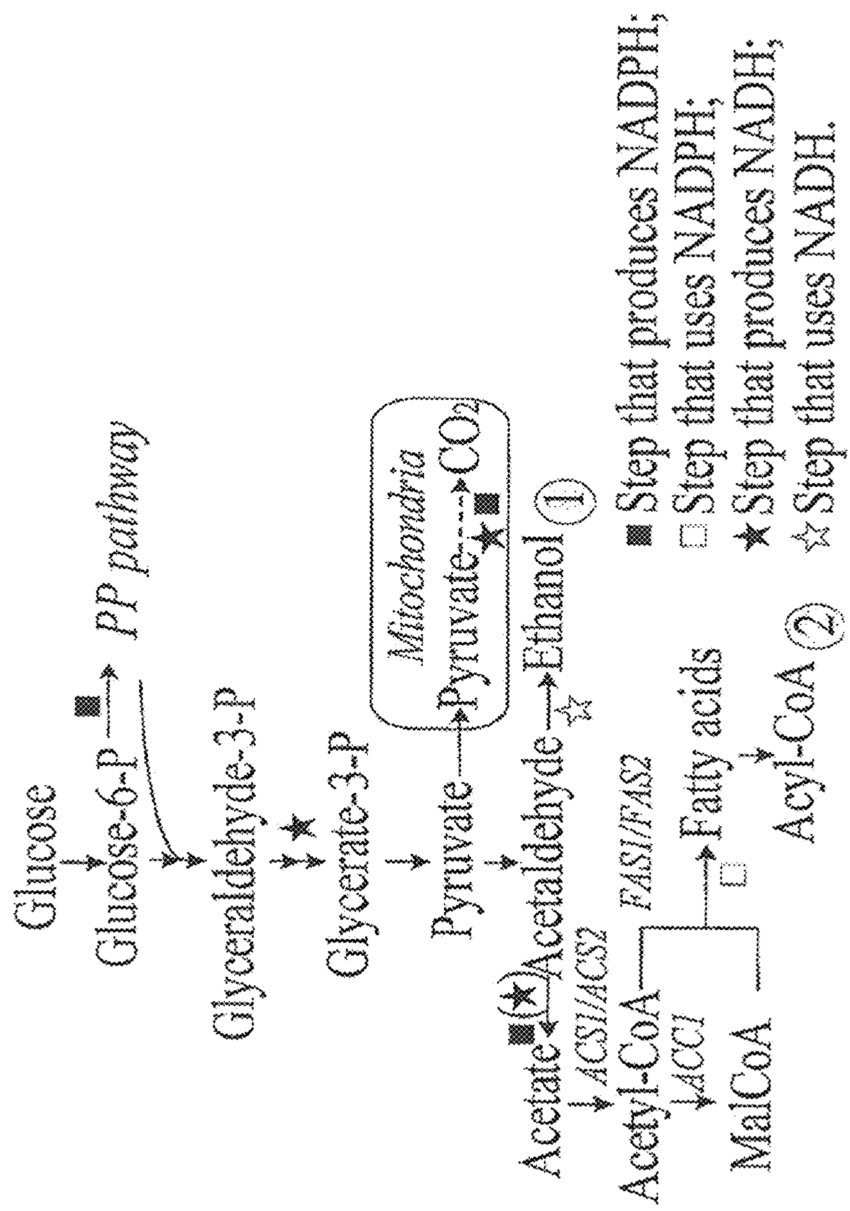
FIG. 1 shows the glycolysis pathway in yeast *Saccharomyces cerevisiae* for producing two direct precursor substrates (ethanol and acyl-CoA) of wax synthase. The glucose, via glycolysis, could be converted to ethanol (1), and acyl-CoA (2), the precursor for fatty acids.

The invention herein relies, unless otherwise indicated, on the use of conventional techniques of biochemistry, molecular biology, microbiology, cell biology, genomics and recombinant technology.

To facilitate understanding of the invention, a number of terms are defined below. The term "recombinant" means that a particular nucleic acid (DNA or RNA) is the product of various combinations of cloning, restriction, and/or ligation steps resulting in a construct having a structural coding or non-coding sequence distinguishable from endogenous nucleic acids found in natural systems The term "overproducing" is used herein in reference to the production of FAEE in a host cell and indicates that the host cell is producing more of the FAEE by virtue of the introduction of nucleic acid sequences encoding different polypeptides involved in the host cell's metabolic pathways or as a result of other modifications as compared with the wild-type or unmodified host cell.

As used herein, the terms "protein" and "polypeptide" refer to compounds comprising amino acids joined via peptide bonds and are used interchangeably.

As used herein, an "ACBP or acyl-CoA-binding protein" is a small (10 Kd) protein that binds medium- and long-chain acyl-CoA esters with very high affinity and may function as an intracellular carrier of acyl-CoA esters. The majority of the cellular long-chain acyl-CoA esters are presumed to be sequestered with acyl-CoA binding protein (ACBP).

Although ACBP occurs as a completely independent protein, intact ACB domains have been identified in a number of large, multifunctional proteins in a variety of eukaryotic species ranging from yeasts and plants to reptiles and mammals. In general ACBP is highly conserved in all eukaryotes. The yeasts homologue of ACBP is known as Acb1p. As used herein, an "Acetyl CoA carboxylase" is a biotin-containing enzyme that catalyzes the irreversible reaction in which acetyl-CoA is carboxylated to malonyl-CoA, see FIGS. 1 and 8, which is the precursor of long-chain fatty acyl-CoA. In mammals, two main isoforms of ACC are expressed, ACC1 and ACC2, which differ in both tissue distribution and function. ACC1 is found in the cytoplasm of all cells and encodes acetyl CoA carboxylase in yeast cells.

As used herein, FAS or a "fatty acid synthases" is an enzymatic system that catalyzes the initiation and elongation of acyl chains and thus plays a key role in fatty acid synthesis from acetyl-CoA and malonyl-CoA. Examples of these enzymes are AccABCD, FabD, FabH, FabG, FabA, FabZ, FabI, FabK, FabL, FabM, FabB, and FabF. In the yeast *Saccharomyces cerevisae*, fatty acids are synthesized by a 2.4 Mba multifunctional enzyme complex with two subunits encoded by two unlinked genes FAS1 and FAS 2.

As used herein, acyl-CoA synthase includes peptides in enzyme classification number EC 2.3.1.86, and are any of various ligases that catalyze the conversion of a fatty acid to acyl-CoA for subsequent 1-oxidation.

As used herein, "glyceraldehyde-3-phosphate dehydrogenase" (GAPDH) catalyzes the reversible interconversion between 1,3-bisphosphoglycerate and d-glyceraldehyde 3-phosphate using either NAD(H) or NADP(H) as a coenzyme. This is the sixth step of the glycolysis (FIG. 1) and thus serves to break down glucose for energy and carbon molecules.

NADPH, a product of the pentose phosphate pathway, functions as a reductant in various synthetic (anabolic) pathways including fatty acid synthesis.

As used herein, an "acetyl-coenzyme A synthetase" is an enzyme that catalyzes the formation of a new chemical bond between acetate and coenzyme A (CoA), which is a key branching molecule for different metabolic pathways.

Figure 2:
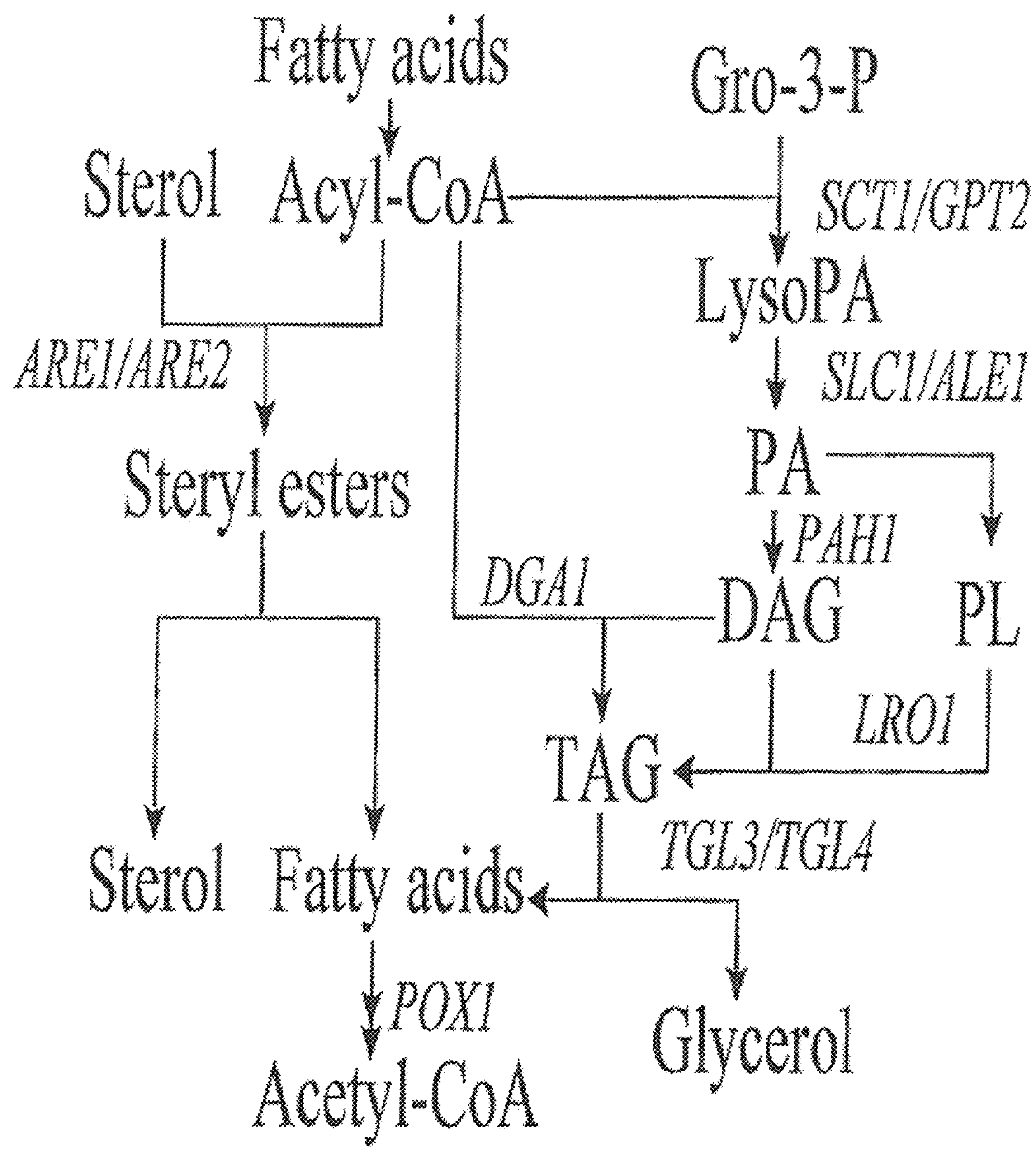
FIG. 2 shows the different reactions of the fatty acids consuming pathways.
Figure 3:
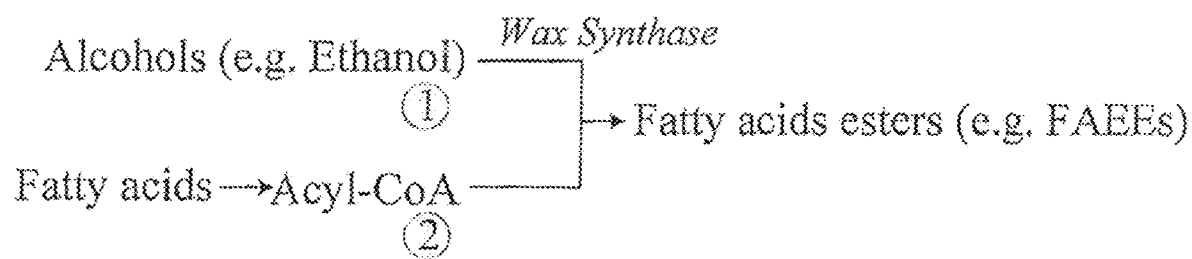
FIG. 3 shows a wax ester (e.g. FAEEs) biosynthesis pathway catalyzed by heterologous wax synthase in *Saccharomyces cerevisiae*. The alcohols could be biosynthesized by the production host or heterologous supplemented. The acyl-CoA could be produced via fatty acids biosynthesis by a production host or supplemented heterologously.

As used herein, "β-oxidation" is the process by which fatty acids in the form of Acyl-CoA molecules are broken down to generate Acetyl-CoA. It is the principal metabolic pathway responsible for the degradation of fatty acids (FIG. 2).

As used herein a "catalytic motif" is a three-dimensional structural unit formed by a particular sequence of amino acids, found in proteins and which is often linked with a particular function. For nucleic acids is a particular, usually short, nucleotide sequence that forms a recognition site usually, to which other proteins bind.

A peptide of the present invention may be present in an expression vector. The term "expression vector" is defined herein as a linear or circular DNA molecule that comprises a polynucleotide encoding a polypeptide of the invention, and which is operably linked to additional nucleotides that ensure its expression. Suitable expression vectors include fungal, baculovirus vectors, bacteriophage vectors, plasmids, phagemids, cosmids, fosmids, *Acinetobacter baylyi*, yeast plasmids and any other vectors specific for the hosts of interest. Vectors may be introduced into a host cell using methods that are known in the art such as, calcium phosphate precipitation, electroporation, heat shock, lipofection, microinjection, etc.

A "fungal cell system" as disclosed herein comprises a fungal cell which has been modified, such as genetically modified, as described herein, and which expresses at least one wax synthase, as exemplified herein. Said wax synthase is introduced into said fungal cell to provide for expression thereof in said fungal cell. The fungal cell system according to the invention hence provides the combination of a modified fungal cell and the expression of a wax synthase in said fungal cell, which allows for an increased metabolic flux towards fatty acid ester biosynthesis in said fungal cell. This advantageous combination is herein referred to as the "fungal cell system".

As used herein pESC vectors are a series of epitope-tagging vectors designed for expression and functional analysis of eukaryotic genes in the yeast *S. cerevisiae*. These vectors contain the GAL1 and GAL10 yeast promoters in opposing orientation. With these vectors one or two cloned genes can be introduced into a yeast host strain under the control of a repressible promoter Preferably the expression vector of the present invention is a pESC-derived plasmid in which the original promoter have been replaced. (S. Partow et al. 2010)

As used herein a "promoter" is a DNA sequence that usually precedes a gene in a DNA polymer and provides a site for initiation of the transcription into mRNA. In the present invention we used promoters derived from transcriptional Enhancer Factor 1 (TEF1) and phosphoglycerate kinase (PGK1). (S. Partow et al. 2010).

As used herein, sequence identity refers to sequence similarity between two nucleotide sequence or two peptide or protein sequences. The similarity is determined by sequence alignment to determine the functional, structural, and/or evolutionary relationships between the sequences. Gaps in either or both sequences are permitted in making successive alignment.

By two nucleotide sequence or two peptide or protein sequences having an amino acid sequence at least, for example 95% identical to a reference amino acid sequence, is intended that the amino acid sequence of e.g. the peptides is identical to the reference sequence, except that the amino acid sequence may include up to 5 point mutations per each 100 amino acids of the reference amino acid sequence. In other words, to obtain a peptide having an amino acid sequence at least 95% identical to a reference amino acid sequence: up to 5% of the amino acids in the reference sequence may be deleted or substituted with another amino acid, or a number of amino acids up to 5% of the total amino acids in the reference sequence may be inserted into the reference sequence.

These mutations of the reference sequence may occur at the amino and/or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

Fatty Acids' Synthesizing Pathway

The fatty acids synthesizing pathway includes fatty acid synthase enzymes selected from the group consisting of ACC1 (encoding acetyl-CoA carboxylase), FAS1/FAS 2 (encoding fatty acid synthase), and ACS1 (acetyl coenzyme A synthase) from any species to encode such proteins.

Fatty acids (FA) play an important role as building blocks of biodiesel. In *S. cerevisiae*, FA is mainly synthesized in cytosol and limits biodiesel production. A fatty acid over-producing yeast cell will in turn overproduce fatty acids derived esters, e.g. FAEES (biodiesel). In this embodiment the inventors herein improve the supply of FAEE precursors. Thus an over-expression of the gene coding to acetyl-CoA carboxylase (ACC1) in combination with an increased expression of fatty acid synthetases (FAS1 and FAS 2) yields an increased amount of Malonyl CoA and Fatty Acids, respectively.

The sources of malonyl-CoA, are generally supposed to be limited, impeding its utility for overproducing FA. The activity of acetyl-CoA carboxylase is highly regulated in *S. cerevisiae*: (1) Transcription of ACC1 is repressed by inositol and choline, as UASINO site was found in the promoter of ACC1 (Chirala, Zhong et al. 1994); (2) Acetyl-CoA carboxylase activity could be directly inactivated by Snf1p through phosphorylating (Shirra, Patton-Vogt et al. 2001).

For releasing the tight regulation of the ACC1 at the mRNA and protein level, the promoter of ACC1 is replaced. Furthermore, the inventors herein have found that under control of the constitutively expressed promoter, a release of ACC1 phosphorylation sites would provide a further increase towards FAEE biosynthetic flux. For example Ser659Ala and Ser1157Ala could be substituted (SEQ ID NO 16). Thus the inactivation by Snf1 could be avoided. The resulting strain with hyperactive Acc1p would enhance the FA biosynthesis significantly.

As previously stated, in addition to up-regulated activity of acetyl-CoA carboxylase, fatty acid synthase (FAS) could be over-activated to reinforce the push of hyperactive acetyl-CoA carboxylase. Therefore, FASI and FAS2 would be over-expressed in the engineered strain with hyperactive Acc1p. The combined manipulations would lead a high flux towards fatty acids biosynthesis.

Figure 8:
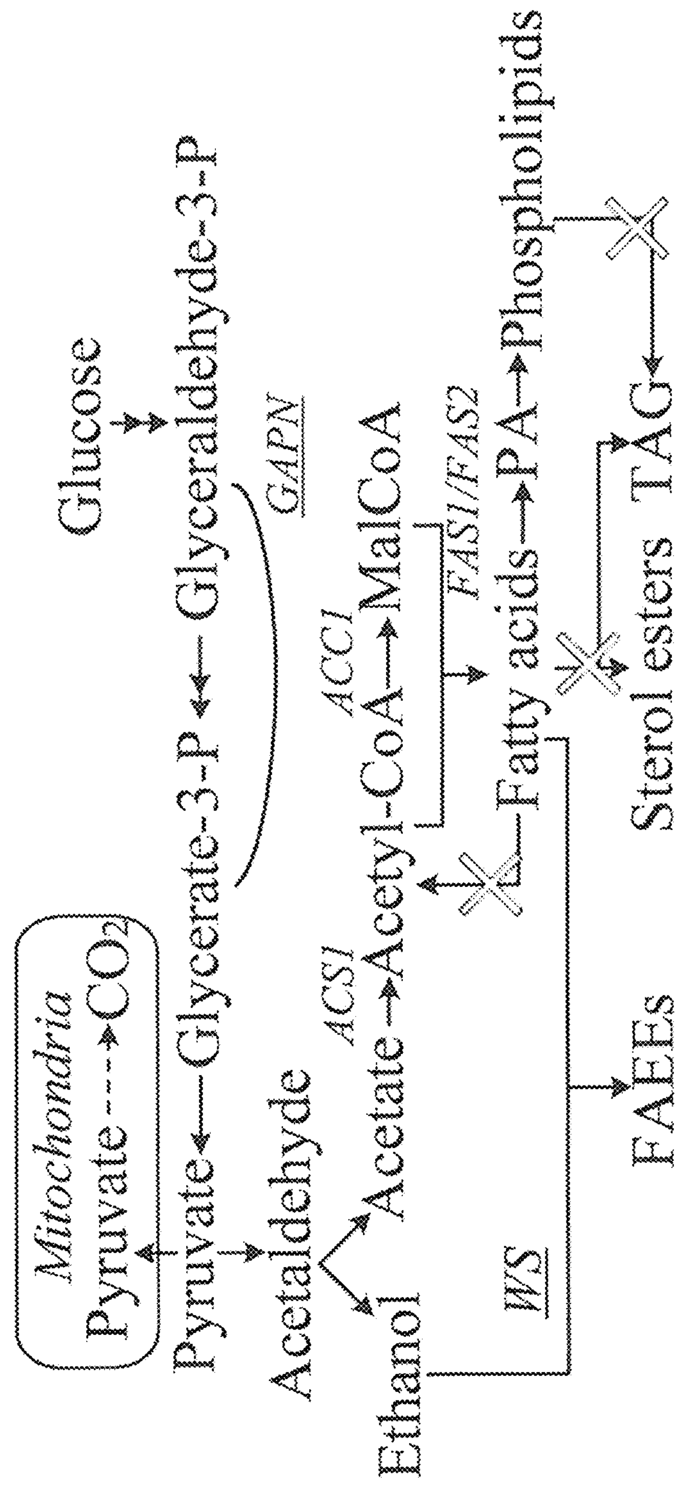
FIG. 8 shows an overview of different metabolic engineering strategies for enhancing fatty acid derivative production in yeast. The heterologous enzymes are shown underlined.

Another preferred modification aimed at increasing the pool of fatty acids is the over-expression of acetyl coenzyme A synthase. In *S. cerevisiae*, cytosolic acetyl-CoA is produced by decarboxylation of pyruvate to acetaldehyde that is then converted further to acetate and acetyl-CoA (FIG. 1; FIG. 8), which is used for the synthesis of malonyl-CoA and FA biosynthesis. The supply of acetyl-CoA may become a shortage when the FA biosynthesis ability is severely reinforced. The step for biosynthesizing acetyl-CoA is catalyzed by acetyl-coenzyme A synthetase, which is encoded by two genes, ACS1 and ACS2, in *S. cerevisiae*. Compared to ACS2, ACS1 has been reported to show a considerably higher activity and therefore in this invention, ACS1 has been chosen to be over-expressed.

The genetically modified yeast cell of the present invention will provide for increased production of FA that is at least 2-fold higher than the amount of the ester produced by a control yeast that is not genetically modified as described herein.

Fatty Acids Consuming Pathways

Fatty acids are the precursor of Acyl CoA and the production host is engineered to produce fatty acid esters from acyl-CoA and ethanol. That's why it is important to improve the pool of fatty acids by down-regulating the fatty acid-consuming pathways. Most of the fatty acids are stored in the form of neutral lipids such as triacylglycerols (TAG) and steryl esters, which can constitute up to 70% of the total lipid content of the cell. In *S. cerevisiae*. TAG can be synthesized through two different pathways. As shown in FIG. 8, one is an acyl-CoA-dependent reaction that is catalyzed by acyl-CoA:diacylglycerol acyltransferase (encoded by DGA1 gene); another is phospholipids (PL) dependent reaction that is catalyzed by lecithin:cholesterol acyltransferase (encoded by the LRO1 gene). Steryl esters are formed from sterols through the action of the enzyme acyl-CoA:sterol acyltransferase (ASAT) which is encoded by ARE1 and ARE2 genes in *S. cerevisiae*.

Previous studies have shown that the quadruple mutant, *S. cerevisiae* H1246, in which DGA1, LRO1, ARE1 and ARE2 were disrupted, was no longer capable of producing any TAG or steryl esters and had no apparent growth defects under standard conditions (Sandager, Gustavsson et al. 2002). In stationary phase, the quadruple disrupted strain has a 2.5-fold increase in fatty acids. Using Cre-loxP system, the four genes, DGA1, LRO1, ARE1 and ARE2, were disrupted sequentially. The mutant would decrease or abolish the amount of FA converted to neutral lipid production.

The stored neutral lipids could be hydrolyzed at any moment to yield fatty acids. The liberated fatty acids and free fatty acids could in turn be oxidized to generate energy by ß-oxidation. *S. cerevisiae* has only one peroxisomal acyl-CoA oxidase, Pox1p, which is regarded as being the main enzymatic step controlling the flux through the ß-oxidation. Knocking out the endogenous POX1 gene to block fatty acid ß-oxidation would be beneficial for the accumulation of lipid.

Suitable modifications allowing this particular embodiment include deletion of the afore-mentioned key genes: DGA1, LRO1, ARE1, ARE2 and POX1. Thus, a yeast cell with all non-essential fatty acid conversion reactions deleted or attenuated, specifically those related with ß-oxidation, synthesis of phospholipids, triacylglycerol and sterol esters, would show a higher production of fatty acids and hence an over-production of FAEE.

On the other hand, as reported by several authors a decrease in ß-oxidation flux would increase lipid accumulation (Slocombe, Cornah et al. 2009; Steen, Kang et al. 2010).

Carbohydrate Biosynthesis Pathways

The modified yeast cell with e.g. an enhanced ability to overproduce fatty acids, should need much more NADPH, as two molecules of NADPH are required for each step in the elongation of the growing FA acyl chain (FIG. 1).

Basically, the availability of intracellular NADPH is enhanced by engineering the production host to express an NADH:NADPH transhydrogenase. The expression of one or more NADH:NADPH transhydrogenases results in an increased conversion of the NADH produced in glycolysis to NADPH. Specifically, the authors herein have designed a novel yeast strain expressing a heterologous NADP+ dependent glyceraldehyde-3-phosphate dehydrogenase (GAPN, coded by gapN gene) (FIG. 8), for augmenting the production of fatty acid derivatives. Heterologous expression of gapN, from *Streptococcus* mutants in yeast provides a further push on FA biosynthesis ability, meanwhile it also lead to a higher ethanol yield, which is another precursor for biodiesel (FIG. 8).

Establishment of FAEE Biosynthesis Pathway

One known method for producing fatty acid esters includes increasing the expression of ester synthases such as wax synthases (EC 2.3.1.75) (FIG. 2). A further increase might be obtained by increasing wax synthase's substrate availability e.g. overproducing fatty acids as suggested above.

A wild-type yeast cell does not have the metabolic machinery for producing FAEEs from fatty acids. Wax synthases, the enzymes catalyzing these reactions, are characteristics of organisms such as *Mycobacterium, Rhodococcus, Acinetobacter*, and *Marinobacter* strains that grow in environments where a carbon source was abundant relative to other nutrients such as phosphorous and nitrogen. The wax synthase sequence usually contains the catalytic motif HHXXXDG, which is reported to be crucial for enzymatic activity.

Wax synthase activity has never previously been described for yeast. In yeast, it was only shown that polypeptides Eht1p and Eeb1p have medium chain (C4-C8) fatty acid ethyl ester-synthesizing and -degrading activity. However, Kalscheuer et al. (2004) showed for the first time that low wax synthase activity could be detected in wild-type *S. cerevisiae* G175 using palmitoyl-CoA and 1-Hexadecanol as substrates. But no homologous sequence was detected in yeast. In addition, GC/MS analysis of total lipid extracts from wild-type *S. cerevisiae* showed that FAEEs were absent, even when the medium is supplied with fatty acids (oleic acid).

Therefore, the ability to synthesize long chain fatty acid ethyl esters may exist in yeast and it may be generated by the unspecific activity of Eht1p and Eeb1p, but the activity is very poor, which is not enough to form FAEEs (i.e. long chain fatty acid ethyl ester) from fatty acids in a wild-type yeast.

In a particular embodiment the inventors herein propose the use of a microbial wax ester synthase/acyltransferase (WS/DGAT) from *Acinetobacter baylyi* ADP1 as this enzyme is known to have the activity for short-chain alcohols and the ability to form FAEEs. It is obtained by expressing the atfA gene. This wax synthase may have sequence similarity with the nucleotide sequence of SEQ ID NO 1 (see attached Sequence Listing). However, the wax synthase from *Acinetobacter baylyi* ADP1 is a rather unspecific enzyme with broad spectra of possible substrates, and it was in fact bifunctional in vivo, also acting as a diacylglycerol acyltransferase (DGAT).

Genes with high homologies to the *Acinetobacter baylyi* ADP1 wax synthase have also been identified in other species. There are three unrelated families of wax synthase found in higher plants, mammals and bacteria. The wax synthase of plants shows no activity for short-chain alcohols.

Several heterologous wax synthases from other organisms were evaluated (Example 3). As suspected, most wax synthase had the highest activity for acyl-CoAs and alcohols with a chain length from 14 to 18, with a much lower specificity for ethanol. All the detected wax synthase (i.e. wax synthase from *Acinetobacter baylyi* ADP1, *Marinobacter hydrocarbonoclasticus* DSM 8798, *Rhodococcus opacus* PD630, *Mus musculus* C57BL/6, and *Psychrobacter articus* 273-4) have varied activity for ethanol and could lead to the formation of FAEEs. However the enzyme with highest activity for synthesizing FAEEs was found to be wax synthase from *Marinobacter hydrocarbonoclasticus* DSM 8798 (named CB2 in the present application). According to the present invention a yeast cell able to efficiently produce FAEEs that could directly be used as biodiesel should express a wax synthase from *M. hydrocarbonoclasticus* or wax synthase from *Psychrobacter articus* (Table 3).

Overexpression of native EEb1 gene coding for EeB1p, with the ability to synthesize medium chain fatty acid ethyl ester in combination with expression of selected WSs might lead to favorable results with regard to the synthesis of specific FAEEs. For this purpose, a wax synthase with the best-adapted substrate specificity should be chosen.

On the other hand, the standardization of methods of molecular evolution or protein fusion could help improving the preference of existing WSs for certain substrates, e.g. using error prone PCR, gene shuffling or more directed protein engineering of the WSs. For example it could lead to the identification of WSs with higher specificity for ethanol. The selection of WSs with high activity for ethanol is of course, of crucial importance for designing an effective biodiesel producer as biodiesel is generally composed of fatty acid ethyl esters (FAEE). Said fatty acids have generally a chain-length from 14 to 20 carbon atoms, within the optimal operating range for acyl-CoAs. A recombinant yeast cell expressing e.g a *M. hydrocarbonoclasticus* is a good choice for designing a FAEEs producer because of its high preference for ethanol.

The identified broad spectra of possible substrates of different WSs as shown in Table 3 of the invention herein (see below) allows for many biotechnological applications including but not limited to biodiesel production. Depending on the substrate specificity of the wax synthase (WS) enzymes, various mixtures of ester isomers and chain lengths can be generated. These esters relates to liquid wax esters that can be used for biofuel, lubricants, cosmetics, linoleum, printing inks as well as products related thereto, and solid wax esters used for candles, polishes as well as products related thereto. Another exemplary biotechnological application of wax synthase is spermaceti production. Spermaceti is mainly composed by cetyl palmitate and cetyl myristate, and is widely used in cosmetics, pharmacy and also in candles.

A wax synthase polypeptide of the present invention may be isolated and obtained from other sources including microorganisms isolated from nature. People skilled in the art know how to screen a genomic or cDNA library for this purpose. Once a polynucleotide sequence encoding a polypeptide has been detected it can be isolated or cloned by utilizing techniques, which are well known to those of ordinary skill in the art.

Here again we have used plasmid pSP-GM2, derived from pESC, which is a common plasmid with high copy number. The original weaker promoters in pESC were exchanged by two strong promoter TEF1 and PGK1, respectively, to construct pSP-GM2. The high copy number and the strong driven by TEF1 ensures high-level expression of the WS. A polynucleotide encoding a wax synthase polypeptide of the present invention may be present in the yeast cell as a vector or integrated into a chromosome (S. Partow et al.).

Enzyme acting as Wax Ester Transporters.

As mentioned herein, the engineered cell expressing a wax synthase would be able to synthesize fatty acid esters e.g. FAEEs. The transfer of esters to the fermentation medium is dependent on their composition. It decreases drastically with increasing chain length, e.g. from 100% for ethyl hexanoate, to 54-68% for ethyl octanoate and 8-17% for ethyl decanoate. A wax ester transporter would facilitate the release of esters to the fermentation medium.

In one embodiment the invention herein uses a plant wax ester transporter (Pighin, Zheng et al. 2004). For example, Cer5 from Arabidopsis facilitates the export of very long chain aldehydes, ketones, alcohols, alkanes, esters and other possible fatty acids derivatives.

Strain and Polypeptide Characterizations

The wax synthase activity is an important parameter. It is measured according to previous publications (Kalscheuer et al., 2004). Basically, crude extracts are prepared from *S. cerevisiae* strains and added into a reaction system containing [1-14 C] palmitoyl-CoA and alcohols with specific chain. The test assays are incubated at 35° C. for 30 min, and stopped by extraction with chloroform/methanol. The extracts are separated by TLC. Spots corresponding to waxes are scraped from the plates, and radioactivity is measured by scintillation counting.

The FAEEs, are detected by GC-MS. Briefly, total lipids are first extracted from *S. cerevisiae* strains, and then run on a TLC plate. Spots corresponding to FAEEs are scraped from the plates, and resolved in chloroform/methanol, which is then measured by GC-MS.

The genetically modified yeast cells hereby disclosed may be included in a composition further comprising additional components selected from, but not limited to, the group consisting of: buffers; stabilizers; protease-inhibiting agents; hydrolytic enzymes, saccharolytic enzymes; cell membrane- and/or cell wall-preserving compounds, nutritional media appropriate to the cell; and the like.

For expressing the heterologous sequences, the yeast cells are cultured in a medium supplemented with carbohydrate as the only externally supplied source. Compounds included in this group, but not limited to, are glucose, fructose, galactose, xylose, arabinose, sucrose, maltose, starch, cellulose, and hemicellulose In this invention instead of providing the alcohol in the fermentation media as is known in the art e.g. when *E. coli* is used as biodiesel factory, Applicant has developed a genetically engineered microorganism that can produce wax esters in a controllable and economic fashion without the need of fatty acids or ethanol supplementation.

In specific embodiments the carbohydrate concentration in the culture medium is between 20 g/l and 50 g/l. Additional components of the culture media are yeast nitrogen base and CSM-Ura.

Accordingly, the present invention relates to a fungal cell system for producing fatty acyl ethyl esters (FAEE), said system comprising a fungal cell, and an expression vector encoding at least one wax synthase, wherein the metabolism of said fungal cell is additionally modified, said modification providing for down-regulation, attenuation, deletion and/or over-expression of one or more gene(s) selected from the group consisting of genes encoding one or more enzyme(s) involved in at least one of said fungal cell's fatty acid synthesizing pathways, fatty acid consuming pathways and carbohydrate biosynthesis pathways, and/or selected from the group consisting of genes encoding one or more enzyme (s) acting as wax ester transporter(s) of said fungal cell. The invention also relates to a fungal cell which is a yeast cell.

When herein down-regulation, attenuation, deletion and/or over-expression of one or more gene(s) is referred to, this means that the expression/translation/transcription level of the gene or the gene product has been altered in some manner. The manipulation herein could be achieved by medium supplementation, genetic engineering, or synthetic biology. Regulated genes include genes that could be translated into protein, as well as genes that are transcribed into types of RNA that are not translated into protein. Gene regulation could be made by altering the structural or control region, introducing more copy number, deactivating the corresponding repressor gene or activating the inducible gene, increasing the RNA stability of the gene, and combinations thereof.

Fatty acid ethyl esters (FAEEs) are esterification products of ethanol and fatty acids. Biodiesel is one kind of mixture of wax esters (FAEEs). The biosynthesis of FAEE is catalyzed by wax ester synthase, also called wax synthase (WS). The chain-length and degree of un-saturation and branching of the fatty acid may vary. Generally, this site of the ester is at least 8, 10, 12, 14, 16, 18, 20, 22, 24, or 26 carbons in length and can be mono-, di-, or tri-unsaturated.

The present invention provides genetically modified yeast cells that have at least one heterologous polynucleotide encoding a polypeptide involved in a FAEE biosynthesis pathway. The present invention also relates to other genetically modified fungal cells, as exemplified herein, that have at least one heterologous polynucleotide encoding a polypeptide involved in a FAEE biosynthesis pathway.

A fungal cell used in the context of the present invention can be selected from the group of fungal cells consisting of *Saccharomyces, Saccharomyces cerevisae Hansenula polymorpha, Kluyveromyces, Pichia, Candida albicans, Aspergilli, Rhodotorula rubra, Torulopsis, Trichosporon cutaneum, Trichoderma reesei, Apiofrichum curvafum, Yarrowia lipolytica*, and *Cryptococcus curvatus*. An example of a fungal cell that can be used is *Saccharomyces cerevisiae* CEN.PK113-5D (van Dijken, J. P., et al., 2000) A modification of the metabolism of a fungal cell according to the present invention can be genetic and effectuated by the introduction of one or more exogenous expression vector(s) into said fungal cell. In the context of the invention, said one or more exogenous expression vector(s) can be a plasmid, or another carrier such as exemplified herein. The vector also comprises a structural gene for selection of transformed cells, such as URA3, HIS3.

In aspects of the invention, said genetic modification of said fungal cell provides for an increased supply of fatty acyls to the metabolism of said fungal cell. Furthermore, said fungal cell can be genetically modified to stimulate overproduction of fatty acids, as further described herein.

In aspects of the invention, a modification to a fungal cell system as defined herein is performed to any one or more of the following genes, or its expression products: ACB1 (ACBP, acyl-CoA-binding protein), ACC1 (Acetyl-CoA carboxylase), FAS1, FAS2 (Fatty acid synthase), gapN (NADP+ dependent glyceraldehyde-3-phosphate dehydrogenase), ACS1 (Acetyl-CoA synthetase), DGA1 (Acyl-CoA:diacylglycerol acyltransferas), LRO1 (Lecithin:cholesterol acyltransferase), ARE1, ARE2 (Acyl-CoA:sterol acyltransferase), and POX1 (Peroxisomal acyl-CoA oxidase).

In other aspects, optionally in combination with other modifications, said modification to said fungal cell is performed by a knockout/deletion of one or more of the genes DGA1, LRO1, ARE1, ARE2, and POX1.

According to the invention, a modification to a fungal cell as described herein can also be performed by overexpressing one or more gene product(s) by the introduction of one or more expression vector(s) encoding said one or more gene product(s), said one or more gene product(s) being selected from the group consisting of: acyl-CoA-binding protein, Acetyl-CoA carboxylase (ACC1), NADP+ dependent glyceraldehyde-3-phosphate dehydrogenase, Fatty acid synthases (FAS1, FAS2) and Acetyl-CoA synthetase (ACS1).

According to the invention, a modification can also provide for an overexpression of ACC1 in combination with an increased expression of FAS1 and FAS2. In some aspects of the invention, the modification of ACC1 is performed by the introduction of an expression vector and an increased expression of FAS1/FAS2 is performed by replacing the promoter thereof (the promoter of FAS1/FAS2). In one aspect of the invention, the ACC1 gene is modified by virtue Ser659Ala and Seri 157Ala of said ACC1 gene being replaced (SEQ ID NO:16).

The invention also provides for a fungal cell system as defined herein, wherein said wax synthase encoded by said expression vector is heterologous. In this context, a "heterologous" wax synthase refers to a wax synthase originating from a different organism than the fungal cell used in the fungal cell system.

A fungal cell system as defined herein can comprise a wax synthase obtained from one or more of the species *Mycobacterium, Rhodococcus, Acinetobacter, Mus Musculus* and/or *Marinobacter*. Furthermore, more specifically, said at least one wax synthase can be selected from the group consisting of *Acinetobacter baylyi* ADP1, *Marinobacter hydrocarbonoclasticus* DSM 8798, *Rhodococcus opacus* PD630, *Mus musculus* C57BL/6, and *Psychrobacter articus* 273-4. A gene expressing said wax synthase used herein can be codon optimized and comprise a nucleic acid sequence encoded by any one of SEQ ID NO:1, SEQ ID NO 4, SEQ ID NO 5, SEQ ID NO 6 and/or SEQ ID NO 7. Also encompassed by the present invention are nucleic acid sequences having at least 80% identity with the presented sequence, such as approximately at least 80, 82, 85, 87, 90, 92, 95, 97, or 99% identity with the presented sequence. A nucleotide sequence disclosed herein can be from a natural species, a mutated version of a naturally occurring wax synthase, or a redesigned enzyme produced by protein engineering, the wax synthases being mutated or redesigned still maintaining their activity when expressed. The present invention also relates to a wax synthase having at least 80%, such as at least 80, 82, 85, 87, 90, 92, 95, 97, or 99% in sequence identity with an amino acid sequence corresponding to any of the wax synthases presented herein.

A wax synthase of the fungal cell system according to the present invention can be encoded by one or more of the following expression vectors pSP-B1, pSP-B2, pSP-B3, pSP-B4 and/or pSP-B5. These expression vectors are further defined herein, e.g. in the experimental section, and in FIG. 7A-7E. The nucleic acid sequences of the prior mentioned vectors are SEQ ID NO 31, SEQ ID NO 32, SEQ ID NO 33, SEQ ID NO 34, and SEQ ID NO 35. The present invention also relates to expression vectors pSP-B1, pSP-B2, pSP-B3, pSP-B4 and/or pSP-B5, wherein certain parts thereof have been slightly modified or parts have been removed, said expression vectors still retaining their activity, as well as expression vectors comprising any one of the sequences SEQ ID NO:30-35.

According to the invention, said expression vector encoding said one or more wax synthase(s) can be an episomal plasmid (single copy plasmids) or a high-copy plasmid. A single copy plasmid is defined as a plasmid that exists only as one or a few copies in each host. A high copy plasmid is a plasmid which will provide for a longer expression in the host as it will be present in more copies than the single copy plasmid.

In the context of the present invention, said expression vector encoding said wax synthase can provide for chromosomal integration into the chromosome of said fungal cell. Such an event is further illustrated in FIGS. 9 and 10 and in the experimental section (Example 7).

To a fungal cell system as defined herein, carbohydrates can be supplied as an external substrate to said fungal cell system for the production of FAEE. Said carbohydrates can be selected from the group consisting of glucose, fructose, galactose, xylose, arabinose, sucrose, maltose, starch, cellulose, and hemicellulose.

In some aspects of the invention, additionally either or both of the genes Eht1p and Eeb1p of said fungal cell, are overexpressed by said fungal cell. It was shown that Eht1p and Eeb1p have medium chain fatty acid ethyl ester (including ethyl hexanoate)-synthesizing and -degrading activity (Lilly, M., F. Bauer, M. Lambrechts, J. Swiegers, D. Cozzolino, and I. Pretorius. 2006. The effect of increased yeast alcohol acetyltransferase and esterase activity on the flavour profiles of wine and distillates. Yeast 23:641-659.). Eht1 preferred short-chain substrates (highest production was for ethyl butanoate), whereas Eeb1 preferred longer chain substrates (highest production was for ethyl octanoate) (Saerens, S., K. Verstrepen, S. Van Laere, A. Voet, P. Van Dijck, F. Delvaux, and J. Thevelein. 2006. The *Saccharomyces cerevisiae* EHT1 and EEB1 genes encode novel enzymes with medium-chain fatty acid ethyl ester synthesis and hydrolysis capacity. Journal of Biological Chemistry 281: 4446.).

The present invention also relates to the use of an fatty acyl ester, such as a fatty acyl ethyl ester (FAEE), produced by a fungal cell system as defined herein as a component in a biofuel, such as biodiesel, a lubricant, cosmetic, linoleum, printing ink, and/or a solid wax ester used for candles and/or polishes.

The present invention also relates to a composition comprising a fungal cell system as defined herein, said composition further comprising at least one additional component selected from the group consisting of: buffers; stabilizers; protease-inhibiting agents; hydrolytic enzymes, saccharolytic enzymes; cell membrane- and/or cell wall-preserving compounds, nutritional media appropriate to the cell; and the like.

The present invention also relates to a method for producing fatty acyl ethyl esters (FAEE), said method comprising:

a) providing a fungal cell system as defined herein in a culture broth,
b) adding one or more sources of carbohydrates as an external substrate to said fungal cell system;
c) and wherein said FAEE are thereafter retrieved by extraction from said culture broth.

Said carbohydrates can be selected from the group consisting of: glucose, fructose, galactose, xylose, arabinose, sucrose, maltose, starch, cellulose, and hemicellulose. Considering the importance of developing second generation processes based on biomass, it will be a promising advantage how the biofuels can be produced from xylose, cellulose, and hemicellulose, which yeast does not naturally consume.

The invention also relates to a composition comprising a fungal cell which metabolism is modified thereby possessing an increased flux towards fatty acid biosynthesis; and one or more expression vectors encoding one or more wax synthase (s). Such a fungal cell can be any fungal cell as described herein, i.e. *Saccharomyces, Saccharomyces cerevisae Hansenula polymorpha, Kluyveromyces, Pichia, Candida albicans, Aspergilli, Rhodotorula rubra, Torulopsis, Trichosporon cutaneum, Trichoderma reesei, Apiofrichum curvafum, Yarrowia lipolytica*, and *Cryptococcus curvatus*. Furthermore, said wax synthase in such a composition can be selected from *Mycobacterium, Rhodococcus, Acinetobacter, Mus Musculus* and/or *Marinobacter*. A modification of such a fungal cell can be performed in any manner exemplified herein, such as by down-regulation, attenuation, deletion and/or over-expression of one or more gene(s) selected from the group consisting of genes encoding one or more enzyme (s) involved in at least one of said fungal cell's fatty acid synthesizing pathways, fatty acid consuming pathways and carbohydrate biosynthesis pathways, and/or selected from the group consisting of genes encoding one or more enzyme (s) acting as wax ester transporter(s) Such a fungal cell can be used for producing biofuel esters, such as biodiesel, lubricants, cosmetics, linoleum and printing inks, and/or the solid waxes used for candles and polishes.

The present invention also relates to a yeast cell having an increased metabolic flux towards fatty acid ester biosynthesis, said yeast cell expressing at least one wax synthase selected from the group consisting of *Acinetobacter baylyi* ADP1, *Marinobacter hydrocarbonoclasticus* DSM 8798, *Rhodococcus opacus* PD630, *Mus musculus* C57BL/6 and *Psychrobacter articus* 273-4 in combination with over-expressing the protein ACBP (acyl-CoA-binding protein). Said yeast cell can for example be *Saccharomyces cerevisae*

PREFERRED EMBODIMENTS

In a preferred embodiment the invention teaches a method for increasing fatty acid production in yeast cells via over-expression of ACBP.

*Saccharomyce cerevisae* is the preferred host for carrying out the invention, as it is a popular host in basic and applied research apart from being a good ethanol producer, a precursor of esters and specifically of fatty acid ethyl esters. Nevertheless as previously mentioned herein other fungal cells allowing the present invention are selected from the group consisting of other *Saccharomyces* species as well as other fungi such as, but not limited to, *Hansenula polymorpha, Kluyveromyces, Pichia, Candida albicans, Aspergilli, Rhodotorula rubra, Torulopsis, Trichosporon cutaneum, Trichoderma reesei, Apiofrichum curvafum, Yarrowia lipolytica, Cryptococcus curvatus.*

In *S. cerevisae*, fatty acids act as a feedback inhibitor of acetyl CoA carboxylase, and also as an inhibitor of fatty acid oxidation in response to increased fatty acid availability. On the other hand we know that the regulatory properties of fatty acids are mediated through their activation to Acyl CoA. This means that in *S. cerevisiae*, fatty acid biosynthesis is inhibited by its product, the acyl-CoA.

Acyl CoA binding protein (ACBP) can attenuate the inhibitory effect of Acyl CoA by binding long- and medium-chain acyl-CoA esters with very high affinity. Owing to the high affinity of ACBP for Acyl CoA, the intracellular free Acyl CoA concentration is predicted to be very low. It has been demonstrated that overexpression of Acb1p and bovine ACBP in *S. cerevisiae* increased the total acyl-CoA pool size. The inventors herein have developed a yeast cell in which ACBP (acyl CoA binding protein) is over-expressed so that to down-regulate the activity of enzymes involved in the lipid metabolism and in this specific case for deregulating acetyl-CoA carboxylase. Increased ACBP expression is translated in low free Acyl CoA levels and more fatty acid availability.

Figure 4:
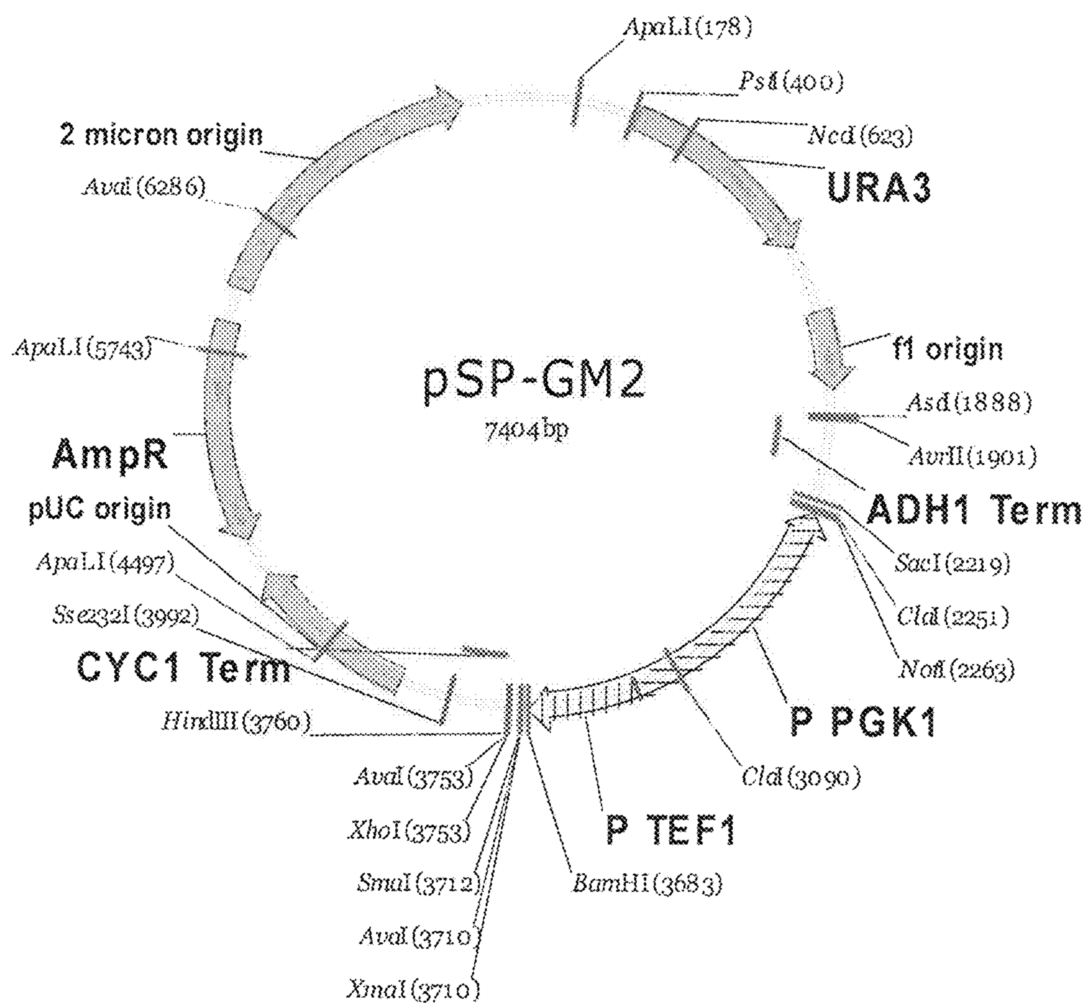
FIG. 4 shows the vector used for gene expression in the invention herein.

As previously explained, the present invention adopted a pESC derived plasmid as the expression vector. The plasmid pSP-GM2 shown in FIG. 4, can express two genes simultaneously. In this specific modification, Acb1 is also ligated to plasmid pSP-GM2 and under control of promoter PGK1 (S. Partow et a., 2010).

Over-expressing ACBP as used herein means altering the rate of transcription, Post-transcription, or translation of the gene encoding the protein as compared with the same rates in the yeast cell without modification.

Methods of testing for over-expression are well known in the art, for example transcribed RNA levels can be assessed using rtPCR, and protein levels can be assessed using SDS page gel analysis.

In a further preferred embodiment the invention teaches a system and a method in which a further increase in fatty acid production is obtained by down-regulating, attenuating, deleting or over-expressing additional genes encoding enzymes involved in the fatty acids synthesizing pathway, fatty acid consuming pathways, carbohydrate biosynthesis pathways or enzyme acting as wax ester transporters or a combination thereof. In this regard the genetically modified yeast cell of the present invention may include other modifications in addition to an over-expressed ACBP, but preferably it should contain genes encoding a combination of different wax synthases with high specificity for short-chain alcohols.

Basically, the genetic modifications may increase the level of enzymes involved in the different biosynthetic pathways, reduce feedback inhibition at different locations in the biosynthesis pathways, affect the availability of different substrates and cofactors used in said pathways, affect expression of genes coding those enzymes, etc.

Polypeptides according to the invention may be purified and isolated by methods known in the art. In particular, having identified the gene sequence, it is possible to use recombinant techniques to express the genes in the selected suitable host.

EXPERIMENTAL SECTION

Example 1

Construction of Biodiesel Production Host *Saccharomyces cerevisiae* CB1

In this experiment the wax ester synthase from *A. baylyi* ADP1 was expressed in a laboratory strain *Saccharomyces cerevisiae* CEN.PK113-5D (MAT-alpha ura3-52 HIS3 LEU2 TRP1 MAL2-8c SUC2) to create biodiesel producer, *Saccharomyces cerevisiae* CB1.

Briefly, cloning and DNA manipulations were all carried out in *E. coli* DH5a and were performed by standard procedures (Sambrook and Russell 2001). The sequence of the gene atfA with the reported wax synthase from *Acinetobacter baylyi* ADP1 was optimized for expression in a yeast host. The optimized sequence is given as SEQ ID NO 1, which was based on the published gene sequence (Gene bank accession no. AF529086). It was synthesized and provided by the DNA2.0 Company (Menlo Park, Calif.). SEQ ID NO 1 was amplified using the following oligonucleotides:

5'-CGGGATCCCGCTCGAGATGCGTCCATT-3' (SEQ ID NO 2) introducing BamHI restriction site (underlined) and;

5'-GGGGTACCCCAAGCTTGGGTTAGTTTGCAG-3' (SEQ ID NO 3) introducing HindIII restriction site (underlined). The BamHI/HindIII digested DNA sequence was ligated into vector pSP-GM2 (FIG. 4) and under control of the constitutively expressed promoter TEF1, which gave plasmid pSP-81 (FIG. 8). The cloned sequences were verified by sequencing. The plasmids pSP-GM2 and pSP-B1 were transformed into *S. cerevisiae* CEN.PK113-5D. The resulting strains were named *S. cerevisiae* CB0 and *S. cerevisiae* CB1, respectively. Synthetic minimal dropout (SD) medium lacking uracil was used to select for transformants.

Example 2

Characteristics of the Recombinant Host

The inoculated transformants *S. cerevisiae* CB0 and *S. cerevisiae* CB1 were cultured to late exponential growth period in 100 mL SD medium lacking uracil and containing 2% (w/v) glucose at 30° C. The cultures were then harvested. Cell-free extracts were prepared using a previously reported fast prep method for enzyme analysis (Hou, Vemuri et al. 2009). The lipid analysis were extracted from the lyophilized cell pellets using the reported method (Gu, Valianpour et al. 2004).

The wax synthase activities in the transformants were testified in vitro using [1-14 C] palmitoyl-CoA and 1-hexadecanol or ethanol as the substrates. Table 1 summarizes the results of enzyme analysis. A low wax synthase activity could be detected in negative control *S. cerevisiae* CB0 using 1-hexadecanol or ethanol as the substrates. In contrast, a significant high wax synthase activity was detected in *S. cerevisiae* CB1.

Figure 5:
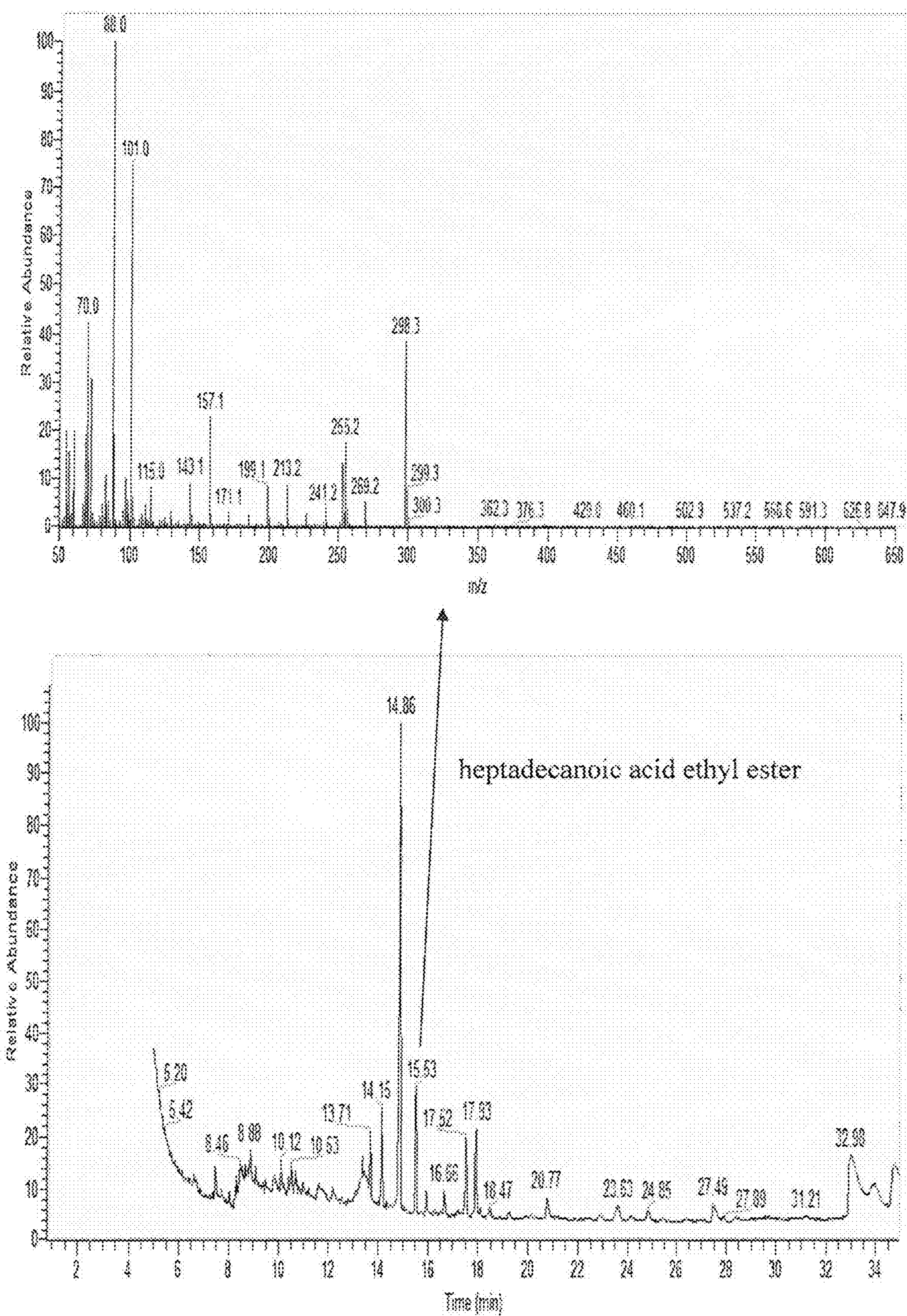
FIG. 5 shows GC-MS analysis of heptadecanoic acid ethyl ester produced by wax synthase expressing *S. cerevisiae* CB1 with heptadecanoic acid supplemented. The retention time is 15.53 minutes.
Figure 6:
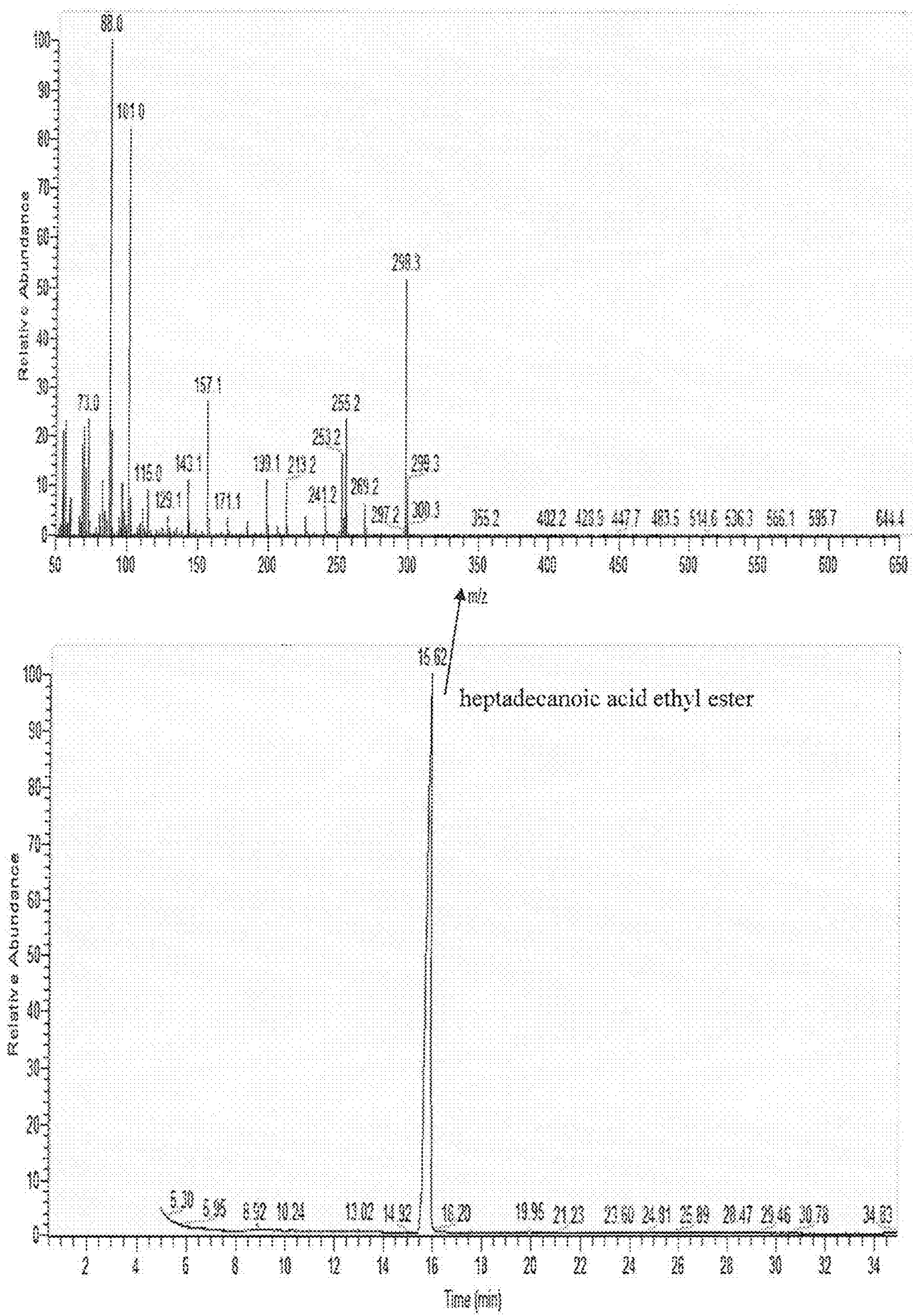
FIG. 6 shows a GC-MS analysis of standard heptadecanoic acid ethyl ester. The retention time is 15.62 minutes.
Figure 7A:
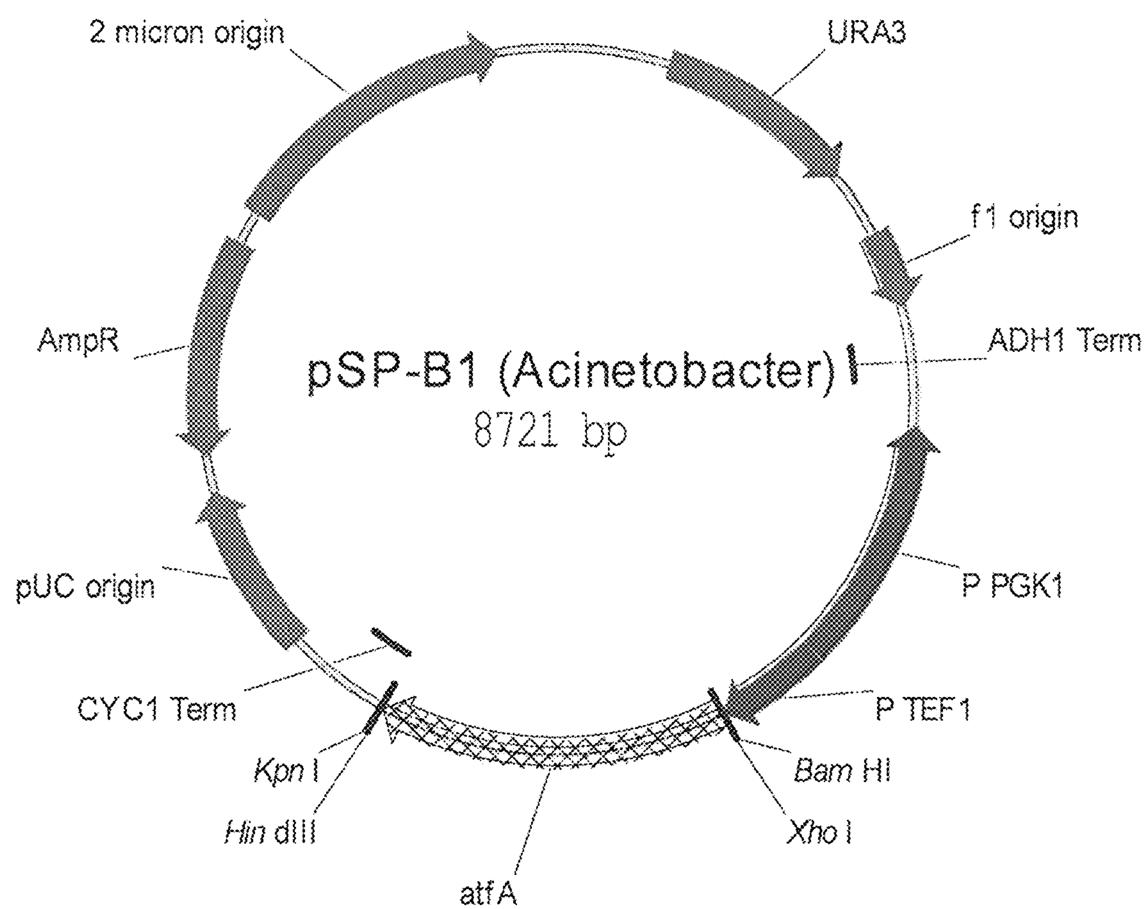
FIG. 7A-7E show the constructed plasmids for expressing WSs from *Acinetobacter baylyi, Marinobacter hydrocarbonoclasticus* DSM 8798, *Rhodococcus opacus* PD630, *Mus musculus* C571/68, and *Psychrobacter articus* 273-4.
Figure 7B:
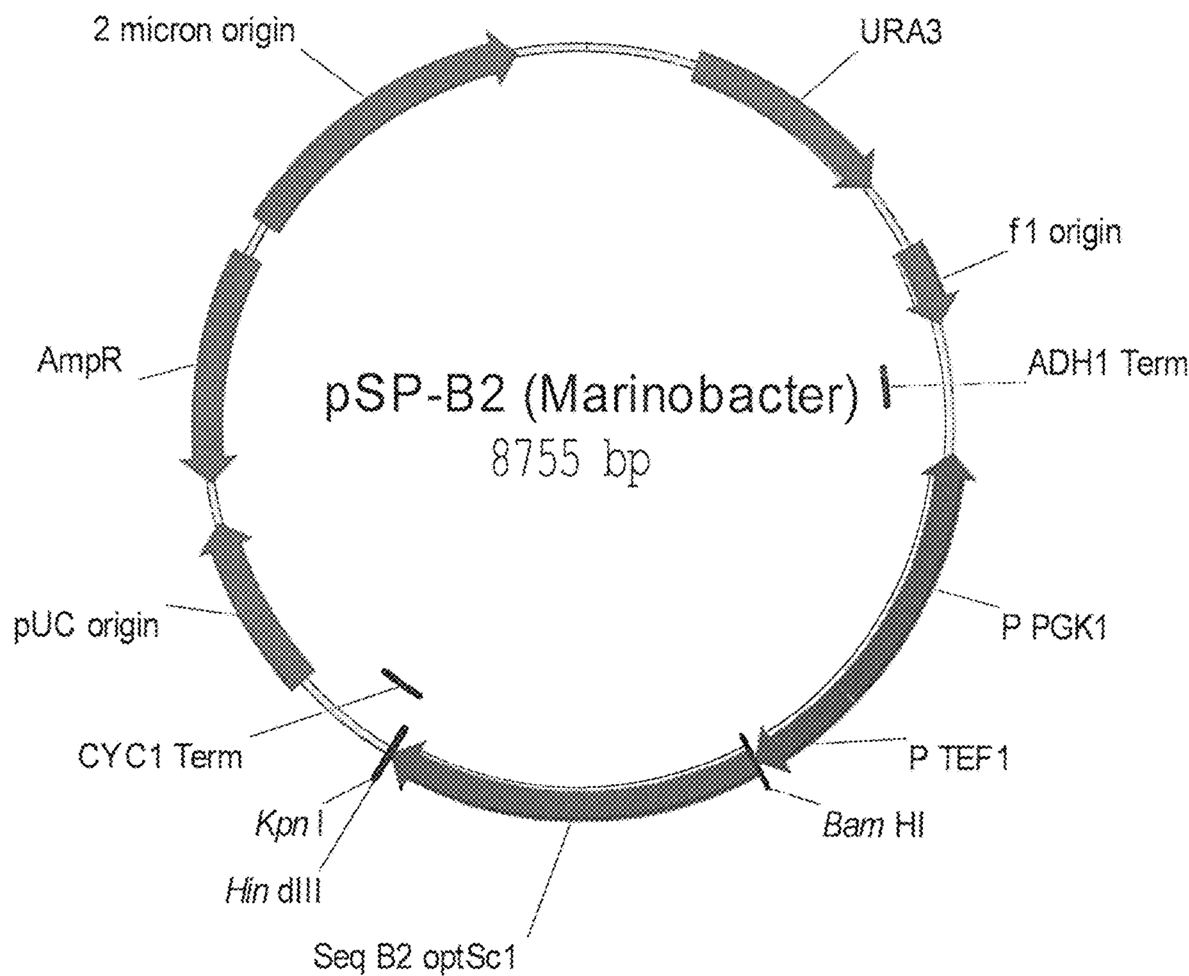
Figure 7C:
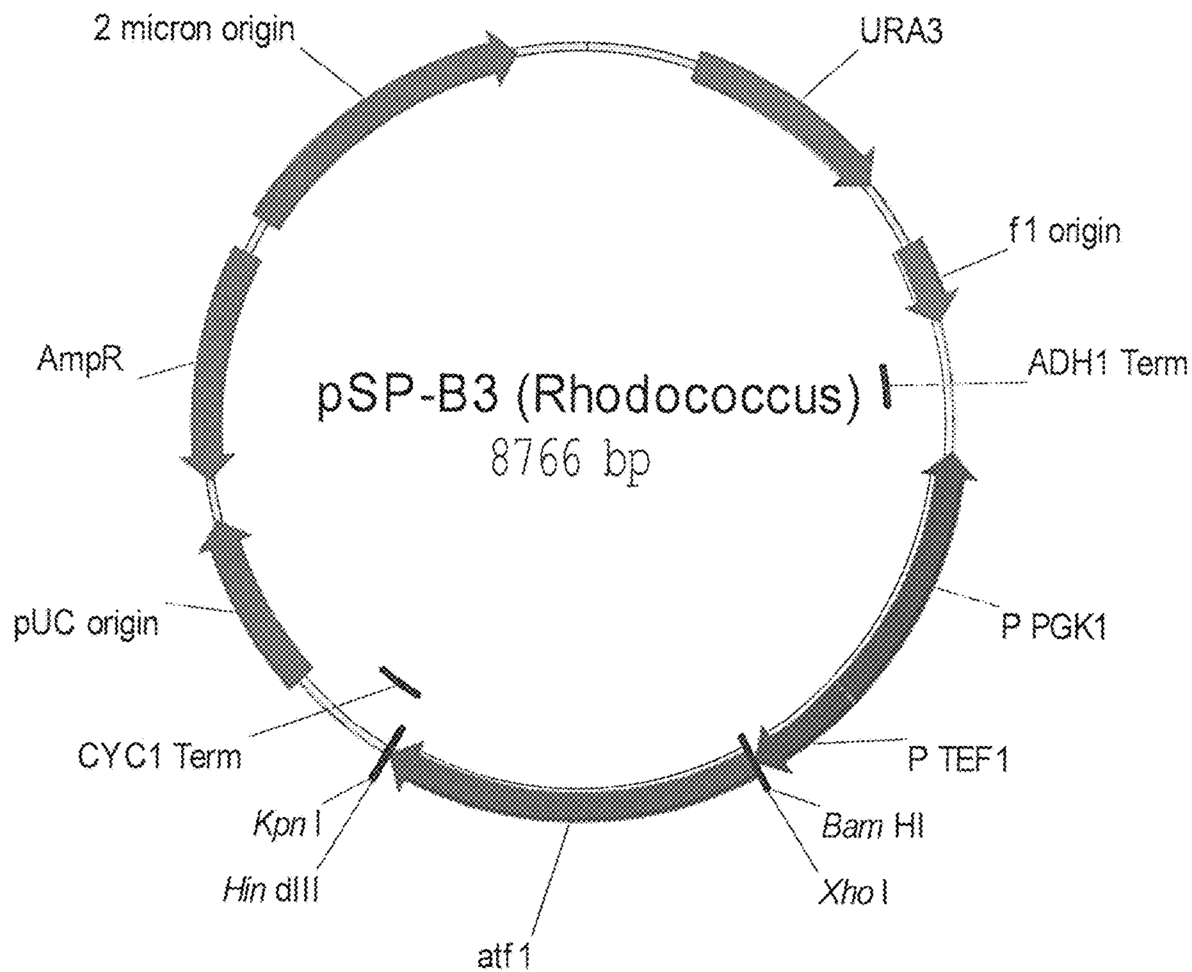
Figure 7D:
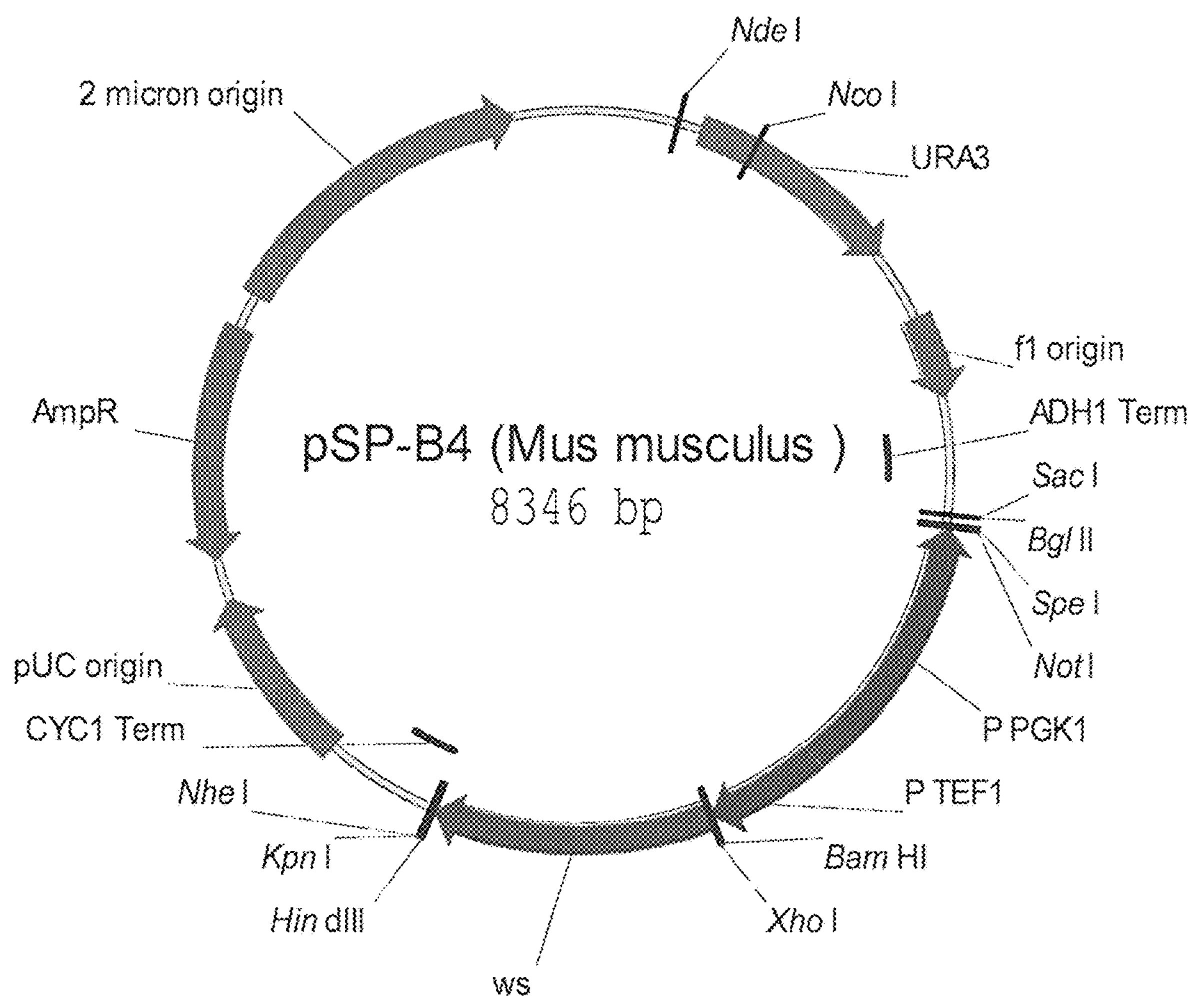
Figure 7E:
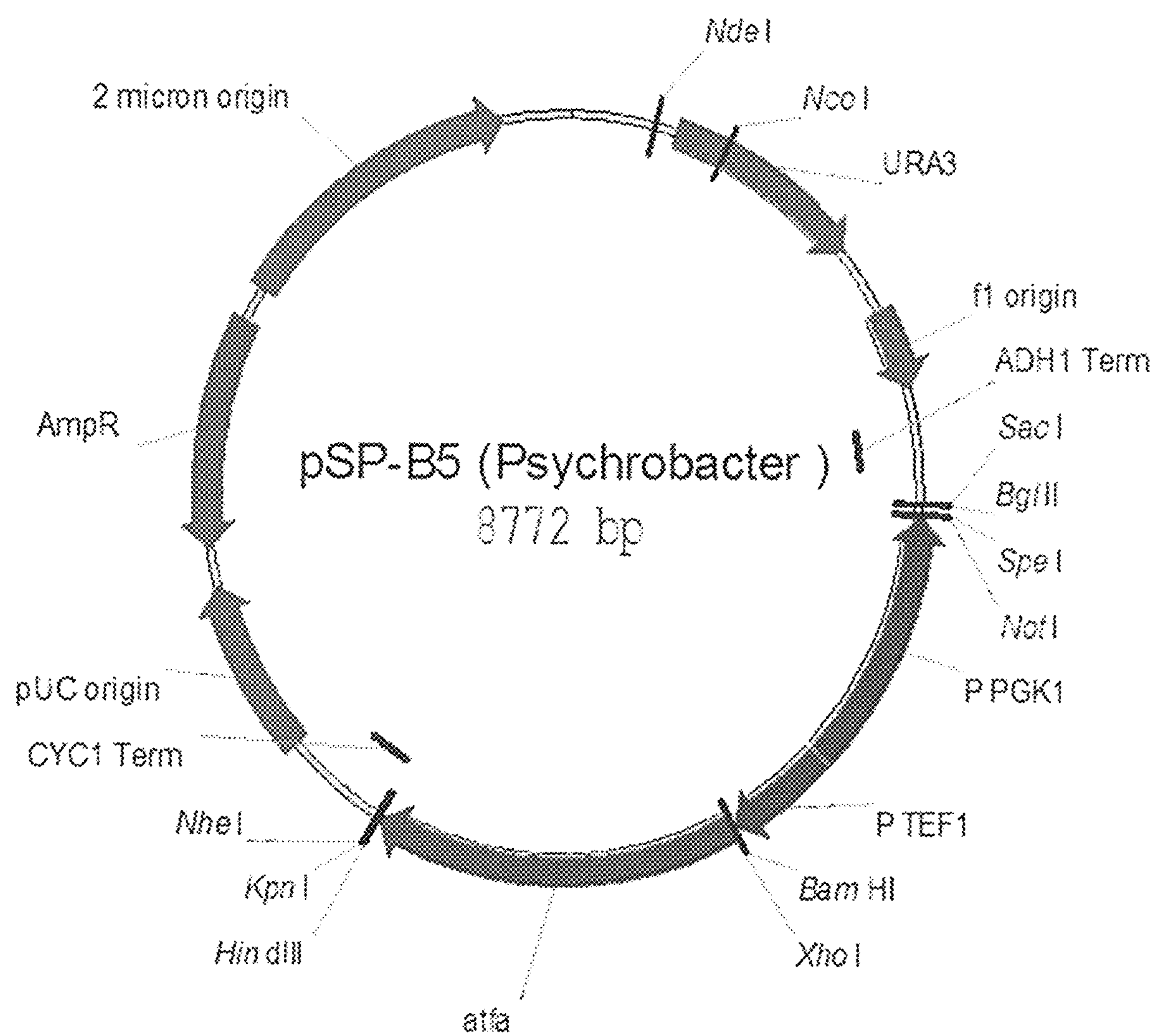

The lipid extraction was analyzed with Gas Chromatography/Mass spectroscopy (GC/MS). No FAEEs were detected in the negative control *S. cerevisiae* CB0 even when the cultured medium was supplemented with 0.1% (w/v) free fatty acids, heptadecanoic acid. In contrast, *S. cerevisiae* CB1 could produced FAEEs to a titer of 5.0 mg/L. The heptadecanoic acid ethyl ester was produced by *S. cerevisiae* CB1 when the cultured medium was supplemented with 0.1% (w/v) free fatty acids, heptadecanoic acid (C17), which doesn't synthesized by yeast itself. Taking heptadecanoic acid ethyl ester as an example for the GC/MS results, it eluted at around 15.6 min, and the parent ion mass spectrum of m/z 298 was clearly observed (FIG. 5). Additionally, structural confirmation was received by daughter ion scans of m/z 298 (FIG. 5). The spectrums are the same as in standard heptadecanoic acid ethyl ester (FIG. 6).

TABLE 1

WS activities in crude extracts of different recombinant *S. cerevisiae*

| Strain | Wax synthase activity[a] (pmol [mg cell extract · $min^{-1}$]) With palmitoyl-CoA and hexadecanol | With palmitoyl-CoA and ethanol |
|---|---|---|
| CB0 | 0.9 ± 0.2 | 0.67 ± 0.15 |
| CB1 | 41.6 ± 2.21 | 4.9 ± 0.55 |

[a]Data are mean values of two independent experiments ± SD.

Example 3

Evaluation of the Substrate Preference of Different WSs in Yeast

TABLE 2

Specific oligonucleotides used for PCR amplification of the synthesized WS sequences

| | Primer Sequence 5' → 3' | |
|---|---|---|
| | Upstream | Downstream |
| WS from *Marinobacter hydrocarbonoclasticus* DSM 8798 | CGGGATCCCGCTCGAGATGAAGAGATTAGG (SEQ ID NO 8) | GGGGTACCCCAAGCTTGGGTTACTTTCTAGTACG (SEQ ID NO 9) |
| WS from *Rhodococcus opacus* PD630 | CGGGATCCCGCTCGAGTTGACCGACGTGATTAC (SEQ ID NO 10) | GGGGTACCCCAAGCTTGGGTTAGCTAGCCACCACC (SEQ ID NO 11) |
| WS from *Mus musculus* C57BL/6 | CGGGATCCCGOTCGAGATGTTCTGGCCAACC (SEQ ID NO 12) | GGGGTACCCCAAGCTTGGGTTAACAATGACCAAC (SEQ ID NO 13) |
| WS from *Psychrobacter articus* 273-4 | CGGGATCCCGCTCGAGATGAGATTACTGACCGCTGT (SEQ ID NO 14) | GGGGTACCCCAAGCTTGGGTTAAGGGGCCAACT (SEQ ID NO 15) |

In this example, except for the wax synthase from *Acinetobacter baylyi* ADP1, four other putative WSs from *Marinobacter hydrocarbonoclasticus* DSM 8798, *Rhodococcus opacus PD*630, *Mus musculus* C57BL/6, and *Psychrobacter articus* 273-4 were optimized for expression in a yeast host. The optimized sequences could be seen in SEQ ID NO 4, SEQ ID NO 5, SEQ ID NO 6 and SEQ ID NO 7. Then they were synthesized by the DNA2.0 Company (Menlo Park, Calif.). These synthesized sequences were PCR amplified by using specific oligonucleotides introducing BamHI and HindIII restriction sites (Table 2 above). The BamHI/HindIII digested DNA sequences were ligated into pSP-GM2 (FIG. 4), respectively, and under control of the constitutively expressed promoter TEF1, which resulted in the plasmids pSP-B2, pSP-B3, pSP-B4 and pSP-B5 (FIG. 7B, 7C, 7D, 7E). Cloned sequences were verified by sequencing. The plasmids pSP-B2, pSP-B3, pSP-B4 and pSP-B5 were transformed into *S. cerevisiae* CEN.PK113-5D to construct *S. cerevisiae* CB2, CB3, CB4 and CB5, respectively. Synthetic minimal dropout (SD) medium lacking uracil was used to select for transformants.

The cell-free extracts from the constructed recombinant *S. cerevisiae* CB1, CB2, CB3, CB4 and CB5 were prepared as the method described in Example 2. The wax synthase activities in the transformants were testified in vitro using alcohols with various chain lengths as substrates Table 3 summarizes the results of enzyme analysis.

The substrate profiles in Table 3 show that CB2 and CB5 catalyzed ethanol with a higher activity, which could reduce the formation of byproducts and drive the carbon flux toward the target ethyl esters. Actually, CB2 and CB5 could produce FAEEs at yield of 6.3 mg/L and 2.3 mg/L, which are clearly higher than other wax synthase expressing yeast. Moreover CB2 catalyzed cetyl alcohol (1-Hexadecanol) with a higher activity, which is the choice for constructing the spermaceti producing yeast. Our findings clearly show that the substrate preferences of the different WSs are the instructions for producing certain wax esters.

TABLE 3

Acyl acceptor specificities with different alcohols in crude extracts of different recombinant *S. cerevisiae*

| | Wax synthase activity[a] (pmol [mg cell extract · min$^{-1}$]) | | | | |
|---|---|---|---|---|---|
| Acyl acceptor | CB1 | CB2 | CB3 | CB4 | CB5 |
| Ethanol | 4.6 ± 0.55 | 8.1 ± 1.87 | 2.7 ± 0.37 | 3.8 ± 0.51 | 5.9 ± 0.83 |
| Butanol | 10.8 ± 1.60 | 14.6 ± 1.75 | 6.8 ± 0.82 | 3.5 ± 0.53 | 4.2 ± 0.46 |
| 1-Hexanol | 17.3 ± 2.04 | 33.8 ± 3.77 | 16.1 ± 2.29 | 10.2 ± 1.59 | 18.7 ± 2.19 |
| 1-Octanol | 23.0 ± 2.39 | 45.7 ± 4.51 | 32.3 ± 3.84 | 22.3 ± 2.44 | 17.7 ± 1.67 |
| 1-Decanol | 19.7 ± 3.11 | 41.1 ± 4.13 | 37.3 ± 3.90 | 33.5 ± 2.22 | 27.5 ± 2.50 |
| 1-Dodecanol | 31.8 ± 3.48 | 48.4 ± 4.56 | 36.7 ± 3.78 | 44.2 ± 3.07 | 42.8 ± 3.11 |
| 1-Tetradecanol | 45.0 ± 4.72 | 49.7 ± 4.38 | 33.5 ± 3.66 | 35.1 ± 2.87 | 36.5 ± 3.03 |
| 1-Hexadecanol | 41.6 ± 2.21 | 49.0 ± 3.65 | 28.9 ± 3.29 | 35.5 ± 2.91 | 39.1 ± 2.72 |

[a]Data are mean values of two independent experiments ± SD.

Example 4

Metabolic Engineering Strategy for Enhancing Fatty Acid Biosynthesis-Expression of Heterologous NADP+ Dependent Glyceraldehyde-3-Phosphate Dehydrogenase In this invention supplying more NADPH is taken as an example to illustrate the metabolic engineering strategy for enhancing fatty acid biosynthesis. To make more NADPH, the heterologous expression of NADP+ dependent glyceraldehyde-3-phosphate dehydrogenase (gapN, from *Streptococcus mutants*) is used. The heterologous reaction is listed in FIG. 8.

The sequence of gapN (from *Streptococcus mutants*) was optimized for expression in a yeast host (SEQ ID NO 17) and was synthesized by DNA2.0 Company (Menlo Park, Calif.). The synthesized sequence was PCR amplified by using specific oligonucleotides:

```
                                        (SEQ ID NO 18)
5'-AAACAA GCGGCCGCACTAGTTTGACAAAAC-3'
introducing NotI restriction site (underlined)
and

                                        (SEQ ID NO 19)
5'-TTAATTAAGAGCTCAGATCTTTATTTGATATCAA-3'
introducing SacI restriction site (underlined).
The NotI/SacI digested DNA sequences
were ligated into pSP-GM2,
and transformed into host S. cerevisiae strain.
```

Example 5

Summary of Modifications Useful for Making Yeast with Increased FA Supply for Producing Wax Esters

TABLE 4 is a summary of modifications to construct engineered yeast cells that can efficiently biosynthesis FA for producing wax esters. The modifications can be combined together.

| Enzyme | Sources | Gene |
|---|---|---|
| Wax synthase | *Acinetobacter baylyi* ADP1 | atfA |
| | *Marinobacter hydrocarbonoclasticus* DSM8 798 | WS2 |
| | *Rhodococcus opacus* PD630 | atf1 |
| | *Mus musculus* C57BL/6 | AY611031 and AY611032 |
| | *Psychrobacter adieus* | YP_263530 |
| ACBP (acyl-CoA-binding protein) | *Saccharomyces cerevisiae* CEN.PK113-5D | Acb1 |
| Acetyl-CoA carboxylase | *Saccharomyces cerevisiae* CEN.PK113-5D | Desensitized ACC1 |
| Fatty acid synthase | *Saccharomyces cerevisiae* CEN.PK113-5D | FAS1, FAS2 |
| $NADP^+$dependent glyceraldehyde-3-phosphate dehydrogenase | *Streptococcus mutants* | gapN |
| Acetyl-CoA synthetase | *Saccharomyces cerevisiae* CEN.PK113 | ACS1 |
| Acyl-CoA: diacylglycerol acyltransferase | *Saccharomyces cerevisiae* CEN.PK113 | DGA1 |
| Lecithin: cholesterol acyltransferase | *Saccharomyces cerevisiae* CEN.PK113 | LRO1 |
| Acyl-CoA: sterol acyltransferase | *Saccharomyces cerevisiae* CEN.PK113 | ARE1, ARE2 |
| Peroxisomal acyl-CoA oxidase | *Saccharomyces cerevisiae* CEN.PK113 | POX1 |

Example 6

Fermentation

After combination of the above engineering strategies, the engineered host yeast holds the ability with increased flux towards FA biosynthesis. After combined wax synthase expression, it produces wax ester without the need for addition of exogenous fatty acids to the culture. In such an example, the engineered wax synthase expressing *S. cerevisiae* with an increased flux towards FA biosynthesis allow for high level production of biodiesel (FAEEs) from the only externally supplied substrate, carbohydrates. For large-scale biodiesel production, the engineered *S. cerevisiae* is cultured in 5 L fermentor. Glucose is continuously fed into the medium, in which maintained a high ratio of C/N. Meanwhile, dodecane (10%, v/v) was overlayed the medium to potentially prevent FAEEs evaporation and facilitate in-situ product capture.

Example 7

Plasmids Construction for Evaluation of Five Wax Ester Synthases on FAEE Production:

Briefly, cloning and DNA manipulations were all carried out in *E. coli* DH5a and were performed by standard procedures (Sambrook and Russell 2001). The five sequences of the wax synthase from different species were optimized for expression in a yeast host. Then they were synthesized and provided by the DNA2.0 Company (Menlo Park, Calif.). These five different sequences were amplified using the ligonucleotides primers, respectively (table 2). The five BamHI/HindIII digested DNA sequences were, respectively, ligated into vector pSP-GM2 and under control of the constitutively expressed promoter TEF1, which gave five different plasmids. These plasmids were transformed into *Saccharomyces cerevisiae* CEN.PK113-5D (MAT-alpha ura3-52 HIS3 LEU2 TRP1 MAL2-8c SUC2) to create five biodiesel producers. The method for yeast transformation is the standard LiAc/SS Carrier DNA/PEG method (Xiao 2006). Synthetic minimal dropout (SD) medium lacking uracil was used to select for transformants.

Figure 9:
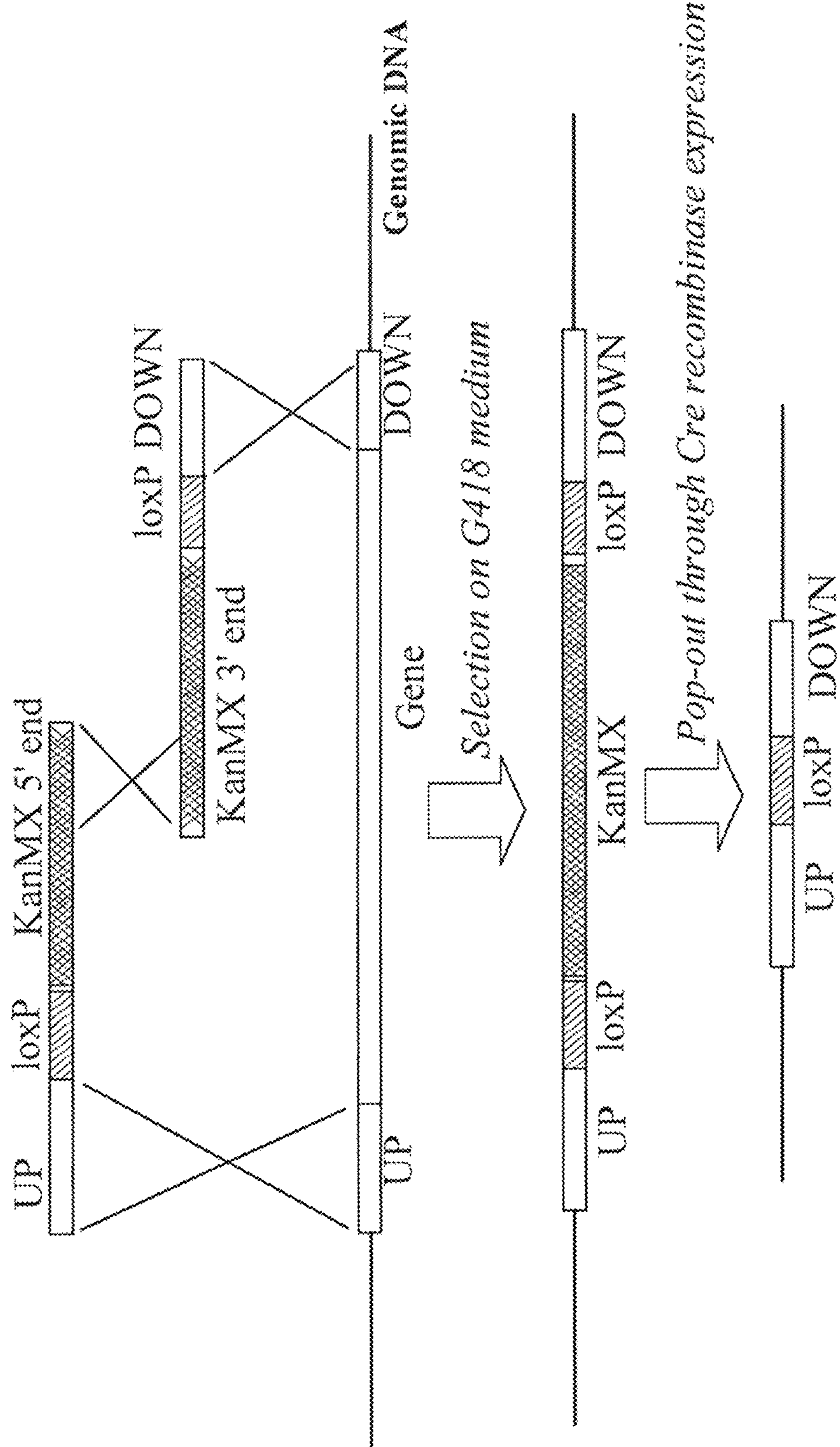
FIG. 9 shows the outline of the gene deletion method.
Figure 10:
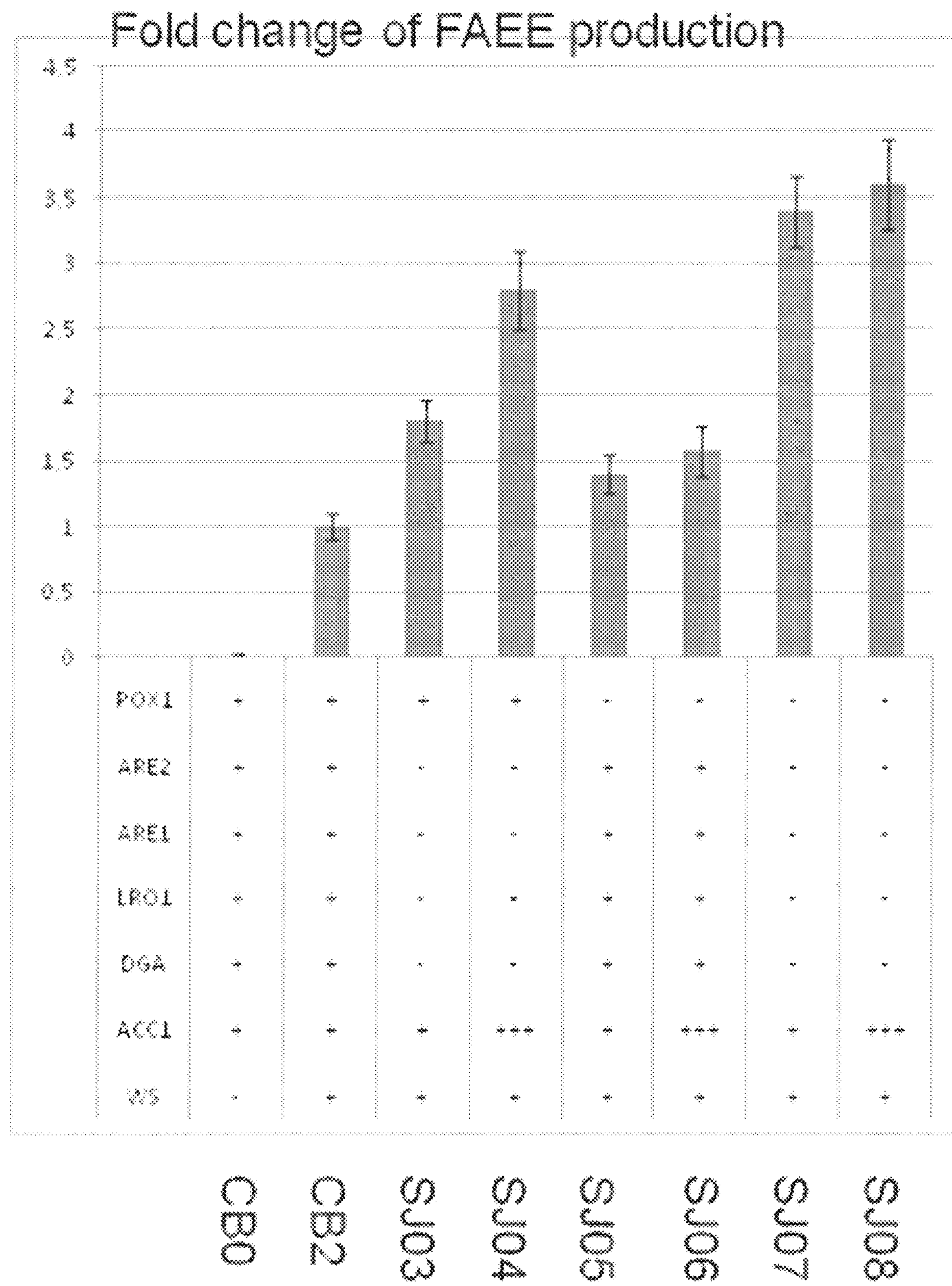
FIG. 10 shows biodiesel production in engineered strains.

Gene Deletions:

Shown in FIG. 9, the five genes (DGA1, LRO1, ARE1, ARE2, POX1) were deleted subsequently in *Saccharomyces cerevisiae* CEN.PK113-5D using the loop-out method with the help of loxP-KanMX-loxP cassette (Xiao 2006).

General Description and Method for the Chromosomal Integration

Wax synthase from *Marinobacter hydrocarbonoclasticus* DSM 8798 is suggested to have the highest activity for biodiesel production and chosen as the working enzyme. In the deletion strains, the related genes were introduced and constructed the following strains. The ability of biodiesel production was shown in FIG. 10, and the genotypes of strains were listed in Table 5. The overexpressed ACC1 were released its phosphorylation sites (Ser659Ala nad Ser1157Ala), as shown in SEQ ID NO 16.

TABLE 5

| Strain | Genetype or relevant Characteristics |
|---|---|
| SJ03 | ΔDGA1, ΔLRO1, ΔARE1, ΔARE2, with wax synthase (*Marinobacter*) overexpressed from plasmid pSP-GM2 |
| SJ04 | ΔDGA1, ΔLRO1, ΔARE1, ΔAPE2, with wax synthase (*Marinobacter*) and Acetyl-CoA carboxylase overexpressed from plasmid pSP-GM2 |
| SJ05 | ΔPOX1, with wax synthase (*Marinobacter*) overexpressed from plasmid pSP-GM2 |
| SJ06 | ΔPOX1, with wax synthase (*Marinobacter*) and Acetyl-CoA carboxylase overexpressed from plasmid pSP-GM2 |
| SJ07 | ΔDGA1, ΔLRO1, ΔAPE1, ΔARE2, ΔPOX1, with wax synthase (*Marinobacter*) overexpressed from plasmid pSP-GM2 |
| SJ08 | ΔDGA1, ΔLRO1, ΔAPE1, ΔAPE2, ΔPOX1, with wax synthase (*Marinobacter*) and Acetyl-CoA carboxylase overexpressed from plasmid pSP-GM2 |

Example 8

Figure 11:
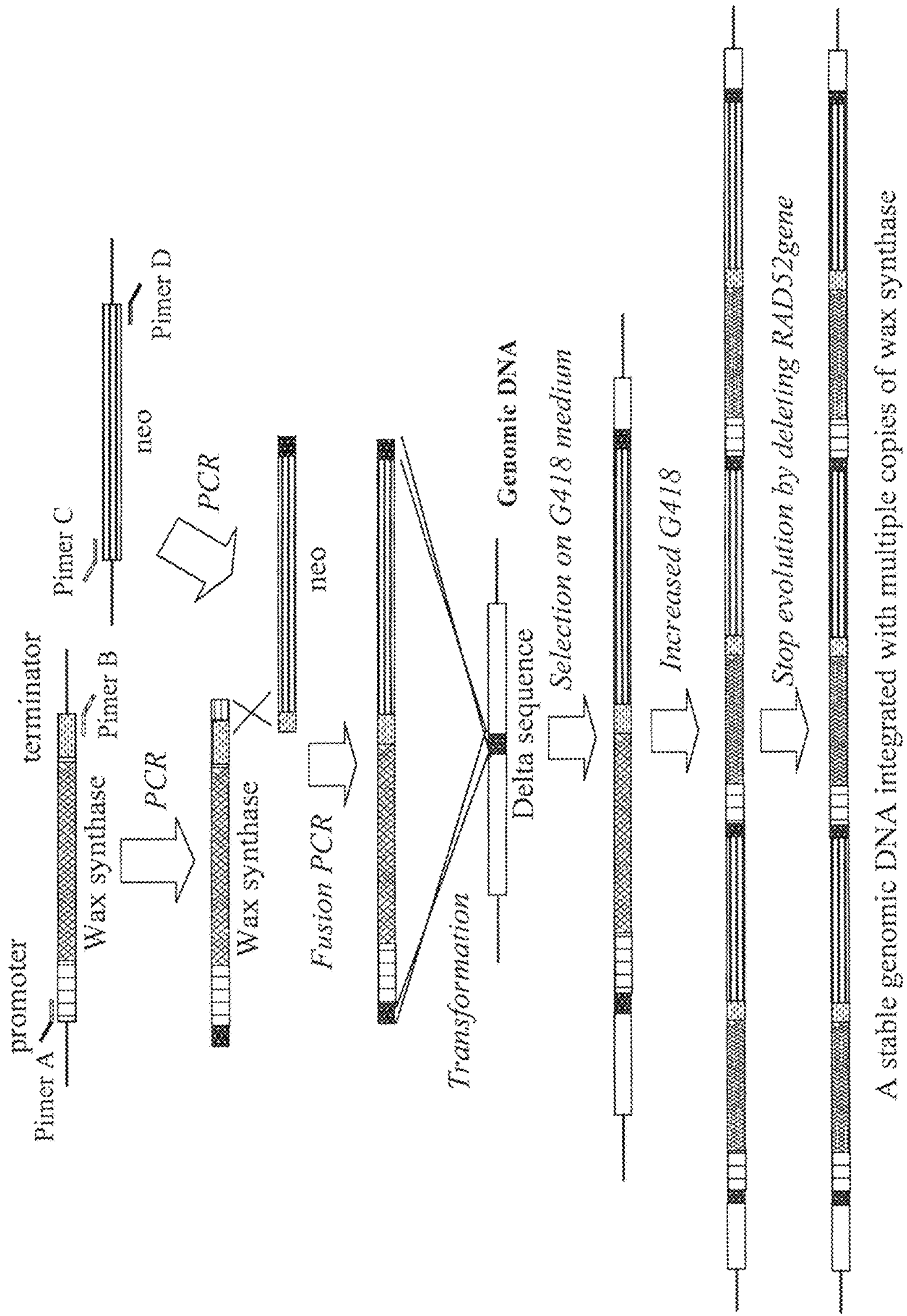
FIG. 11 shows a method for chromosomal integration. The chromosomal integration cassette, obtained by fusion PCR, contains wax synthase controlled by TEF1 or PGK1 and a selectable marker (neo) is delivered to the chromosome. Iterative tandem gene duplication is accomplished by selecting in the plates with higher antibiotics.

Although plasmids based methods have been used for biodiesel production, the plasmid is not genetic stable, which contributed the loss in productivity. In this work, we developed a plasmid-free method with high genetic stability and high gene copy expression for biodiesel production. Shown in FIG. 11, the wax synthase and bacterial neo gene (Neo, G418 resistance gene) were fused together, and integrated into delta sequence of chromosome by yeast transformation. The copies of delta sequence occur in multiple places throughout the yeast genome, and, under the selection of increasing concentration of G418, clones with multiple copies of the inserted gene can be generated. Finally, pathway copy number is stabilized by RAD52 knockout, and the resulting engineered to strain requires no selection markers and is unaffected by plasmid instabilities.

The WS (wax synthase) from *Marinobacter hydrocarbonoclasticus* DSM 8798 were evaluated under control of two different strong promoters, TEF1 and PGK1. Amplified by primer 1 and primer 2 (Table 6), the BamHI/HindIII digested WS sequence was ligated into vector pSP-GM2 and under control of the constitutively expressed promoter TEF1, which gave plasmid pSP-B2. Using plasmid pSP-B2 as the template, the WS sequence with TEF1 promoter and CYC1 terminator could be amplified with primer 3 and primer 4. The neo gene was amplified from plasmid pJEF1105 (Wang, Wang et al. 1996) with primer 5 and primer 6. Shown in FIG. 11, the 5' end of primer 3 and primer 6 are homolog to the delta sequence, which would facilitate the integration; the 5' end of primer 4 is homolog to neo gene and the 5' end of primer 5 is homolog to CYC1 terminator, which would facilitate sequence fusion. The two DNA sequences, TEF1 controlled WS (PCR product 1, FIG. 11) and neo gene (PCR product 2, FIG. 11), could be fused together as one by PCR amplification taken these two sequences as the template and primer 3 and 6 as the PCR primers. The fused DNA fragment (PCR product 3, FIG. 11) be transformed into yeast and selected on the plats with G418 concentration. Similarly, DNA fragment that contained PGK1 controlled WS and neo gene was also constructed and integrated into yeast.

Figure 12:
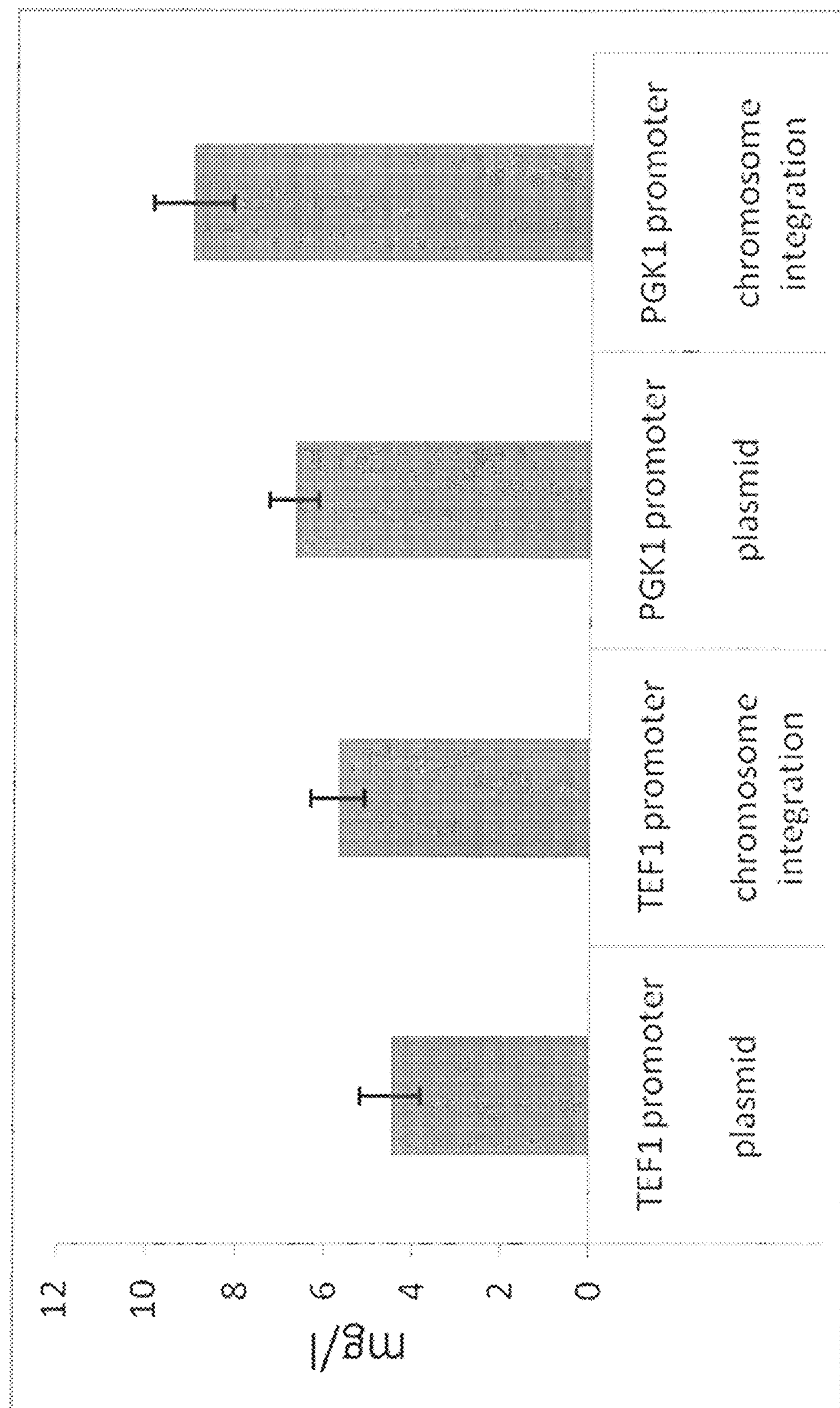
FIG. 12 shows the effect of different promoter and biodiesel production in plasmid or chromosome integration based strains.
Figure 13:
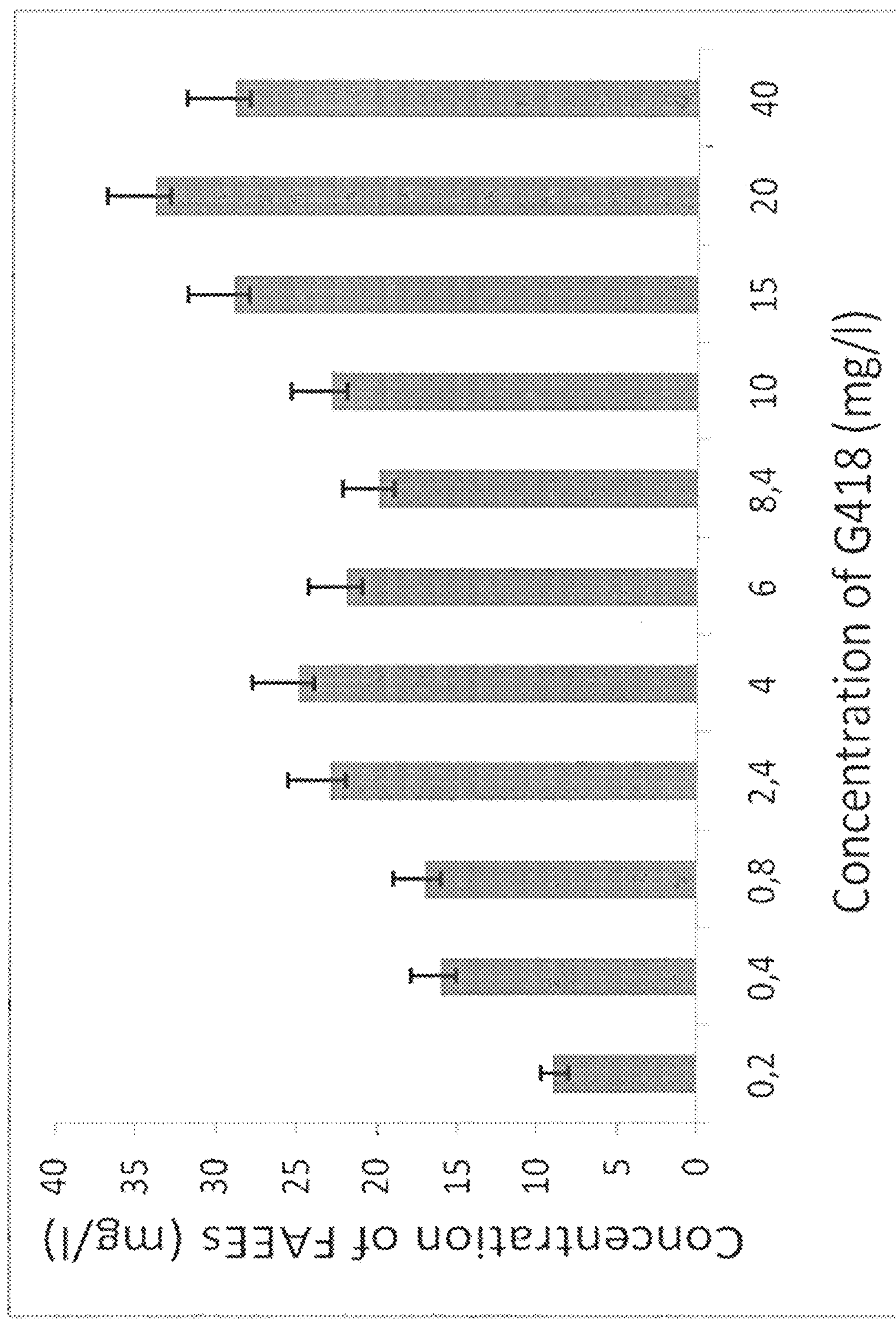
FIG. 13 shows the relationship of the concentration of biodiesel production and the concentration of G418.

Shown in FIG. 12, the initial results suggests PGK1 controlled WS have a higher productivity and chosen as the choice for selection on the plates with increasing G418 concentration. The colonies selected from the plate with higher concentration of G418 should contain higher copy number of WS, and contribute to a higher biodiesel production. FIG. 13 shows the relationship of the concentration of biodiesel production and the concentration of G418. Yield increased remarkably as more G418 was used in the chromosomal evolution until yield stopped increase when the supply of precursors limited the function of wax synthase. The chromosome integration constructed a stable pathway and the production is comparable or higher than those achievable using multicopy plasmids.

TABLE 6 primers list

| | Primer Sequence 5' → 3' |
|---|---|
| Primer 1 | CGGGATCCCGCTCGAGATGAAGAGATTAGG (SEQ ID NO: 20) |
| Primer 2 | GGGGTACCCCAAGCTTGGGTTACTTTCTAGTACG (SEQ ID NO: 21) |
| Primer 3 | GTTGGGATTCCATTGTTGATAAAGGCGcacacaccatagettcaaaatgtttc (SEQ ID NO: 22) |
| Primer 4 | GTGCAATGTAgatatcgagcgtcocaaaacc (SEQ ID NO: 23) |
| Primer 5 | GacgctcgaagatcTACATTGCACAAGATAAAAATATATCATCATGAACAAT (SEQ ID NO: 24) |
| Primer 6 | GCCTTTATCAACAATGGAATCCCAACCGCCGTCCCGTCAAGTC (SEQ ID NO: 25) |
| Primer 7 | ACAACAAATATAAAACAAGCGGCCGCACTATGAAGAGATTAGGTACTC (SEQ ID NO: 26) |
| Primer 8 | GGCGAAGAATTGTTAATTAAGAGCTCGGTACCCCAAGCTTGGGTTA (SEQ ID NO: 27) |
| Primer 9 | GTTGGGATTCCATTGTTGATAAAGGCGGAAGTACCTTCAAAGAATGGGGTC (SEQ ID NO: 28) |
| Primer 10 | CTTGTGCAATGTAGAGCGACCTCATGCTATACCTGAG (SEQ ID NO: 29) |
| Primer 11 | ATGAGGTCGCTCTACATTGCACAAGATAAAAATATATCATCATGAAC (SEQ ID NO: 30) |

Analysis:

The inoculated transformants of *S. cerevisiae* were cultured to late exponential growth period in 100 mL SD medium lacking uracil and containing 2% (w/v) glucose at 30° C. The cultures were then harvested. Cell-free extracts were prepared using a previously reported fast prep method for enzyme analysis (Hou, Vemuri et al. 2009). The wax synthase activities in the transformants were testified in vitro using [1-14 C] palmitoyl-CoA and 1-hexadecanol or ethanol as the substrates (Kalscheuer, Luftmann et al. 2004). ACCase (Acetyl-CoA carboxylase) activity was measured under a fume hood as the incorporation of radioactivity from $NaH_{14}CO_3$ into an acid-stable product, as described previously (Diacovich, Peir et al. 2002). The total lipid were extracted from the lyophilized cell pellets using the reported method (Gu, Valianpour et al. 2004). The putative FAEEs in the total lipid were purified by preparative TLC and detected by GC-MS (Kalscheuer, Luftmann et al. 2004).

REFERENCES

Chirala, S. S., Q. Zhong, et al. (1994). “Analysis of FAS3/ACC regulatory region of *Saccharomyces cerevisiae*: identification of a functional UASINO and sequences responsible for fatty acid mediated repression.” Nucl. Acids Res. 22(3): 412-418.

Gu. Z., F. Valianpour, et al. (2004). "Aberrant cardiolipin metabolism in the yeast taz1 mutant: a model for Barth syndrome." Molecular Microbiology 51(1): 149-158.

Kalscheuer, R., H. Luftmann, et al. (2004). "Synthesis of Novel Lipids in *Saccharomyces cerevisiae* by Heterologous Expression of an Unspecific Bacterial Acyltransferase." Appl. Environ. Microbiol. 70(12): 7119-7125.

Kalscheuer, R., T. Stolting, et al. (2006). "Microdiesel: *Escherichia coli* engineered for fuel production." Microbiology 152(9): 2529-2536.

Sandager, L., M. Gustavsson, et al. (2002). "Storage lipid synthesis is non-essential in yeast." Journal of Biological Chemistry 277(8): 6478.

Shirra, M. K., J. Patton-Vogt, et al. (2001). "Inhibition of Acetyl Coenzyme A Carboxylase Activity Restores Expression of the INO1 Gene in a snf1 Mutant Strain of *Saccharomyces cerevisiae*." Mol. Cell. Biol. 21(17): 5710-5722.

Slocombe, S. P., J. Cornah, et al. (2009). "Oil accumulation in leaves directed by modification of fatty acid breakdown and lipid synthesis pathways." Plant Biotechnology Journal 7(7): 694-703.

Steen, E., Y. Kang, et al. (2010). "Microbial production of fatty-acid-derived fuels and chemicals from plant biomass." Nature 463(7280): 559-562.

Pighin, J. A., H. Zheng, et al. (2004). "Plant Cuticular Lipid Export Requires an ABC Transporter." Science 306 (5696): 702-704.

Diacovich, L., S. Peir, et al. (2002). "Kinetic and structural analysis of a new group of acyl-CoA carboxylases found in *Streptomyces coelicolor* A3 (2)." Journal of Biological Chemistry 277(34): 31228.

Gu, Z., F. Valianpour, et al. (2004). "Aberrant cardiolipin metabolism in the yeast taz1 mutant: a model for Barth syndrome." Molecular Microbiology 51(1): 149-158.

Hou, J., G. Vemuri, et al. (2009). "Impact of overexpressing NADH kinase on glucose and xylose metabolism in recombinant xylose-utilizing *Saccharomyces cerevisiae*." Applied microbiology and biotechnology 82(5): 909-919.

Kalscheuer, R., H. Luftmann, et al. (2004). "Synthesis of Novel Lipids in *Saccharomyces cerevisiae* by Heterologous Expression of an Unspecific Bacterial Acyltransferase." Appl. Environ. Microbiol. 70(12): 7119-7125.

Sambrook, J. and D. W. Russell (2001). "Molecular Cloning: A Laboratory Manual, thirded. Cold Spring Harbor Laboratory Press, Cold Spring Harbor, N.Y.".

Wang, X., Z. Wang, et al. (1996). "G418 selection and stability of cloned genes integrated at chromosomal delta sequences of *Saccharomyces cerevisiae*." Biotechnology and Bioengineering 49(1): 45-51.

Xiao, W. (2006). Yeast Protocols, Humana Press, Totowa, N.J.

S. Partow; V. Siewers; S. Bjørn: J. Nielsen; J. Maury (2010) Characterization of different promoters for designing a new expression vector in *Saccharomyces cerevisiae*. Yeast 27:955-964

Van Dijken, J. P., et al., 2000. An interlaboratory comparison of physiological and genetic properties of four *Saccharomyces cerevisiae* strains. Enzyme Microb. Technol. 26, 706-714.

The invention claimed is:

1. A fungal cell comprising an acetyl-CoA carboxylase gene, wherein the acetyl-CoA carboxylase gene is a mutated acetyl-CoA carboxylase gene encoding a mutated acetyl-CoA carboxylase comprising SEQ ID NO:16 having alanine at the position 659.

2. The fungal cell according to claim 1, further comprising:

overexpression of ACB1 (ACBP, acyl-CoA-binding protein);

overexpression of FAS1 (fatty acid synthase);

overexpression of FAS2 (fatty acid synthase);

heterologous expression of gapN (NADP+dependent glyceraldehyde-3-phosphate dehydrogenase); and/or overexpression of ACS1 (acetyl-CoA synthetase).

3. The fungal cell of claim 1, wherein the fungal cell produces fatty acids and/or fatty esters.

4. The fungal cell of claim 1, wherein the fungal cell is a yeast cell.

5. The fungal cell of claim 1, wherein the fungal cell is selected from the group of fungal cells consisting of *Saccharomyces; Saccharomyces cerevisiae; Hansenula polymorpha; Kluyveromyces; Pichia; Candida albicans*; Aspergilli; *Rhodotorula rubra;*

*Torulopsis; Trichosporon cutaneum; Trichoderma reesei; Apiofrichum curvafum; Yarrowia lipolytica*; and *Cryptococcus curvatus.*

6. The fungal cell of claim 2, wherein the fungal cell is selected from the group of fungal cells consisting of *Saccharomyces; Saccharomyces cerevisiae; Hansenula polymorpha; Kluyveromyces; Pichia; Candida albicans*; Aspergilli; *Rhodotorula rubra;*

*Torulopsis; Trichosporon cutaneum; Trichoderma reesei; Apiofrichum curvafum; Yarrowia lipolytica*; and *Cryptococcus curvatus.*

7. The fungal cell of claim 1, wherein the fungal cell uses supplied carbohydrates as an external substrate, wherein the supplied carbohydrates are selected from the group consisting of glucose, fructose, galactose, xylose, arabinose, sucrose, maltose, starch, cellulose, and hemicellulose.

8. A method for producing fatty acids and/or fatty acid derived products, the method comprising:

a) providing a fungal cell of claim 1;

b) adding one or more sources of carbohydrates as an external substrate to said fungal cell in a culture broth; and c) retrieving the fatty acids and/or fatty acid derived products by extraction from the culture broth.

* * * * *

SEQUENCE LISTING

<160> NUMBER OF SEQ ID NOS: 35

<210> SEQ ID NO 1
<211> LENGTH: 1377
<212> TYPE: DNA
<213> ORGANISM: Artificial sequence
<220> FEATURE:
<223> OTHER INFORMATION: Artificial Sequence, optimized from wax synthase of Acinetobacter baylyi ADP1

<400> SEQUENCE: 1

```
atgcgtccat tacatccaat tgatttcatc ttcctatctt tagaaaagag acagcaacca     60

atgcatgtag gcgggctttt tctcttccaa attcctgaca atgctccaga cacattcatc    120

caagacttgg ttaatgatat cagaatttcc aagtcaatac ctgttccacc tttcaataac    180

aaactcaacg gcttgttctg ggacgaggat gaagagttcg atctggatca tcactttcga    240

catatcgcat taccacaccc tggtagaatc agggagttac tcatctacat ttcccaagag    300

cattcaacat tacttgatag agccaagcca ttgtggacat gcaacataat cgaaggtata    360

gaaggcaata gatttgccat gtacttcaag atacatcacg ctatggttga tggagtcgct    420

ggaatgagac taatcgagaa gagcctttct cacgatgtta cagaaaagtc aattgtacca    480

ccttggtgtg tagaaggtaa acgagctaag cgtttacgtg aaccaaaaac cggaaagatc    540

aaaaagatta tgtctggtat caaatctcaa cttcaagcca cgcctactgt cattcaagag    600

ttgtctcaaa cagtgttcaa agacattggt agaaacccag atcacgtgtc ctcatttcaa    660

gcgccatgtt ctattctgaa ccaaagagta tccagtagta gaagatttgc agcacagtct    720

tttgatcttg ataggttcag aaacattgca aagtctctga acgtcaccat aaacgacgtg    780

gttctagctg tttgctctgg ggcactgaga gcttatctaa tgtcacataa cagcttgcca    840
```

```
tcaaaaccat tgattgcgat ggttcctgcc tctatacgta atgatgattc agatgtcagt    900

aacagaataa caatgatcct tgccaaccta gctactcata aggatgatcc tttgcagaga    960

ttagaaatca ttagaagatc agtgcaaaac tcaaagcaga gattcaaaag gatgaccagt   1020

gatcaaatct tgaattactc tgcagtggta tacggtccag ctggtctgaa tatcatatca   1080

ggaatgatgc caaaaagaca agcctttaac ttagttatct ccaatgtacc tggtccacga   1140

gaacctctct actggaacgg agctaagttg gatgcacttt acccagcctc tatcgtttta   1200

gatggtcagg ctttgaacat tacaatgact agttatctag acaagctaga agttgggttg   1260

attgcgtgta gaaatgccct acctagaatg cagaatttgc tgactcactt agaagaggag   1320

attcaactct ttgaaggcgt catcgcaaaa caagaggata tcaaaactgc aaactaa      1377


<210> SEQ ID NO 2
<211> LENGTH: 27
<212> TYPE: DNA
<213> ORGANISM: Artificial sequence
<220> FEATURE:
<223> OTHER INFORMATION: primer

<400> SEQUENCE: 2

cgggatcccg ctcgagatgc gtccatt                                         27


<210> SEQ ID NO 3
<211> LENGTH: 30
<212> TYPE: DNA
<213> ORGANISM: Artificial sequence
<220> FEATURE:
<223> OTHER INFORMATION: primer

<400> SEQUENCE: 3

ggggtacccc aagcttgggt tagtttgcag                                      30


<210> SEQ ID NO 4
<211> LENGTH: 1422
<212> TYPE: DNA
<213> ORGANISM: Artificial sequence
<220> FEATURE:
<223> OTHER INFORMATION: Artificial Sequence, optimized from wax
      synthase of Marinobacter hydrocarbonoclasticus DSM 8798

<400> SEQUENCE: 4

atgaagagat taggtactct agacgctagt tggcttgcag tcgaatccga agatacgcca     60

atgcacgtgg gcactctcca aatcttctca ttaccagaag gtgctccaga gacatttcta    120

cgtgatatgg ttacaaggat gaaagaggca ggagatgttg ccccaccatg ggggttacaag    180

ctcgcatggt ccggtttcct tggcagggtt attgctcctg cctggaaggt agacaaagat    240

atcgatttgg attatcatgt ccgacatagt gcattgccaa gaccaggtgg tgaaagagag    300

ctagggatac ttgtttctag attacactcc aaccctttag atttctctag accactatgg    360

gaatgccatg tcattgaagg tcttgaaaac aacagatttg cactgtatac taagatgcat    420

cactctatga ttgatgggat atctggagta agattgatgc aaagagtatt gaccactgac    480

ccagagagat gtaacatgcc tcctccatgg acagttagac ctcaccagag aagaggagct    540

aaaacagata aagaggcttc tgtgcctgct gcggtttctc aagcaatgga cgccttgaag    600

ctccaagcgg atatggcccc tagactatgg caagctggca atcgtctagt acattctgtc    660

agacaccctg aggatggctt aacagctcca ttcaccggtc cagtgtctgt ccttaaccat    720

agagttacag cgcagagaag attcgctact caacactacc aactagatag attgaaaaac    780
```

```
ttagcgcatg ccagtggtgg ttcactgaat gatatagtgc tttacttatg tggtactgcc    840

ttgagaaggt ttttggctga gcagaataac ttgcctgaca cacctttaac ggcaggaatt    900

ccagtgaata tcagaccagc tgatgacgaa ggcaccggaa cacaaatctc attcatgatt    960

gctagtttgg ctactgacga agctgatcct ctcaatagat tacaacagat caaaacctca   1020

acacgaaggg cgaaggagca tctccaaaag ttgcctaagt cagcactaac acaatacaca   1080

atgctgctga tgtcacctta catcttacaa ttgatgagcg gattgggagg tagaatgagg   1140

ccagttttca atgttactat aagcaatgtc cctgggcctg aggggacatt gtattacgaa   1200

ggagctagat tggaagccat gtacccagtt tcccttatcg cccacggtgg tgccttgaac   1260

atcacatgcc tgtcttacgc tggctccctt aactttgggt ttaccggttg tcgtgatact   1320

ttaccatcaa tgcaaaagtt agcagtctat actggtgaag cattggatga actcgaatct   1380

ctaattctgc caccaaagaa gcgtgcccgt actagaaagt aa                     1422
```

```
<210> SEQ ID NO 5
<211> LENGTH: 1422
<212> TYPE: DNA
<213> ORGANISM: Artificial sequence
<220> FEATURE:
<223> OTHER INFORMATION: Artificial Sequence, optimized from wax
      synthase of Rhodococcus opacus PD630

<400> SEQUENCE: 5
```

```
ttgaccgacg tgattaccac aaaccaaaga tacatgactc agaccgattt catgtcttgg     60

agaatggagg aagatccaat actgagaagc acgatcgttg cagtggccct gttggacaga    120

aggcctgatc aaagtagatt tgttgatatg atgagaagag ctgtcgatct agttccattg    180

tttcgtagaa ccgccattga agatccactc ggcttggctc ctccaagatg ggccgatgat    240

agagattttg acctatcatg gcatctaaga cgatatactt tagcggaacc taggacttgg    300

gacggcgtcc tagatttcgc acgtactgca gagatgacag cttttgataa acgtagacct    360

ttgtgggagt tcacaatctt agatggtctt aatgatggta gatcagcgtt ggttatgaag    420

gttcaccatt cactcacgga tggtgtctct ggtatgcaaa ttgccagaga aatcgtggac    480

tttactagag aaggtacgcc acgaccagga cgtacagata gagctacagc tgttcctcat    540

ggaggctctt ctagacctcc ttctagactt agttggtata gagatacagc tgcagacgta    600

acacaccgag ctgcgaacat cttgggtaga aattctgtta ggctagttag agcgccacgt    660

gctacatgga gagaagccac tgcgttagct ggttccactt taagattaac cagaccagtt    720

gtttccacat tgtcaccagt gatgactaag agatcaacaa gacgacattg tgctgtcatc    780

gacgtccctg tagaagctct cgcacaggct gcagcagccg cagctgggtc tatcaatgac    840

gctttccttg ctgcagtcct gttgggtatg gcaaagtacc atagacttca tggtgccgaa    900

atcagagaat tacgtatgac tttaccaata tctttaagga cagaaacaga tccattaggt    960

gggaatagaa tttccctagc cagattcgct ttgcctactg atattgatga tccagctgag   1020

ttgatgagga gggtacacgc tactgtagat gcatggagaa gagaaccagc aataccattt   1080

tcccctatga ttgctggtgc cgtaaactta cttcctgcct caactttagg gaacatgttg   1140

aaacacgttg actttgtagc atctaacgtc gctggctcac cagttcctct attcatagcc   1200

ggatcagaga tcctacatta ctacgcgttc tcaccaactc ttggatctgc attcaatgtt   1260

acgctgatga gttacaccac tcaatgctgt gtcgggataa acgctgatac agacgctgta   1320

cctgatcttg ccacactgac cgaaagtttg gcagatggat tcagagccgt tttgggctta   1380
```

```
tgtgctaaga ctacagacac aagagtggtg gtggctagct aa                    1422

<210> SEQ ID NO 6
<211> LENGTH: 1002
<212> TYPE: DNA
<213> ORGANISM: Artificial sequence
<220> FEATURE:
<223> OTHER INFORMATION: Artificial Sequence, optimized from wax
      synthase of Mus musculus C57BL/6

<400> SEQUENCE: 6

atgttctggc caaccaaaaa ggatttgaaa actgcaatgg aagtatttgc tctcttccaa     60

tgggcccttt ccgctttggt aattgtcact actgtgatca tagtcaattt gtatcttgtt    120

gtgtttacat catattggcc agtgacggtc ttaatgttga catggttagc attcgattgg    180

aaaacaccag aaagaggtgg caggagattc acatgtgtcc gtaagtggag attgtggaag    240

cactactctg attacttccc tttgaaaatg gttaagacta aggacatatc accagataga    300

aactacatct tagtatgtca tccacatggt cttatggcac attcatgttt cggacatttc    360

gccacagata caactggatt cagtaagact tttcctggta tcactcctta catgctaaca    420

ttaggcgcct tttctgggt tccattcctt agagactatg ttatgtccac tggctcatgc    480

tctgtgtcca gaagctcaat ggacttcctc ctaacacaaa aaggaactgg aaacatgttg    540

gttgtagttg taggtggttt agctgagtgt cgttactcta cgccaggctc tacaaccctg    600

tttttgaaaa agagacaggg tttcgtgaga actgcgttga agcatggtgt ttctctgatc    660

ccagcttacg ctttcgggga aactgatctc tacgatcaac acatattcac accaggtggt    720

tttgtcaata gatttcagaa atggtttcaa aagatggtac acatctaccc atgcgctttc    780

tatggcagag ggctcaccaa aaactcatgg gggctactac cttattcaca gcctgttacc    840

acagtggttg gagaaccttt acctctgcca aagattgaaa acccttccga agagattgtt    900

gcgaagtacc atacactgta catcgatgca cttaggaagc tattcgacca acacaaaact    960

aagtttggta ttagtgaaac ccaagagttg gtcattgttt aa                    1002

<210> SEQ ID NO 7
<211> LENGTH: 1428
<212> TYPE: DNA
<213> ORGANISM: Artificial sequence
<220> FEATURE:
<223> OTHER INFORMATION: Artificial Sequence, optimized from wax
      synthase of Psychrobacter articus 273-4

<400> SEQUENCE: 7

atgagattac tgaccgctgt cgatcaactc tttctattgt tggagagtag aaagcaccca     60

atgcacgttg gtggactgtt cctattcgag cttccagaga atgctgacat tagtttcgtt    120

caccagcttg ttaagcaaat gcaagattcc gacgtaccac caacattccc attcaatcag    180

gttctggaac acatgatgtt ttggaaggag gacaaaaact ttgacgtaga acatcatcta    240

caccatgtgg ctttaccaaa acctgccaga gttagagaat tactcatgta cgtttccagg    300

gaacatggga ggttgctcga tagagcaatg ccactatggg agtgccatgt gatcgaaggt    360

attcaaccag agactgaagg ttctccagag agattcgcat tgtatttcaa gattcatcat    420

tccttagtcg atggtatcgc cgctatgagg ttggtgaaaa agtcattatc acagtcacca    480

aacgaaccag ttacccttcc aatctggtct ttgatggctc accatagaaa ccaaatcgat    540

gccatcttcc caaaggaaag atcagccttg cgtatcttaa aggaacaagt ttctacaatc    600
```

```
aagcctgtgt ttactgaact cttgaataac ttcaaaaact acaatgacga tagttacgtc    660

agcacttttg acgctcctag atcaatcctt aaccgtagaa tttctgcctc aagacgtatt    720

gcagcgcagt catacgatat caaaagattc aatgacatag cggagagaat caacatttcc    780

aaaaacgatg tggttttggc agtatgttcc ggtgctatta gaagatacct tatctctatg    840

gatgctttac catcaaaacc tctgatagca ttcgttccta tgtctttgcg aactgatgat    900

agtatagctg gaaaccaatt gagttttgta ctagcgaatc tgggcacaca tttggatgat    960

ccattatcta gaatcaagct cattcatcgt agcatgaaca actctaagag aagattcaga   1020

aggatgaacc aagcacaagt tatcaattac tccatagtat cttacgcatg ggaaggcatt   1080

aacttggcca ctgatctttt ccctaaaaag caagccttta acttaatcat ctctaacgtc   1140

ccaggctcag aaaaaccttt gtattggaat ggtgcaagat tagaatcact atatcctgct   1200

tcaatcgtgt ttaacggaca agctatgaat atcacgcttg catcttactt ggacaagatg   1260

gaattcggta taactgcttg ttctaaagct ctacctcatg tccaagatat gttgatgctt   1320

attgaggaag agctacaact gctggaatct gttagcaagg aactagaatt caatgggatt   1380

acagtaaaag ataagtcaga gaaaaagctg aaaaagttgg cccccttaa               1428
```

<210> SEQ ID NO 8
<211> LENGTH: 30
<212> TYPE: DNA
<213> ORGANISM: Artificial sequence
<220> FEATURE:
<223> OTHER INFORMATION: primer

<400> SEQUENCE: 8

```
cgggatcccg ctcgagatga agagattagg                                      30
```

<210> SEQ ID NO 9
<211> LENGTH: 34
<212> TYPE: DNA
<213> ORGANISM: Artificial sequence
<220> FEATURE:
<223> OTHER INFORMATION: primer

<400> SEQUENCE: 9

```
ggggtacccc aagcttgggt tactttctag tacg                                 34
```

<210> SEQ ID NO 10
<211> LENGTH: 33
<212> TYPE: DNA
<213> ORGANISM: Artificial sequence
<220> FEATURE:
<223> OTHER INFORMATION: primer

<400> SEQUENCE: 10

```
cgggatcccg ctcgagttga ccgacgtgat tac                                  33
```

<210> SEQ ID NO 11
<211> LENGTH: 35
<212> TYPE: DNA
<213> ORGANISM: Artificial sequence
<220> FEATURE:
<223> OTHER INFORMATION: primer

<400> SEQUENCE: 11

```
ggggtacccc aagcttgggt tagctagcca ccacc                                35
```

<210> SEQ ID NO 12
<211> LENGTH: 31

<212> TYPE: DNA
<213> ORGANISM: Artificial sequence
<220> FEATURE:
<223> OTHER INFORMATION: primer

<400> SEQUENCE: 12
cgggatcccg ctcgagatgt tctggccaac c 31

<210> SEQ ID NO 13
<211> LENGTH: 35
<212> TYPE: DNA
<213> ORGANISM: Artificial sequence
<220> FEATURE:
<223> OTHER INFORMATION: primer

<400> SEQUENCE: 13
ggggtacccc aagcttgggt taaacaatga ccaac 35

<210> SEQ ID NO 14
<211> LENGTH: 36
<212> TYPE: DNA
<213> ORGANISM: Artificial sequence
<220> FEATURE:
<223> OTHER INFORMATION: primer

<400> SEQUENCE: 14
cgggatcccg ctcgagatga gattactgac cgctgt 36

<210> SEQ ID NO 15
<211> LENGTH: 33
<212> TYPE: DNA
<213> ORGANISM: Artificial sequence
<220> FEATURE:
<223> OTHER INFORMATION: primer

<400> SEQUENCE: 15
ggggtacccc aagcttgggt taaggggcca act 33

<210> SEQ ID NO 16
<211> LENGTH: 2233
<212> TYPE: PRT
<213> ORGANISM: Artificial sequence
<220> FEATURE:
<223> OTHER INFORMATION: modified ACC1 gene

<400> SEQUENCE: 16

```
Met Ser Glu Glu Ser Leu Phe Glu Ser Ser Pro Gln Lys Met Glu Tyr
1               5                   10                  15

Glu Ile Thr Asn Tyr Ser Glu Arg His Thr Glu Leu Pro Gly His Phe
            20                  25                  30

Ile Gly Leu Asn Thr Val Asp Lys Leu Glu Glu Ser Pro Leu Arg Asp
        35                  40                  45

Phe Val Lys Ser His Gly Gly His Thr Val Ile Ser Lys Ile Leu Ile
    50                  55                  60

Ala Asn Asn Gly Ile Ala Ala Val Lys Glu Ile Arg Ser Val Arg Lys
65                  70                  75                  80

Trp Ala Tyr Glu Thr Phe Gly Asp Asp Arg Thr Val Gln Phe Val Ala
                85                  90                  95

Met Ala Thr Pro Glu Asp Leu Glu Ala Asn Ala Glu Tyr Ile Arg Met
            100                 105                 110

Ala Asp Gln Tyr Ile Glu Val Pro Gly Gly Thr Asn Asn Asn Asn Tyr
        115                 120                 125
```

```
Ala Asn Val Asp Leu Ile Val Asp Ile Ala Glu Arg Ala Asp Val Asp
    130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
            180                 185                 190

Ala Gln Ser Ala Lys Val Pro Cys Ile Pro Trp Ser Gly Thr Gly Val
        195                 200                 205

Asp Thr Val His Val Asp Glu Lys Thr Gly Leu Val Ser Val Asp Asp
    210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
            260                 265                 270

Ala Leu Tyr His Gln Ala Ala Asn Glu Ile Pro Gly Ser Pro Ile Phe
        275                 280                 285

Ile Met Lys Leu Ala Gly Arg Ala Arg His Leu Glu Val Gln Leu Leu
    290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

Ala Lys Ala Glu Thr Phe His Glu Met Glu Lys Ala Ala Val Arg Leu
            340                 345                 350

Gly Lys Leu Val Gly Tyr Val Ser Ala Gly Thr Val Glu Tyr Leu Tyr
        355                 360                 365

Ser His Asp Asp Gly Lys Phe Tyr Phe Leu Glu Leu Asn Pro Arg Leu
    370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
                405                 410                 415

Asp Ile Arg Thr Leu Tyr Gly Met Asn Pro His Ser Ala Ser Glu Ile
            420                 425                 430

Asp Phe Glu Phe Lys Thr Gln Asp Ala Thr Lys Lys Gln Arg Arg Pro
        435                 440                 445

Ile Pro Lys Gly His Cys Thr Ala Cys Arg Ile Thr Ser Glu Asp Pro
    450                 455                 460

Asn Asp Gly Phe Lys Pro Ser Gly Gly Thr Leu His Glu Leu Asn Phe
465                 470                 475                 480

Arg Ser Ser Ser Asn Val Trp Gly Tyr Phe Ser Val Gly Asn Asn Gly
                485                 490                 495

Asn Ile His Ser Phe Ser Asp Ser Gln Phe Gly His Ile Phe Ala Phe
            500                 505                 510

Gly Glu Asn Arg Gln Ala Ser Arg Lys His Met Val Val Ala Leu Lys
        515                 520                 525

Glu Leu Ser Ile Arg Gly Asp Phe Arg Thr Thr Val Glu Tyr Leu Ile
    530                 535                 540

Lys Leu Leu Glu Thr Glu Asp Phe Glu Asp Asn Thr Ile Thr Thr Gly
```

-continued

```
545                 550                 555                 560

Trp Leu Asp Asp Leu Ile Thr His Lys Met Thr Ala Glu Lys Pro Asp
                565                 570                 575

Pro Thr Leu Ala Val Ile Cys Gly Ala Ala Thr Lys Ala Phe Leu Ala
            580                 585                 590

Ser Glu Glu Ala Arg His Lys Tyr Ile Glu Ser Leu Gln Lys Gly Gln
        595                 600                 605

Val Leu Ser Lys Asp Leu Leu Gln Thr Met Phe Pro Val Asp Phe Ile
    610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
                645                 650                 655

Gln Leu Ala Asp Gly Gly Leu Leu Ile Ala Ile Gly Gly Lys Ser His
            660                 665                 670

Thr Ile Tyr Trp Lys Glu Glu Val Ala Ala Thr Arg Leu Ser Val Asp
        675                 680                 685

Ser Met Thr Thr Leu Leu Glu Val Glu Asn Asp Pro Thr Gln Leu Arg
    690                 695                 700

Thr Pro Ser Pro Gly Lys Leu Val Lys Phe Leu Val Glu Asn Gly Glu
705                 710                 715                 720

His Ile Ile Lys Gly Gln Pro Tyr Ala Glu Ile Glu Val Met Lys Met
                725                 730                 735

Gln Met Pro Leu Val Ser Gln Glu Asn Gly Ile Val Gln Leu Leu Lys
            740                 745                 750

Gln Pro Gly Ser Thr Ile Val Ala Gly Asp Ile Met Ala Ile Met Thr
        755                 760                 765

Leu Asp Asp Pro Ser Lys Val Lys His Ala Leu Pro Phe Glu Gly Met
    770                 775                 780

Leu Pro Asp Phe Gly Ser Pro Val Ile Glu Gly Thr Lys Pro Ala Tyr
785                 790                 795                 800

Lys Phe Lys Ser Leu Val Ser Thr Leu Glu Asn Ile Leu Lys Gly Tyr
                805                 810                 815

Asp Asn Gln Val Ile Met Asn Ala Ser Leu Gln Gln Leu Ile Glu Val
            820                 825                 830

Leu Arg Asn Pro Lys Leu Pro Tyr Ser Glu Trp Lys Leu His Ile Ser
        835                 840                 845

Ala Leu His Ser Arg Leu Pro Ala Lys Leu Asp Glu Gln Met Glu Glu
    850                 855                 860

Leu Val Ala Arg Ser Leu Arg Arg Gly Ala Val Phe Pro Ala Arg Gln
865                 870                 875                 880

Leu Ser Lys Leu Ile Asp Met Ala Val Lys Asn Pro Glu Tyr Asn Pro
                885                 890                 895

Asp Lys Leu Leu Gly Ala Val Val Glu Pro Leu Ala Asp Ile Ala His
            900                 905                 910

Lys Tyr Ser Asn Gly Leu Glu Ala His Glu His Ser Ile Phe Val His
        915                 920                 925

Phe Leu Glu Glu Tyr Tyr Glu Val Glu Lys Leu Phe Asn Gly Pro Asn
    930                 935                 940

Val Arg Glu Glu Asn Ile Ile Leu Lys Leu Arg Asp Glu Asn Pro Lys
945                 950                 955                 960

Asp Leu Asp Lys Val Ala Leu Thr Val Leu Ser His Ser Lys Val Ser
                965                 970                 975
```

```
Ala Lys Asn Asn Leu Ile Leu Ala Ile Leu Lys His Tyr Gln Pro Leu
            980                 985                 990

Cys Lys Leu Ser Ser Lys Val Ser  Ala Ile Phe Ser Thr  Pro Leu Gln
        995                 1000                1005

His Ile  Val Glu Leu Glu Ser  Lys Ala Thr Ala Lys  Val Ala Leu
    1010                 1015                 1020

Gln Ala  Arg Glu Ile Leu Ile  Gln Gly Ala Leu Pro  Ser Val Lys
    1025                 1030                 1035

Glu Arg  Thr Glu Gln Ile Glu  His Ile Leu Lys Ser  Ser Val Val
    1040                 1045                 1050

Lys Val  Ala Tyr Gly Ser Ser  Asn Pro Lys Arg Ser  Glu Pro Asp
    1055                 1060                 1065

Leu Asn  Ile Leu Lys Asp Leu  Ile Asp Ser Asn Tyr  Val Val Phe
    1070                 1075                 1080

Asp Val  Leu Leu Gln Phe Leu  Thr His Gln Asp Pro  Val Val Thr
    1085                 1090                 1095

Ala Ala  Ala Ala Gln Val Tyr  Ile Arg Arg Ala Tyr  Arg Ala Tyr
    1100                 1105                 1110

Thr Ile  Gly Asp Ile Arg Val  His Glu Gly Val Thr  Val Pro Ile
    1115                 1120                 1125

Val Glu  Trp Lys Phe Gln Leu  Pro Ser Ala Ala Phe  Ser Thr Phe
    1130                 1135                 1140

Pro Thr  Val Lys Ser Lys Met  Gly Met Asn Arg Ala  Val Ala Val
    1145                 1150                 1155

Ser Asp  Leu Ser Tyr Val Ala  Asn Ser Gln Ser Ser  Pro Leu Arg
    1160                 1165                 1170

Glu Gly  Ile Leu Met Ala Val  Asp His Leu Asp Asp  Val Asp Glu
    1175                 1180                 1185

Ile Leu  Ser Gln Ser Leu Glu  Val Ile Pro Arg His  Gln Ser Ser
    1190                 1195                 1200

Ser Asn  Gly Pro Ala Pro Asp  Arg Ser Gly Ser Ser  Ala Ser Leu
    1205                 1210                 1215

Ser Asn  Val Ala Asn Val Cys  Val Ala Ser Thr Glu  Gly Phe Glu
    1220                 1225                 1230

Ser Glu  Glu Glu Ile Leu Val  Arg Leu Arg Glu Ile  Leu Asp Leu
    1235                 1240                 1245

Asn Lys  Gln Glu Leu Ile Asn  Ala Ser Ile Arg Arg  Ile Thr Phe
    1250                 1255                 1260

Met Phe  Gly Phe Lys Asp Gly  Ser Tyr Pro Lys Tyr  Tyr Thr Phe
    1265                 1270                 1275

Asn Gly  Pro Asn Tyr Asn Glu  Asn Glu Thr Ile Arg  His Ile Glu
    1280                 1285                 1290

Pro Ala  Leu Ala Phe Gln Leu  Glu Leu Gly Arg Leu  Ser Asn Phe
    1295                 1300                 1305

Asn Ile  Lys Pro Ile Phe Thr  Asp Asn Arg Asn Ile  His Val Tyr
    1310                 1315                 1320

Glu Ala  Val Ser Lys Thr Ser  Pro Leu Asp Lys Arg  Phe Phe Thr
    1325                 1330                 1335

Arg Gly  Ile Ile Arg Thr Gly  His Ile Arg Asp Asp  Ile Ser Ile
    1340                 1345                 1350

Gln Glu  Tyr Leu Thr Ser Glu  Ala Asn Arg Leu Met  Ser Asp Ile
    1355                 1360                 1365
```

```
Leu Asp  Asn Leu Glu Val Thr  Asp Thr Ser Asn Ser  Asp Leu Asn
    1370                 1375                 1380

His Ile  Phe Ile Asn Phe Ile  Ala Val Phe Asp Ile  Ser Pro Glu
    1385                 1390                 1395

Asp Val  Glu Ala Ala Phe Gly  Gly Phe Leu Glu Arg  Phe Gly Lys
    1400                 1405                 1410

Arg Leu  Leu Arg Leu Arg Val  Ser Ser Ala Glu Ile  Arg Ile Ile
    1415                 1420                 1425

Ile Lys  Asp Pro Gln Thr Gly  Ala Pro Val Pro Leu  Arg Ala Leu
    1430                 1435                 1440

Ile Asn  Asn Val Ser Gly Tyr  Val Ile Lys Thr Glu  Met Tyr Thr
    1445                 1450                 1455

Glu Val  Lys Asn Ala Lys Gly  Glu Trp Val Phe Lys  Ser Leu Gly
    1460                 1465                 1470

Lys Pro  Gly Ser Met His Leu  Arg Pro Ile Ala Thr  Pro Tyr Pro
    1475                 1480                 1485

Val Lys  Glu Trp Leu Gln Pro  Lys Arg Tyr Lys Ala  His Leu Met
    1490                 1495                 1500

Gly Thr  Thr Tyr Val Tyr Asp  Phe Pro Glu Leu Phe  Arg Gln Ala
    1505                 1510                 1515

Ser Ser  Ser Gln Trp Lys Asn  Phe Ser Ala Asp Val  Lys Leu Thr
    1520                 1525                 1530

Asp Asp  Phe Phe Ile Ser Asn  Glu Leu Ile Glu Asp  Glu Asn Gly
    1535                 1540                 1545

Glu Leu  Thr Glu Val Glu Arg  Glu Pro Gly Ala Asn  Ala Ile Gly
    1550                 1555                 1560

Met Val  Ala Phe Lys Ile Thr  Val Lys Thr Pro Glu  Tyr Pro Arg
    1565                 1570                 1575

Gly Arg  Gln Phe Val Val Val  Ala Asn Asp Ile Thr  Phe Lys Ile
    1580                 1585                 1590

Gly Ser  Phe Gly Pro Gln Glu  Asp Glu Phe Phe Asn  Lys Val Thr
    1595                 1600                 1605

Glu Tyr  Ala Arg Lys Arg Gly  Ile Pro Arg Ile Tyr  Leu Ala Ala
    1610                 1615                 1620

Asn Ser  Gly Ala Arg Ile Gly  Met Ala Glu Glu Ile  Val Pro Leu
    1625                 1630                 1635

Phe Gln  Val Ala Trp Asn Asp  Ala Ala Asn Pro Asp  Lys Gly Phe
    1640                 1645                 1650

Gln Tyr  Leu Tyr Leu Thr Ser  Glu Gly Met Glu Thr  Leu Lys Lys
    1655                 1660                 1665

Phe Asp  Lys Glu Asn Ser Val  Leu Thr Glu Arg Thr  Val Ile Asn
    1670                 1675                 1680

Gly Glu  Glu Arg Phe Val Ile  Lys Thr Ile Ile Gly  Ser Glu Asp
    1685                 1690                 1695

Gly Leu  Gly Val Glu Cys Leu  Arg Gly Ser Gly Leu  Ile Ala Gly
    1700                 1705                 1710

Ala Thr  Ser Arg Ala Tyr His  Asp Ile Phe Thr Ile  Thr Leu Val
    1715                 1720                 1725

Thr Cys  Arg Ser Val Gly Ile  Gly Ala Tyr Leu Val  Arg Leu Gly
    1730                 1735                 1740

Gln Arg  Ala Ile Gln Val Glu  Gly Gln Pro Ile Ile  Leu Thr Gly
    1745                 1750                 1755

Ala Pro  Ala Ile Asn Lys Met  Leu Gly Arg Glu Val  Tyr Thr Ser
```

```
    1760                1765                1770

Asn Leu  Gln Leu Gly Gly Thr  Gln Ile Met Tyr Asn  Asn Gly Val
    1775                1780                1785

Ser His  Leu Thr Ala Val Asp  Asp Leu Ala Gly Val  Glu Lys Ile
    1790                1795                1800

Val Glu  Trp Met Ser Tyr Val  Pro Ala Lys Arg Asn  Met Pro Val
    1805                1810                1815

Pro Ile  Leu Glu Thr Lys Asp  Thr Trp Asp Arg Pro  Val Asp Phe
    1820                1825                1830

Thr Pro  Thr Asn Asp Glu Thr  Tyr Asp Val Arg Trp  Met Ile Glu
    1835                1840                1845

Gly Arg  Glu Thr Glu Ser Gly  Phe Glu Tyr Gly Leu  Phe Asp Lys
    1850                1855                1860

Gly Ser  Phe Phe Glu Thr Leu  Ser Gly Trp Ala Lys  Gly Val Val
    1865                1870                1875

Val Gly  Arg Ala Arg Leu Gly  Gly Ile Pro Leu Gly  Val Ile Gly
    1880                1885                1890

Val Glu  Thr Arg Thr Val Glu  Asn Leu Ile Pro Ala  Asp Pro Ala
    1895                1900                1905

Asn Pro  Asn Ser Ala Glu Thr  Leu Ile Gln Glu Pro  Gly Gln Val
    1910                1915                1920

Trp His  Pro Asn Ser Ala Phe  Lys Thr Ala Gln Ala  Ile Asn Asp
    1925                1930                1935

Phe Asn  Asn Gly Glu Gln Leu  Pro Met Met Ile Leu  Ala Asn Trp
    1940                1945                1950

Arg Gly  Phe Ser Gly Gly Gln  Arg Asp Met Phe Asn  Glu Val Leu
    1955                1960                1965

Lys Tyr  Gly Ser Phe Ile Val  Asp Ala Leu Val Asp  Tyr Lys Gln
    1970                1975                1980

Pro Ile  Ile Ile Tyr Ile Pro  Pro Thr Gly Glu Leu  Arg Gly Gly
    1985                1990                1995

Ser Trp  Val Val Val Asp Pro  Thr Ile Asn Ala Asp  Gln Met Glu
    2000                2005                2010

Met Tyr  Ala Asp Val Asn Ala  Arg Ala Gly Val Leu  Glu Pro Gln
    2015                2020                2025

Gly Met  Val Gly Ile Lys Phe  Arg Arg Glu Lys Leu  Leu Asp Thr
    2030                2035                2040

Met Asn  Arg Leu Asp Asp Lys  Tyr Arg Glu Leu Arg  Ser Gln Leu
    2045                2050                2055

Ser Asn  Lys Ser Leu Ala Pro  Glu Val His Gln Gln  Ile Ser Lys
    2060                2065                2070

Gln Leu  Ala Asp Arg Glu Arg  Glu Leu Leu Pro Ile  Tyr Gly Gln
    2075                2080                2085

Ile Ser  Leu Gln Phe Ala Asp  Leu His Asp Arg Ser  Ser Arg Met
    2090                2095                2100

Val Ala  Lys Gly Val Ile Ser  Lys Glu Leu Glu Trp  Thr Glu Ala
    2105                2110                2115

Arg Arg  Phe Phe Phe Trp Arg  Leu Arg Arg Arg Leu  Asn Glu Glu
    2120                2125                2130

Tyr Leu  Ile Lys Arg Leu Ser  His Gln Val Gly Glu  Ala Ser Arg
    2135                2140                2145

Leu Glu  Lys Ile Ala Arg Ile  Arg Ser Trp Tyr Pro  Ala Ser Val
    2150                2155                2160
```

```
Asp His  Glu Asp Asp Arg Gln  Val Ala Thr Trp Ile  Glu Glu Asn
    2165                 2170                 2175

Tyr Lys  Thr Leu Asp Asp Lys  Leu Lys Gly Leu Lys  Leu Glu Ser
    2180                 2185                 2190

Phe Ala  Gln Asp Leu Ala Lys  Lys Ile Arg Ser Asp  His Asp Asn
    2195                 2200                 2205

Ala Ile  Asp Gly Leu Ser Glu  Val Ile Lys Met Leu  Ser Thr Asp
    2210                 2215                 2220

Asp Lys  Glu Lys Leu Leu Lys  Thr Leu Lys
    2225                 2230
```

<210> SEQ ID NO 17
<211> LENGTH: 1428
<212> TYPE: DNA
<213> ORGANISM: Artificial sequence
<220> FEATURE:
<223> OTHER INFORMATION: optimized gapN sequence

<400> SEQUENCE: 17

```
ttgacaaaac aatacaaaaa ctacgttaat ggtgaatgga aactaagtga gaatgaaatc     60

aagatatacg aacctgcctc aggcgcagaa ctgggttctg ttcctgcaat gtccactgag    120

gaagtggatt acgtgtatgc ttcagccaaa aaggctcagc ctgcatggag atccctaagt    180

tacattgaaa gagctgccta tttgcataaa gtcgcagaca tattgatgag ggataaagag    240

aagattggcg ctgtgctttc taaggaagtc gctaagggat acaaatctgc agtatctgag    300

gtagttagaa cagcagagat tatcaattac gctgccgagg aaggtcttag aatggaggga    360

gaggtacttg aaggaggatc atttgaagca gcatccaaaa agaagatcgc tgtagtaagg    420

agagaaccag taggccttgt tctagccatc agtcctttca actatccagt caacttagct    480

ggctccaaaa tcgctcctgc cttaatcgct ggtaatgtca ttgctttcaa gccacctact    540

caagggtcta tttcaggttt gttgttggcc gaggcttttg ctgaagcagg tctgccagct    600

ggtgttttca atacaattac aggtagagga tctgaaattg gagactacat tgtcgaacat    660

caagctgtca actttatcaa tttcacaggt tcaacaggaa ttggcgagag aatagggaaa    720

atggcaggta tgcgtccaat catgttagaa ctaggcggga aagactctgc aatcgtgttg    780

gaagatgctg atttggaact taccgccaaa aacatcattg ccggtgcatt cggttattct    840

ggacaaagat gtactgcagt taaacgtgtt ttagtaatgg aatcagtggc agatgaactt    900

gtggaaaaga tcagggaaaa agtccttgca ctgactatcg gtaatccaga agatgatgct    960

gacatcaccc cacttattga cactaagtca gctgattatg ttgaaggttt gatcaatgat   1020

gcaaatgata agggtgccgc tgccttaaca gagatcaaaa gagaaggtaa cttaatctgc   1080

ccaatcctgt ttgataaggt tactactgat atgagattgg cttgggagga accatttggt   1140

cctgttttgc ctatcataag agttacctct gttgaggaag ctatagagat atctaacaaa   1200

tcagaatacg gcttacaagc ctctatcttt actaatgatt tcccaagagc atttggaata   1260

gctgaacaac tagaagtagg tacagttcac attaacaaca aaacccagag aggcacagac   1320

aatttcccat ttctaggggc caaaaagtca ggggctggaa ttcaaggcgt gaaatactcc   1380

attgaagcta tgactacagt gaaaagtgtt gtctttgaca taaagtga                1428
```

<210> SEQ ID NO 18
<211> LENGTH: 30
<212> TYPE: DNA
<213> ORGANISM: Artificial sequence
<220> FEATURE:
<223> OTHER INFORMATION: primer

<400> SEQUENCE: 18
aaacaagcgg ccgcactagt ttgacaaaac 30

<210> SEQ ID NO 19
<211> LENGTH: 34
<212> TYPE: DNA
<213> ORGANISM: Artificial sequence
<220> FEATURE:
<223> OTHER INFORMATION: primer

<400> SEQUENCE: 19
ttaattaaga gctcagatct ttatttgata tcaa 34

<210> SEQ ID NO 20
<211> LENGTH: 30
<212> TYPE: DNA
<213> ORGANISM: Artificial sequence
<220> FEATURE:
<223> OTHER INFORMATION: primer

<400> SEQUENCE: 20
cgggatcccg ctcgagatga agagattagg 30

<210> SEQ ID NO 21
<211> LENGTH: 34
<212> TYPE: DNA
<213> ORGANISM: Artificial sequence
<220> FEATURE:
<223> OTHER INFORMATION: primer

<400> SEQUENCE: 21
ggggtacccc aagcttgggt tactttctag tacg 34

<210> SEQ ID NO 22
<211> LENGTH: 53
<212> TYPE: DNA
<213> ORGANISM: Artificial sequence
<220> FEATURE:
<223> OTHER INFORMATION: primer

<400> SEQUENCE: 22
gttgggattc cattgttgat aaaggcgcac acaccatagc ttcaaaatgt ttc 53

<210> SEQ ID NO 23
<211> LENGTH: 32
<212> TYPE: DNA
<213> ORGANISM: Artificial sequence
<220> FEATURE:
<223> OTHER INFORMATION: primer

<400> SEQUENCE: 23
gtgcaatgta gatcttcgag cgtcccaaaa cc 32

<210> SEQ ID NO 24
<211> LENGTH: 52
<212> TYPE: DNA
<213> ORGANISM: Artificial sequence
<220> FEATURE:
<223> OTHER INFORMATION: primer

<400> SEQUENCE: 24
gacgctcgaa gatctacatt gcacaagata aaaatatatc atcatgaaca at 52

<210> SEQ ID NO 25
<211> LENGTH: 43
<212> TYPE: DNA
<213> ORGANISM: Artificial sequence
<220> FEATURE:
<223> OTHER INFORMATION: primer

<400> SEQUENCE: 25
gcctttatca acaatggaat cccaaccgcc gtcccgtcaa gtc 43

<210> SEQ ID NO 26
<211> LENGTH: 48
<212> TYPE: DNA
<213> ORGANISM: Artificial sequence
<220> FEATURE:
<223> OTHER INFORMATION: primer

<400> SEQUENCE: 26
acaacaaata taaaacaagc ggccgcacta tgaagagatt aggtactc 48

<210> SEQ ID NO 27
<211> LENGTH: 46
<212> TYPE: DNA
<213> ORGANISM: Artificial sequence
<220> FEATURE:
<223> OTHER INFORMATION: primer

<400> SEQUENCE: 27
ggcgaagaat tgttaattaa gagctcggta ccccaagctt gggtta 46

<210> SEQ ID NO 28
<211> LENGTH: 51
<212> TYPE: DNA
<213> ORGANISM: Artificial sequence
<220> FEATURE:
<223> OTHER INFORMATION: primer

<400> SEQUENCE: 28
gttgggattc cattgttgat aaaggcggaa gtaccttcaa agaatggggt c 51

<210> SEQ ID NO 29
<211> LENGTH: 37
<212> TYPE: DNA
<213> ORGANISM: Artificial sequence
<220> FEATURE:
<223> OTHER INFORMATION: primer

<400> SEQUENCE: 29
cttgtgcaat gtagagcgac ctcatgctat acctgag 37

<210> SEQ ID NO 30
<211> LENGTH: 47
<212> TYPE: DNA
<213> ORGANISM: Artificial sequence
<220> FEATURE:
<223> OTHER INFORMATION: primer

<400> SEQUENCE: 30
atgaggtcgc tctacattgc acaagataaa aatatatcat catgaac 47

<210> SEQ ID NO 31
<211> LENGTH: 8721
<212> TYPE: DNA
<213> ORGANISM: Artificial sequence
<220> FEATURE:
<223> OTHER INFORMATION: plasmid pSP-B1

<400> SEQUENCE: 31

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctgg ataaaggcgc gccaaacgac ctaggaattg gagcgacctc   1920
atgctatacc tgagaaagca acctgaccta caggaaagag ttactcaaga ataagaattt   1980
tcgttttaaa acctaagagt cactttaaaa tttgtataca cttatttttt ttataactta   2040
tttaataata aaaatcataa atcataagaa attcgcttat ttagaagtgt caacaacgta   2100
tctaccaacg atttgaccct tttccatctt ttcgtaaatt tctggcaagg tagacaagcc   2160
gacaaccttg attggagact tgaccaaacc tctggcgaag aattgttaat taagagctca   2220
gatcttatcg tcgtcatcct tgtaatccat cgatactagt gcggccgctt gttttatatt   2280
```

```
tgttgtaaaa agtagataat tacttccttg atgatctgta aaaaagagaa aaagaaagca   2340
tctaagaact tgaaaaacta cgaattagaa aagaccaaat atgtatttct tgcattgacc   2400
aatttatgca agtttatata tatgtaaatg taagtttcac gaggttctac taaactaaac   2460
cacccccttg gttagaagaa aagagtgtgt gagaacaggc tgttgttgtc acacgattcg   2520
gacaattctg tttgaaagag agagagtaac agtacgatcg aacgaacttt gctctggaga   2580
tcacagtggg catcatagca tgtggtacta aaccctttcc cgccattcca gaaccttcga   2640
ttgcttgtta caaaacctgt gagccgtcgc taggaccttg ttgtgtgacg aaattggaag   2700
ctgcaatcaa taggaagaca ggaagtcgag cgtgtctggg ttttttcagt tttgttcttt   2760
ttgcaaacaa atcacgagcg acggtaattt ctttctcgat aagaggccac gtgctttatg   2820
agggtaacat caattcaaga aggagggaaa cacttccttt ttctggccct gataatagta   2880
tgagggtgaa gccaaaataa aggattcgcg cccaaatcgg catctttaaa tgcaggtatg   2940
cgatagttcc tcactctttc cttactcacg agtaattctt gcaaatgcct attatgcaga   3000
tgttataata tctgtgcgtc ttgagttgaa gtcaggaatc taaaataaaa attaaggtta   3060
ataaaaagag gaaagaaaaa aaaattaatc gatttacaga aacttgcaca ctaaaaatac   3120
acaactaaaa gcaattacag tatgggaagt catcgacgtt atctctacta tagtatatta   3180
tcatttctat tattatcctg ctcagtggta cttgcaaaac aagataagac cccattcttt   3240
gaaggtactt ccaggccggc cgcacacacc atagcttcaa aatgtttcta ctcctttttt   3300
actcttccag attttctcgg actccgcgca tcgccgtacc acttcaaaac acccaagcac   3360
agcatactaa atttcccctc tttcttcctc tagggtgtcg ttaattaccc gtactaaagg   3420
tttggaaaag aaaaaagaga ccgcctcgtt tctttttctt cgtcgaaaaa ggcaataaaa   3480
atttttatca cgtttctttt tcttgaaaat tttttttttt gatttttttc tctttcgatg   3540
acctcccatt gatatttaag ttaataaacg gtcttcaatt tctcaagttt cagtttcatt   3600
tttcttgttc tattacaact ttttttactt cttgctcatt agaaagaaag catagcaatc   3660
taatctaagt tttaattaca aggatcccgc tcgagatgcg tccattacat ccaattgatt   3720
tcatcttcct atctttagaa aagagacagc aaccaatgca tgtaggcggg ctttttctct   3780
tccaaattcc tgacaatgct ccagacacat tcatccaaga cttggttaat gatatcagaa   3840
tttccaagtc aatacctgtt ccacctttca ataacaaact caacggcttg ttctgggacg   3900
aggatgaaga gttcgatctg gatcatcact ttcgacatat cgcattacca caccctggta   3960
gaatcaggga gttactcatc tacatttccc aagagcattc aacattactt gatagagcca   4020
agccattgtg gacatgcaac ataatcgaag gtatagaagg caatagattt gccatgtact   4080
tcaagataca tcacgctatg gttgatggag tcgctggaat gagactaatc gagaagagcc   4140
tttctcacga tgttacagaa aagtcaattg taccaccttg gtgtgtagaa ggtaaacgag   4200
ctaagcgttt acgtgaacca aaaaccggaa agatcaaaaa gattatgtct ggtatcaaat   4260
ctcaacttca agccacgcct actgtcattc aagagttgtc tcaaacagtg ttcaaagaca   4320
ttggtagaaa cccagatcac gtgtcctcat ttcaagcgcc atgttctatt ctgaaccaaa   4380
gagtatccag tagtagaaga tttgcagcac agtcttttga tcttgatagg ttcagaaaca   4440
ttgcaaagtc tctgaacgtc accataaacg acgtggttct agctgtttgc tctggggcac   4500
tgagagctta tctaatgtca cataacagct tgccatcaaa accattgatt gcgatggttc   4560
ctgcctctat acgtaatgat gattcagatg tcagtaacag aataacaatg atccttgcca   4620
acctagctac tcataaggat gatcctttgc agagattaga aatcattaga agatcagtgc   4680
```

```
aaaactcaaa gcagagattc aaaaggatga ccagtgatca aatcttgaat tactctgcag   4740
tggtatacgg tccagctggt ctgaatatca tatcaggaat gatgccaaaa agacaagcct   4800
ttaacttagt tatctccaat gtacctggtc cacgagaacc tctctactgg aacggagcta   4860
agttggatgc actttaccca gcctctatcg ttttagatgg tcaggctttg aacattacaa   4920
tgactagtta tctagacaag ctagaagttg ggttgattgc gtgtagaaat gccctaccta   4980
gaatgcagaa tttgctgact cacttagaag aggagattca actctttgaa ggcgtcatcg   5040
caaaacaaga ggatatcaaa actgcaaact aacccaagct tggtaccgcg gctagctaag   5100
atccgctcta accgaaaagg aaggagttag acaacctgaa gtctaggtcc ctatttattt   5160
ttttatagtt atgttagtat taagaacgtt atttatattt caaatttttc tttttttttct   5220
gtacagacgc gtgtacgcat gtaacattat actgaaaacc ttgcttgaga aggttttggg   5280
acgctcgaag atcctccgga tcgtttcgcc ggcgtttatc cagctgcatt aatgaatcgg   5340
ccaacgcgcg gggagaggcg gtttgcgtat tgggcgctct tccgcttcct cgctcactga   5400
ctcgctgcgc tcggtcgttc ggctgcggcg agcggtatca gctcactcaa aggcggtaat   5460
acggttatcc acagaatcag gggataacgc aggaaagaac atgtgagcaa aaggccagca   5520
aaaggccagg aaccgtaaaa aggccgcgtt gctggcgttt ttccataggc tccgcccccc   5580
tgacgagcat cacaaaaatc gacgctcaag tcagaggtgg cgaaacccga caggactata   5640
aagataccag gcgtttcccc ctggaagctc cctcgtgcgc tctcctgttc cgaccctgcc   5700
gcttaccgga tacctgtccg cctttctccc ttcgggaagc gtggcgcttt ctcatagctc   5760
acgctgtagg tatctcagtt cggtgtaggt cgttcgctcc aagctgggct gtgtgcacga   5820
accccccgtt cagcccgacc gctgcgcctt atccggtaac tatcgtcttg agtccaaccc   5880
ggtaagacac gacttatcgc cactggcagc agccactggt aacaggatta gcagagcgag   5940
gtatgtaggc ggtgctacag agttcttgaa gtggtggcct aactacggct acactagaag   6000
gacagtattt ggtatctgcg ctctgctgaa gccagttacc ttcggaaaaa gagttggtag   6060
ctcttgatcc ggcaaacaaa ccaccgctgg tagcggtggt ttttttgttt gcaagcagca   6120
gattacgcgc agaaaaaaag gatctcaaga agatcctttg atcttttcta cggggtctga   6180
cgctcagtgg aacgaaaact cacgttaagg gattttggtc atgagattat caaaaaggat   6240
cttcacctag atccttttaa attaaaaatg aagttttaaa tcaatctaaa gtatatatga   6300
gtaaacttgg tctgacagtt accaatgctt aatcagtgag gcacctatct cagcgatctg   6360
tctatttcgt tcatccatag ttgcctgact ccccgtcgtg tagataacta cgatacggga   6420
gggcttacca tctggcccca gtgctgcaat gataccgcga gacccacgct caccggctcc   6480
agatttatca gcaataaacc agccagccgg aagggccgag cgcagaagtg gtcctgcaac   6540
tttatccgcc tccatccagt ctattaattg ttgccgggaa gctagagtaa gtagttcgcc   6600
agttaatagt ttgcgcaacg ttgttgccat tgctacaggc atcgtggtgt cacgctcgtc   6660
gtttggtatg gcttcattca gctccggttc ccaacgatca aggcgagtta catgatcccc   6720
catgttgtgc aaaaaagcgg ttagctcctt cggtcctccg atcgttgtca gaagtaagtt   6780
ggccgcagtg ttatcactca tggttatggc agcactgcat aattctctta ctgtcatgcc   6840
atccgtaaga tgcttttctg tgactggtga gtactcaacc aagtcattct gagaatagtg   6900
tatgcggcga ccgagttgct cttgcccggc gtcaatacgg gataataccg cgccacatag   6960
cagaacttta aaagtgctca tcattggaaa acgttcttcg gggcgaaaac tctcaaggat   7020
```

```
cttaccgctg ttgagatcca gttcgatgta acccactcgt gcacccaact gatcttcagc   7080
atcttttact ttcaccagcg tttctgggtg agcaaaaaca ggaaggcaaa atgccgcaaa   7140
aaagggaata agggcgacac ggaaatgttg aatactcata ctcttccttt ttcaatatta   7200
ttgaagcatt tatcagggtt attgtctcat gagcggatac atatttgaat gtatttagaa   7260
aaataaacaa ataggggttc cgcgcacatt tccccgaaaa gtgccacctg aacgaagcat   7320
ctgtgcttca ttttgtagaa caaaaatgca acgcgagagc gctaattttt caaacaaaga   7380
atctgagctg catttttaca gaacagaaat gcaacgcgaa agcgctattt taccaacgaa   7440
gaatctgtgc ttcatttttg taaaacaaaa atgcaacgcg agagcgctaa tttttcaaac   7500
aaagaatctg agctgcattt ttacagaaca gaaatgcaac gcgagagcgc tattttacca   7560
acaaagaatc tatacttctt ttttgttcta caaaaatgca tcccgagagc gctatttttc   7620
taacaaagca tcttagatta cttttttttct cctttgtgcg ctctataatg cagtctcttg   7680
ataacttttt gcactgtagg tccgttaagg ttagaagaag gctactttgg tgtctatttt   7740
ctcttccata aaaaaagcct gactccactt cccgcgttta ctgattacta gcgaagctgc   7800
gggtgcattt tttcaagata aaggcatccc cgattatatt ctataccgat gtggattgcg   7860
catactttgt gaacagaaag tgatagcgtt gatgattctt cattggtcag aaaattatga   7920
acggtttctt ctattttgtc tctatatact acgtatagga aatgtttaca ttttcgtatt   7980
gttttcgatt cactctatga atagttctta ctacaatttt tttgtctaaa gagtaatact   8040
agagataaac ataaaaaatg tagaggtcga gtttagatgc aagttcaagg agcgaaaggt   8100
ggatgggtag gttatatagg gatatagcac agagatatat agcaaagaga tacttttgag   8160
caatgtttgt ggaagcggta ttcgcaatat tttagtagct cgttacagtc cggtgcgttt   8220
ttggtttttt gaaagtgcgt cttcagagcg cttttggttt tcaaaagcgc tctgaagttc   8280
ctatactttc tagagaatag gaacttcgga ataggaactt caaagcgttt ccgaaaacga   8340
gcgcttccga aaatgcaacg cgagctgcgc acatacagct cactgttcac gtcgcaccta   8400
tatctgcgtg ttgcctgtat atatatatac atgagaagaa cggcatagtg cgtgtttatg   8460
cttaaatgcg tacttatatg cgtctattta tgtaggatga aaggtagtct agtacctcct   8520
gtgatattat cccattccat gcggggtatc gtatgcttcc ttcagcacta ccctttagct   8580
gttctatatg ctgccactcc tcaattggat tagtctcatc cttcaatgct atcatttcct   8640
ttgatattgg atcatactaa gaaaccatta ttatcatgac attaacctat aaaaataggc   8700
gtatcacgag gccctttcgt c                                              8721
```

```
<210> SEQ ID NO 32
<211> LENGTH: 8768
<212> TYPE: DNA
<213> ORGANISM: Artificial sequence
<220> FEATURE:
<223> OTHER INFORMATION: plasmid pSP-B2

<400> SEQUENCE: 32

tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
```

```
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctgg ataaaggcgc gccaaacgac ctaggaattg gagcgacctc   1920
atgctatacc tgagaaagca acctgaccta caggaaagag ttactcaaga ataagaattt   1980
tcgttttaaa acctaagagt cactttaaaa tttgtataca cttatttttt ttataactta   2040
tttaataata aaaatcataa atcataagaa attcgcttat ttagaagtgt caacaacgta   2100
tctaccaacg atttgaccct tttccatctt ttcgtaaatt tctggcaagg tagacaagcc   2160
gacaaccttg attggagact tgaccaaacc tctggcgaag aattgttaat taagagctca   2220
gatcttatcg tcgtcatcct tgtaatccat cgatactagt gcggccgctt gttttatatt   2280
tgttgtaaaa agtagataat tacttccttg atgatctgta aaaaagagaa aaagaaagca   2340
tctaagaact tgaaaaacta cgaattagaa aagaccaaat atgtatttct tgcattgacc   2400
aatttatgca agtttatata tatgtaaatg taagtttcac gaggttctac taaactaaac   2460
cacccccttg gttagaagaa aagagtgtgt gagaacaggc tgttgttgtc acacgattcg   2520
gacaattctg tttgaaagag agagagtaac agtacgatcg aacgaacttt gctctggaga   2580
tcacagtggg catcatagca tgtggtacta aaccctttcc cgccattcca gaaccttcga   2640
ttgcttgtta caaaacctgt gagccgtcgc taggaccttg ttgtgtgacg aaattggaag   2700
```

```
ctgcaatcaa taggaagaca ggaagtcgag cgtgtctggg ttttttcagt tttgttcttt   2760

ttgcaaacaa atcacgagcg acggtaattt ctttctcgat aagaggccac gtgctttatg   2820

agggtaacat caattcaaga aggagggaaa cacttccttt ttctggccct gataatagta   2880

tgagggtgaa gccaaaataa aggattcgcg cccaaatcgg catctttaaa tgcaggtatg   2940

cgatagttcc tcactctttc cttactcacg agtaattctt gcaaatgcct attatgcaga   3000

tgttataata tctgtgcgtc ttgagttgaa gtcaggaatc taaaataaaa attaaggtta   3060

ataaaaagag gaaagaaaaa aaaattaatc gatttacaga aacttgcaca ctaaaaatac   3120

acaactaaaa gcaattacag tatgggaagt catcgacgtt atctctacta tagtatatta   3180

tcatttctat tattatcctg ctcagtggta cttgcaaaac aagataagac cccattcttt   3240

gaaggtactt ccaggccggc cgcacacacc atagcttcaa aatgtttcta ctcctttttt   3300

actcttccag attttctcgg actccgcgca tcgccgtacc acttcaaaac acccaagcac   3360

agcatactaa atttcccctc tttcttcctc tagggtgtcg ttaattaccc gtactaaagg   3420

tttggaaaag aaaaaagaga ccgcctcgtt tctttttctt cgtcgaaaaa ggcaataaaa   3480

atttttatca cgtttctttt tcttgaaaat tttttttttt gatttttttc tctttcgatg   3540

acctcccatt gatatttaag ttaataaacg gtcttcaatt tctcaagttt cagtttcatt   3600

tttcttgttc tattacaact ttttttactt cttgctcatt agaaagaaag catagcaatc   3660

taatctaagt tttaattaca aggatcccgc tcgagatgaa gagattaggt actctagacg   3720

ctagttggct tgcagtcgaa tccgaagata cgccaatgca cgtgggcact ctccaaatct   3780

tctcattacc agaaggtgct ccagagacat ttctacgtga tatggttaca aggatgaaag   3840

aggcaggaga tgttgcccca ccatggggtt acaagctcgc atggtccggt ttccttggca   3900

gggttattgc tcctgcctgg aaggtagaca aagatatcga tttggattat catgtccgac   3960

atagtgcatt gccaagacca ggtggtgaaa gagagctagg gatacttgtt tctagattac   4020

actccaaccc tttagatttc tctagaccac tatgggaatg ccatgtcatt gaaggtcttg   4080

aaaacaacag atttgcactg tatactaaga tgcatcactc tatgattgat gggatatctg   4140

gagtaagatt gatgcaaaga gtattgacca ctgacccaga gagatgtaac atgcctcctc   4200

catggacagt tagacctcac cagagaagag gagctaaaac agataaagag gcttctgtgc   4260

ctgctgcggt ttctcaagca atggacgcct tgaagctcca agcggatatg gcccctagac   4320

tatggcaagc tggcaatcgt ctagtacatt ctgtcagaca ccctgaggat ggcttaacag   4380

ctccattcac cggtccagtg tctgtcctta accatagagt tacagcgcag agaagattcg   4440

ctactcaaca ctaccaacta gatagattga aaaacttagc gcatgccagt ggtggttcac   4500

tgaatgatat agtgctttac ttatgtggta ctgccttgag aaggtttttg gctgagcaga   4560

ataacttgcc tgacacacct ttaacggcag gaattccagt gaatatcaga ccagctgatg   4620

acgaaggcac cggaacacaa atctcattca tgattgctag tttggctact gacgaagctg   4680

atcctctcaa tagattacaa cagatcaaaa cctcaacacg aagggcgaag gagcatctcc   4740

aaaagttgcc taagtcagca ctaacacaat acacaatgct gctgatgtca ccttacatct   4800

tacaattgat gagcggattg ggaggtagaa tgaggccagt tttcaatgtt actataagca   4860

atgtccctgg gcctgagggg acattgtatt acgaaggagc tagattggaa gccatgtacc   4920

cagtttccct tatcgcccac ggtggtgcct tgaacatcac atgcctgtct tacgctggct   4980

cccttaactt tgggtttacc ggttgtcgtg atactttacc atcaatgcaa aagttagcag   5040

tctatactgg tgaagcattg gatgaactcg aatctctaat tctgccacca aagaagcgtg   5100
```

```
cccgtactag aaagtaaccc aagcttgggg taccgcggct agctaagatc cgctctaacc   5160
gaaaaggaag gagttagaca acctgaagtc taggtcccta tttatttttt tatagttatg   5220
ttagtattaa gaacgttatt tatatttcaa atttttcttt tttttctgta cagacgcgtg   5280
tacgcatgta acattatact gaaaaccttg cttgagaagg ttttgggacg ctcgaagatc   5340
ctccggatcg tttcgccggc gtttatccag ctgcattaat gaatcggcca acgcgcgggg   5400
agaggcggtt tgcgtattgg gcgctcttcc gcttcctcgc tcactgactc gctgcgctcg   5460
gtcgttcggc tgcggcgagc ggtatcagct cactcaaagg cggtaatacg gttatccaca   5520
gaatcagggg ataacgcagg aaagaacatg tgagcaaaag gccagcaaaa ggccaggaac   5580
cgtaaaaagg ccgcgttgct ggcgtttttc cataggctcc gcccccctga cgagcatcac   5640
aaaaatcgac gctcaagtca gaggtggcga aacccgacag gactataaag ataccaggcg   5700
tttccccctg gaagctccct cgtgcgctct cctgttccga ccctgccgct taccggatac   5760
ctgtccgcct ttctcccttc gggaagcgtg gcgctttctc atagctcacg ctgtaggtat   5820
ctcagttcgg tgtaggtcgt tcgctccaag ctgggctgtg tgcacgaacc ccccgttcag   5880
cccgaccgct gcgccttatc cggtaactat cgtcttgagt ccaacccggt aagacacgac   5940
ttatcgccac tggcagcagc cactggtaac aggattagca gagcgaggta tgtaggcggt   6000
gctacagagt tcttgaagtg gtggcctaac tacggctaca ctagaaggac agtatttggt   6060
atctgcgctc tgctgaagcc agttaccttc ggaaaaagag ttggtagctc ttgatccggc   6120
aaacaaacca ccgctggtag cggtggtttt tttgtttgca agcagcagat tacgcgcaga   6180
aaaaaaggat ctcaagaaga tcctttgatc ttttctacgg ggtctgacgc tcagtggaac   6240
gaaaactcac gttaagggat tttggtcatg agattatcaa aaaggatctt cacctagatc   6300
cttttaaatt aaaaatgaag ttttaaatca atctaaagta tatatgagta aacttggtct   6360
gacagttacc aatgcttaat cagtgaggca cctatctcag cgatctgtct atttcgttca   6420
tccatagttg cctgactccc cgtcgtgtag ataactacga tacgggaggg cttaccatct   6480
ggccccagtg ctgcaatgat accgcgagac ccacgctcac cggctccaga tttatcagca   6540
ataaaccagc cagccggaag ggccgagcgc agaagtggtc ctgcaacttt atccgcctcc   6600
atccagtcta ttaattgttg ccgggaagct agagtaagta gttcgccagt taatagtttg   6660
cgcaacgttg ttgccattgc tacaggcatc gtggtgtcac gctcgtcgtt tggtatggct   6720
tcattcagct ccggttccca acgatcaagg cgagttacat gatcccccat gttgtgcaaa   6780
aaagcggtta gctccttcgg tcctccgatc gttgtcagaa gtaagttggc cgcagtgtta   6840
tcactcatgg ttatggcagc actgcataat tctcttactg tcatgccatc cgtaagatgc   6900
ttttctgtga ctggtgagta ctcaaccaag tcattctgag aatagtgtat gcggcgaccg   6960
agttgctctt gcccggcgtc aatacgggat aataccgcgc cacatagcag aactttaaaa   7020
gtgctcatca ttggaaaacg ttcttcgggg cgaaaactct caaggatctt accgctgttg   7080
agatccagtt cgatgtaacc cactcgtgca cccaactgat cttcagcatc ttttactttc   7140
accagcgttt ctgggtgagc aaaaacagga aggcaaaatg ccgcaaaaaa gggaataagg   7200
gcgacacgga aatgttgaat actcatactc ttcctttttc aatattattg aagcatttat   7260
cagggttatt gtctcatgag cggatacata tttgaatgta tttagaaaaa taaacaaata   7320
ggggttccgc gcacatttcc ccgaaaagtg ccacctgaac gaagcatctg tgcttcattt   7380
tgtagaacaa aaatgcaacg cgagagcgct aatttttcaa acaaagaatc tgagctgcat   7440
```

```
ttttacagaa cagaaatgca acgcgaaagc gctattttac caacgaagaa tctgtgcttc   7500
atttttgtaa aacaaaaatg caacgcgaga gcgctaattt ttcaaacaaa gaatctgagc   7560
tgcattttta cagaacagaa atgcaacgcg agagcgctat tttaccaaca aagaatctat   7620
acttcttttt tgttctacaa aaatgcatcc cgagagcgct atttttctaa caaagcatct   7680
tagattactt tttttctcct ttgtgcgctc tataatgcag tctcttgata actttttgca   7740
ctgtaggtcc gttaaggtta gaagaaggct actttggtgt ctattttctc ttccataaaa   7800
aaagcctgac tccacttccc gcgtttactg attactagcg aagctgcggg tgcatttttt   7860
caagataaag gcatccccga ttatattcta taccgatgtg gattgcgcat actttgtgaa   7920
cagaaagtga tagcgttgat gattcttcat tggtcagaaa attatgaacg gtttcttcta   7980
ttttgtctct atatactacg tataggaaat gtttacattt tcgtattgtt ttcgattcac   8040
tctatgaata gttcttacta caattttttt gtctaaagag taatactaga gataaacata   8100
aaaaatgtag aggtcgagtt tagatgcaag ttcaaggagc gaaaggtgga tgggtaggtt   8160
atatagggat atagcacaga gatatatagc aaagagatac ttttgagcaa tgtttgtgga   8220
agcggtattc gcaatatttt agtagctcgt tacagtccgg tgcgtttttg gttttttgaa   8280
agtgcgtctt cagagcgctt ttggttttca aaagcgctct gaagttccta tactttctag   8340
agaataggaa cttcggaata ggaacttcaa agcgtttccg aaaacgagcg cttccgaaaa   8400
tgcaacgcga gctgcgcaca tacagctcac tgttcacgtc gcacctatat ctgcgtgttg   8460
cctgtatata tatatacatg agaagaacgg catagtgcgt gtttatgctt aaatgcgtac   8520
ttatatgcgt ctatttatgt aggatgaaag gtagtctagt acctcctgtg atattatccc   8580
attccatgcg gggtatcgta tgcttccttc agcactaccc tttagctgtt ctatatgctg   8640
ccactcctca attggattag tctcatcctt caatgctatc atttcctttg atattggatc   8700
atactaagaa accattatta tcatgacatt aacctataaa aataggcgta tcacgaggcc   8760
ctttcgtc                                                            8768
```

<210> SEQ ID NO 33
<211> LENGTH: 8766
<212> TYPE: DNA
<213> ORGANISM: Artificial sequence
<220> FEATURE:
<223> OTHER INFORMATION: plasmid pSP-B3

<400> SEQUENCE: 33

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
```

```
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctgg ataaaggcgc gccaaacgac ctaggaattg gagcgacctc   1920
atgctatacc tgagaaagca acctgaccta caggaaagag ttactcaaga ataagaattt   1980
tcgttttaaa acctaagagt cactttaaaa tttgtataca cttatttttt ttataactta   2040
tttaataata aaaatcataa atcataagaa attcgcttat ttagaagtgt caacaacgta   2100
tctaccaacg atttgaccct tttccatctt ttcgtaaatt tctggcaagg tagacaagcc   2160
gacaaccttg attggagact tgaccaaacc tctggcgaag aattgttaat taagagctca   2220
gatcttatcg tcgtcatcct tgtaatccat cgatactagt gcggccgctt gttttatatt   2280
tgttgtaaaa agtagataat tacttccttg atgatctgta aaaaagagaa aaagaaagca   2340
tctaagaact tgaaaaacta cgaattagaa aagaccaaat atgtatttct tgcattgacc   2400
aatttatgca agtttatata tatgtaaatg taagtttcac gaggttctac taaactaaac   2460
cacccccttg gttagaagaa aagagtgtgt gagaacaggc tgttgttgtc acacgattcg   2520
gacaattctg tttgaaagag agagagtaac agtacgatcg aacgaacttt gctctggaga   2580
tcacagtggg catcatagca tgtggtacta aaccctttcc cgccattcca gaaccttcga   2640
ttgcttgtta caaaacctgt gagccgtcgc taggaccttg ttgtgtgacg aaattggaag   2700
ctgcaatcaa taggaagaca ggaagtcgag cgtgtctggg ttttttcagt tttgttcttt   2760
ttgcaaacaa atcacgagcg acggtaattt ctttctcgat aagaggccac gtgctttatg   2820
agggtaacat caattcaaga aggagggaaa cacttccttt ttctggccct gataatagta   2880
tgagggtgaa gccaaaataa aggattcgcg cccaaatcgg catctttaaa tgcaggtatg   2940
cgatagttcc tcactctttc cttactcacg agtaattctt gcaaatgcct attatgcaga   3000
tgttataata tctgtgcgtc ttgagttgaa gtcaggaatc taaaataaaa attaaggtta   3060
```

```
ataaaaagag gaaagaaaaa aaaattaatc gatttacaga aacttgcaca ctaaaaatac   3120

acaactaaaa gcaattacag tatgggaagt catcgacgtt atctctacta tagtatatta   3180

tcatttctat tattatcctg ctcagtggta cttgcaaaac aagataagac cccattcttt   3240

gaaggtactt ccaggccggc cgcacacacc atagcttcaa aatgtttcta ctcctttttt   3300

actcttccag attttctcgg actccgcgca tcgccgtacc acttcaaaac acccaagcac   3360

agcatactaa atttcccctc tttcttcctc tagggtgtcg ttaattaccc gtactaaagg   3420

tttggaaaag aaaaaagaga ccgcctcgtt tctttttctt cgtcgaaaaa ggcaataaaa   3480

atttttatca cgtttctttt tcttgaaaat tttttttttt gatttttttc tctttcgatg   3540

acctcccatt gatatttaag ttaataaacg gtcttcaatt tctcaagttt cagtttcatt   3600

tttcttgttc tattacaact ttttttactt cttgctcatt agaaagaaag catagcaatc   3660

taatctaagt tttaattaca aggatcccgc tcgagttgac cgacgtgatt accacaaacc   3720

aaagatacat gactcagacc gatttcatgt cttggagaat ggaggaagat ccaatactga   3780

gaagcacgat cgttgcagtg gccctgttgg acagaaggcc tgatcaaagt agatttgttg   3840

atatgatgag aagagctgtc gatctagttc cattgtttcg tagaaccgcc attgaagatc   3900

cactcggctt ggctcctcca agatgggccg atgatagaga ttttgaccta tcatggcatc   3960

taagacgata tactttagcg gaacctagga cttgggacgg cgtcctagat ttcgcacgta   4020

ctgcagagat gacagctttt gataaacgta gacctttgtg ggagttcaca atcttagatg   4080

gtcttaatga tggtagatca gcgttggtta tgaaggttca ccattcactc acggatggtg   4140

tctctggtat gcaaattgcc agagaaatcg tggactttac tagagaaggt acgccacgac   4200

caggacgtac agatagagct acagctgttc ctcatggagg ctcttctaga cctccttcta   4260

gacttagttg gtatagagat acagctgcag acgtaacaca ccgagctgcg aacatcttgg   4320

gtagaaattc tgttaggcta gttagagcgc cacgtgctac atggagagaa gccactgcgt   4380

tagctggttc cactttaaga ttaaccagac cagttgtttc cacattgtca ccagtgatga   4440

ctaagagatc aacaagacga cattgtgctg tcatcgacgt ccctgtagaa gctctcgcac   4500

aggctgcagc agccgcagct gggtctatca atgacgcttt ccttgctgca gtcctgttgg   4560

gtatggcaaa gtaccataga cttcatggtg ccgaaatcag agaattacgt atgactttac   4620

caatatcttt aaggacagaa acagatccat taggtgggaa tagaatttcc ctagccagat   4680

tcgctttgcc tactgatatt gatgatccag ctgagttgat gaggagggta cacgctactg   4740

tagatgcatg gagaagagaa ccagcaatac cattttcccc tatgattgct ggtgccgtaa   4800

acttacttcc tgcctcaact ttagggaaca tgttgaaaca cgttgacttt gtagcatcta   4860

acgtcgctgg ctcaccagtt cctctattca tagccggatc agagatccta cattactacg   4920

cgttctcacc aactcttgga tctgcattca atgttacgct gatgagttac accactcaat   4980

gctgtgtcgg gataaacgct gatacagacg ctgtacctga tcttgccaca ctgaccgaaa   5040

gtttggcaga tggattcaga gccgttttgg gcttatgtgc taagactaca gacacaagag   5100

tggtggtggc tagctaaccc aagcttggta ccgcggctag ctaagatccg ctctaaccga   5160

aaaggaagga gttagacaac ctgaagtcta ggtccctatt tattttttta tagttatgtt   5220

agtattaaga acgttattta tatttcaaat ttttcttttt tttctgtaca gacgcgtgta   5280

cgcatgtaac attatactga aaaccttgct tgagaaggtt ttgggacgct cgaagatcct   5340

ccggatcgtt tcgccggcgt ttatccagct gcattaatga atcggccaac gcgcggggag   5400

aggcggtttg cgtattgggc gctcttccgc ttcctcgctc actgactcgc tgcgctcggt   5460
```

```
cgttcggctg cggcgagcgg tatcagctca ctcaaaggcg gtaatacggt tatccacaga   5520
atcaggggat aacgcaggaa agaacatgtg agcaaaaggc cagcaaaagg ccaggaaccg   5580
taaaaaggcc gcgttgctgg cgtttttcca taggctccgc ccccctgacg agcatcacaa   5640
aaatcgacgc tcaagtcaga ggtggcgaaa cccgacagga ctataaagat accaggcgtt   5700
tccccctgga agctccctcg tgcgctctcc tgttccgacc ctgccgctta ccggatacct   5760
gtccgccttt ctcccttcgg gaagcgtggc gctttctcat agctcacgct gtaggtatct   5820
cagttcggtg taggtcgttc gctccaagct gggctgtgtg cacgaacccc ccgttcagcc   5880
cgaccgctgc gccttatccg gtaactatcg tcttgagtcc aacccggtaa gacacgactt   5940
atcgccactg gcagcagcca ctggtaacag gattagcaga gcgaggtatg taggcggtgc   6000
tacagagttc ttgaagtggt ggcctaacta cggctacact agaaggacag tatttggtat   6060
ctgcgctctg ctgaagccag ttaccttcgg aaaaagagtt ggtagctctt gatccggcaa   6120
acaaaccacc gctggtagcg gtggtttttt tgtttgcaag cagcagatta cgcgcagaaa   6180
aaaaggatct caagaagatc ctttgatctt ttctacgggg tctgacgctc agtggaacga   6240
aaactcacgt taagggattt tggtcatgag attatcaaaa aggatcttca cctagatcct   6300
tttaaattaa aaatgaagtt ttaaatcaat ctaaagtata tatgagtaaa cttggtctga   6360
cagttaccaa tgcttaatca gtgaggcacc tatctcagcg atctgtctat ttcgttcatc   6420
catagttgcc tgactccccg tcgtgtagat aactacgata cgggagggct taccatctgg   6480
ccccagtgct gcaatgatac cgcgagaccc acgctcaccg gctccagatt tatcagcaat   6540
aaaccagcca gccggaaggg ccgagcgcag aagtggtcct gcaactttat ccgcctccat   6600
ccagtctatt aattgttgcc gggaagctag agtaagtagt tcgccagtta atagtttgcg   6660
caacgttgtt gccattgcta caggcatcgt ggtgtcacgc tcgtcgtttg gtatggcttc   6720
attcagctcc ggttcccaac gatcaaggcg agttacatga tcccccatgt tgtgcaaaaa   6780
agcggttagc tccttcggtc ctccgatcgt tgtcagaagt aagttggccg cagtgttatc   6840
actcatggtt atggcagcac tgcataattc tcttactgtc atgccatccg taagatgctt   6900
ttctgtgact ggtgagtact caaccaagtc attctgagaa tagtgtatgc ggcgaccgag   6960
ttgctcttgc ccggcgtcaa tacgggataa taccgcgcca catagcagaa ctttaaaagt   7020
gctcatcatt ggaaaacgtt cttcggggcg aaaactctca aggatcttac cgctgttgag   7080
atccagttcg atgtaaccca ctcgtgcacc caactgatct tcagcatctt ttactttcac   7140
cagcgtttct gggtgagcaa aaacaggaag gcaaaatgcc gcaaaaaagg gaataagggc   7200
gacacggaaa tgttgaatac tcatactctt cctttttcaa tattattgaa gcatttatca   7260
gggttattgt ctcatgagcg gatacatatt tgaatgtatt tagaaaaata aacaaatagg   7320
ggttccgcgc acatttcccc gaaaagtgcc acctgaacga agcatctgtg cttcattttg   7380
tagaacaaaa atgcaacgcg agagcgctaa tttttcaaac aaagaatctg agctgcattt   7440
ttacagaaca gaaatgcaac gcgaaagcgc tattttacca acgaagaatc tgtgcttcat   7500
ttttgtaaaa caaaaatgca acgcgagagc gctaattttt caaacaaaga atctgagctg   7560
catttttaca gaacagaaat gcaacgcgag agcgctattt taccaacaaa gaatctatac   7620
ttcttttttg ttctacaaaa atgcatcccg agagcgctat ttttctaaca aagcatctta   7680
gattactttt tttctccttt gtgcgctcta taatgcagtc tcttgataac tttttgcact   7740
gtaggtccgt taaggttaga agaaggctac tttggtgtct attttctctt ccataaaaaa   7800
```

```
agcctgactc cacttcccgc gtttactgat tactagcgaa gctgcgggtg catttttca   7860
agataaaggc atccccgatt atattctata ccgatgtgga ttgcgcatac tttgtgaaca   7920
gaaagtgata gcgttgatga ttcttcattg gtcagaaaat tatgaacggt ttcttctatt   7980
ttgtctctat atactacgta taggaaatgt ttacattttc gtattgtttt cgattcactc   8040
tatgaatagt tcttactaca attttttgt ctaaagagta atactagaga taaacataaa   8100
aaatgtagag gtcgagttta gatgcaagtt caaggagcga aaggtggatg ggtaggttat   8160
atagggatat agcacagaga tatatagcaa agagatactt ttgagcaatg tttgtggaag   8220
cggtattcgc aatattttag tagctcgtta cagtccggtg cgtttttggt tttttgaaag   8280
tgcgtcttca gagcgctttt ggttttcaaa agcgctctga agttcctata ctttctagag   8340
aataggaact tcggaatagg aacttcaaag cgtttccgaa aacgagcgct tccgaaaatg   8400
caacgcgagc tgcgcacata cagctcactg ttcacgtcgc acctatatct gcgtgttgcc   8460
tgtatatata tatacatgag aagaacggca tagtgcgtgt ttatgcttaa atgcgtactt   8520
atatgcgtct atttatgtag gatgaaaggt agtctagtac ctcctgtgat attatcccat   8580
tccatgcggg gtatcgtatg cttccttcag cactaccctt tagctgttct atatgctgcc   8640
actcctcaat tggattagtc tcatccttca atgctatcat ttcctttgat attggatcat   8700
actaagaaac cattattatc atgacattaa cctataaaaa taggcgtatc acgaggccct   8760
ttcgtc                                                              8766
```

<210> SEQ ID NO 34
<211> LENGTH: 8346
<212> TYPE: DNA
<213> ORGANISM: Artificial sequence
<220> FEATURE:
<223> OTHER INFORMATION: plasmid pSP-B4

<400> SEQUENCE: 34

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat cattttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
```

```
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctgg ataaaggcgc gccaaacgac ctaggaattg gagcgacctc   1920
atgctatacc tgagaaagca acctgaccta caggaaagag ttactcaaga ataagaattt   1980
tcgttttaaa acctaagagt cactttaaaa tttgtataca cttatttttt ttataactta   2040
tttaataata aaaatcataa atcataagaa attcgcttat ttagaagtgt caacaacgta   2100
tctaccaacg atttgaccct tttccatctt ttcgtaaatt tctggcaagg tagacaagcc   2160
gacaaccttg attggagact tgaccaaacc tctggcgaag aattgttaat taagagctca   2220
gatcttatcg tcgtcatcct tgtaatccat cgatactagt gcggccgctt gttttatatt   2280
tgttgtaaaa agtagataat tacttccttg atgatctgta aaaaagagaa aaagaaagca   2340
tctaagaact tgaaaaacta cgaattagaa aagaccaaat atgtatttct tgcattgacc   2400
aatttatgca agtttatata tatgtaaatg taagtttcac gaggttctac taaactaaac   2460
cacccccttg gttagaagaa aagagtgtgt gagaacaggc tgttgttgtc acacgattcg   2520
gacaattctg tttgaaagag agagagtaac agtacgatcg aacgaacttt gctctggaga   2580
tcacagtggg catcatagca tgtggtacta aacccttttcc cgccattcca gaaccttcga   2640
ttgcttgtta caaaacctgt gagccgtcgc taggaccttg ttgtgtgacg aaattggaag   2700
ctgcaatcaa taggaagaca ggaagtcgag cgtgtctggg ttttttcagt tttgttcttt   2760
ttgcaaacaa atcacgagcg acggtaattt ctttctcgat aagaggccac gtgctttatg   2820
agggtaacat caattcaaga aggagggaaa cacttccttt ttctggccct gataatagta   2880
tgagggtgaa gccaaaataa aggattcgcg cccaaatcgg catctttaaa tgcaggtatg   2940
cgatagttcc tcactctttc cttactcacg agtaattctt gcaaatgcct attatgcaga   3000
tgttataata tctgtgcgtc ttgagttgaa gtcaggaatc taaaataaaa attaaggtta   3060
ataaaaagag gaaagaaaaa aaaattaatc gatttacaga aacttgcaca ctaaaaatac   3120
acaactaaaa gcaattacag tatgggaagt catcgacgtt atctctacta tagtatatta   3180
tcatttctat tattatcctg ctcagtggta cttgcaaaac aagataagac cccattcttt   3240
gaaggtactt ccaggccggc cgcacacacc atagcttcaa aatgtttcta ctcctttttt   3300
actcttccag attttctcgg actccgcgca tcgccgtacc acttcaaaac acccaagcac   3360
agcatactaa atttcccctc tttcttcctc tagggtgtcg ttaattaccc gtactaaagg   3420
```

```
tttggaaaag aaaaaagaga ccgcctcgtt tctttttctt cgtcgaaaaa ggcaataaaa   3480
atttttatca cgtttctttt tcttgaaaat ttttttttt gattttttc tctttcgatg   3540
acctcccatt gatatttaag ttaataaacg gtcttcaatt tctcaagttt cagtttcatt   3600
tttcttgttc tattacaact ttttttactt cttgctcatt agaaagaaag catagcaatc   3660
taatctaagt tttaattaca aggatcccgc tcgagatgtt ctggccaacc aaaaaggatt   3720
tgaaaactgc aatggaagta tttgctctct tccaatgggc cctttccgct ttggtaattg   3780
tcactactgt gatcatagtc aatttgtatc ttgttgtgtt tacatcatat tggccagtga   3840
cggtcttaat gttgacatgg ttagcattcg attggaaaac accagaaaga ggtggcagga   3900
gattcacatg tgtccgtaag tggagattgt ggaagcacta ctctgattac ttccctttga   3960
aaatggttaa gactaaggac atatcaccag atagaaacta catcttagta tgtcatccac   4020
atggtcttat ggcacattca tgtttcggac atttcgccac agatacaact ggattcagta   4080
agacttttcc tggtatcact ccttacatgc taacattagg cgcctttttc tgggttccat   4140
tccttagaga ctatgttatg tccactggct catgctctgt gtccagaagc tcaatggact   4200
tcctcctaac acaaaaagga actggaaaca tgttggttgt agttgtaggt ggtttagctg   4260
agtgtcgtta ctctacgcca ggctctacaa ccctgttttt gaaaaagaga cagggtttcg   4320
tgagaactgc gttgaagcat ggtgtttctc tgatcccagc ttacgctttc ggggaaactg   4380
atctctacga tcaacacata ttcacaccag gtggttttgt caatagattt cagaaatggt   4440
ttcaaaagat ggtacacatc tacccatgcg ctttctatgg cagagggctc accaaaaact   4500
catgggggct actaccttat tcacagcctg ttaccacagt ggttggagaa cctttacctc   4560
tgccaaagat tgaaaaccct tccgaagaga ttgttgcgaa gtaccataca ctgtacatcg   4620
atgcacttag gaagctattc gaccaacaca aaactaagtt tggtattagt gaaacccaag   4680
agttggtcat tgtttaaccc aagcttggta ccgcggctag ctaagatccg ctctaaccga   4740
aaaggaagga gttagacaac ctgaagtcta ggtccctatt tattttttta tagttatgtt   4800
agtattaaga acgttattta tatttcaaat ttttcttttt tttctgtaca gacgcgtgta   4860
cgcatgtaac attatactga aaaccttgct tgagaaggtt ttgggacgct cgaagatcct   4920
ccggatcgtt tcgccggcgt ttatccagct gcattaatga atcggccaac gcgcggggag   4980
aggcggtttg cgtattgggc gctcttccgc ttcctcgctc actgactcgc tgcgctcggt   5040
cgttcggctg cggcgagcgg tatcagctca ctcaaaggcg gtaatacggt tatccacaga   5100
atcaggggat aacgcaggaa agaacatgtg agcaaaaggc cagcaaaagg ccaggaaccg   5160
taaaaaggcc gcgttgctgg cgtttttcca taggctccgc ccccctgacg agcatcacaa   5220
aaatcgacgc tcaagtcaga ggtggcgaaa cccgacagga ctataaagat accaggcgtt   5280
tccccctgga agctccctcg tgcgctctcc tgttccgacc ctgccgctta ccggatacct   5340
gtccgccttt ctcccttcgg gaagcgtggc gctttctcat agctcacgct gtaggtatct   5400
cagttcggtg taggtcgttc gctccaagct gggctgtgtg cacgaacccc ccgttcagcc   5460
cgaccgctgc gccttatccg gtaactatcg tcttgagtcc aacccggtaa gacacgactt   5520
atcgccactg gcagcagcca ctggtaacag gattagcaga gcgaggtatg taggcggtgc   5580
tacagagttc ttgaagtggt ggcctaacta cggctacact agaaggacag tatttggtat   5640
ctgcgctctg ctgaagccag ttaccttcgg aaaaagagtt ggtagctctt gatccggcaa   5700
acaaaccacc gctggtagcg gtggtttttt tgtttgcaag cagcagatta cgcgcagaaa   5760
aaaaggatct caagaagatc ctttgatctt ttctacgggg tctgacgctc agtggaacga   5820
```

```
aaactcacgt taagggattt tggtcatgag attatcaaaa aggatcttca cctagatcct   5880
tttaaattaa aaatgaagtt ttaaatcaat ctaaagtata tatgagtaaa cttggtctga   5940
cagttaccaa tgcttaatca gtgaggcacc tatctcagcg atctgtctat ttcgttcatc   6000
catagttgcc tgactccccg tcgtgtagat aactacgata cgggagggct taccatctgg   6060
ccccagtgct gcaatgatac cgcgagaccc acgctcaccg gctccagatt tatcagcaat   6120
aaaccagcca gccggaaggg ccgagcgcag aagtggtcct gcaactttat ccgcctccat   6180
ccagtctatt aattgttgcc gggaagctag agtaagtagt tcgccagtta atagtttgcg   6240
caacgttgtt gccattgcta caggcatcgt ggtgtcacgc tcgtcgtttg gtatggcttc   6300
attcagctcc ggttcccaac gatcaaggcg agttacatga tcccccatgt tgtgcaaaaa   6360
agcggttagc tccttcggtc ctccgatcgt tgtcagaagt aagttggccg cagtgttatc   6420
actcatggtt atggcagcac tgcataattc tcttactgtc atgccatccg taagatgctt   6480
ttctgtgact ggtgagtact caaccaagtc attctgagaa tagtgtatgc ggcgaccgag   6540
ttgctcttgc ccggcgtcaa tacgggataa taccgcgcca catagcagaa ctttaaaagt   6600
gctcatcatt ggaaaacgtt cttcggggcg aaaactctca aggatcttac cgctgttgag   6660
atccagttcg atgtaaccca ctcgtgcacc caactgatct tcagcatctt ttactttcac   6720
cagcgtttct gggtgagcaa aaacaggaag gcaaaatgcc gcaaaaaagg gaataagggc   6780
gacacggaaa tgttgaatac tcatactctt cctttttcaa tattattgaa gcatttatca   6840
gggttattgt ctcatgagcg gatacatatt tgaatgtatt tagaaaaata aacaaatagg   6900
ggttccgcgc acatttcccc gaaaagtgcc acctgaacga agcatctgtg cttcattttg   6960
tagaacaaaa atgcaacgcg agagcgctaa tttttcaaac aaagaatctg agctgcattt   7020
ttacagaaca gaaatgcaac gcgaaagcgc tattttacca acgaagaatc tgtgcttcat   7080
ttttgtaaaa caaaaatgca acgcgagagc gctaattttt caaacaaaga atctgagctg   7140
catttttaca gaacagaaat gcaacgcgag agcgctattt taccaacaaa gaatctatac   7200
ttcttttttg ttctacaaaa atgcatcccg agagcgctat ttttctaaca aagcatctta   7260
gattactttt tttctccttt gtgcgctcta taatgcagtc tcttgataac tttttgcact   7320
gtaggtccgt taaggttaga agaaggctac tttggtgtct attttctctt ccataaaaaa   7380
agcctgactc cacttcccgc gtttactgat tactagcgaa gctgcgggtg cattttttca   7440
agataaaggc atccccgatt atattctata ccgatgtgga ttgcgcatac tttgtgaaca   7500
gaaagtgata gcgttgatga ttcttcattg gtcagaaaat tatgaacggt ttcttctatt   7560
ttgtctctat atactacgta taggaaatgt ttacattttc gtattgtttt cgattcactc   7620
tatgaatagt tcttactaca atttttttgt ctaaagagta atactagaga taaacataaa   7680
aaatgtagag gtcgagttta gatgcaagtt caaggagcga aaggtggatg ggtaggttat   7740
atagggatat agcacagaga tatatagcaa agagatactt ttgagcaatg tttgtggaag   7800
cggtattcgc aatattttag tagctcgtta cagtccggtg cgtttttggt tttttgaaag   7860
tgcgtcttca gagcgctttt ggttttcaaa agcgctctga agttcctata ctttctagag   7920
aataggaact tcggaatagg aacttcaaag cgtttccgaa aacgagcgct tccgaaaatg   7980
caacgcgagc tgcgcacata cagctcactg ttcacgtcgc acctatatct gcgtgttgcc   8040
tgtatatata tatacatgag aagaacggca tagtgcgtgt ttatgcttaa atgcgtactt   8100
atatgcgtct atttatgtag gatgaaaggt agtctagtac ctcctgtgat attatcccat   8160
```

```
tccatgcggg gtatcgtatg cttccttcag cactaccctt tagctgttct atatgctgcc   8220

actcctcaat tggattagtc tcatccttca atgctatcat ttcctttgat attggatcat   8280

actaagaaac cattattatc atgacattaa cctataaaaa taggcgtatc acgaggccct   8340

ttcgtc                                                              8346
```

<210> SEQ ID NO 35
<211> LENGTH: 8772
<212> TYPE: DNA
<213> ORGANISM: Artificial sequence
<220> FEATURE:
<223> OTHER INFORMATION: plasmid pSP-B5

<400> SEQUENCE: 35

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020

ccggtgtggg tttagatgac aagggagacg cattgggtca acagtataga accgtggatg   1080

atgtggtctc tacaggatct gacattatta ttgttggaag aggactattt gcaaagggaa   1140

gggatgctaa ggtagagggt gaacgttaca gaaaagcagg ctgggaagca tatttgagaa   1200

gatgcggcca gcaaaactaa aaaactgtat tataagtaaa tgcatgtata ctaaactcac   1260

aaattagagc ttcaatttaa ttatatcagt tattacccta tgcggtgtga aataccgcac   1320

agatgcgtaa ggagaaaata ccgcatcagg aaattgtaaa cgttaatatt ttgttaaaat   1380

tcgcgttaaa tttttgttaa atcagctcat tttttaacca ataggccgaa atcggcaaaa   1440

tcccttataa atcaaaagaa tagaccgaga tagggttgag tgttgttcca gtttggaaca   1500

agagtccact attaaagaac gtggactcca acgtcaaagg gcgaaaaacc gtctatcagg   1560

gcgatggccc actacgtgaa ccatcaccct aatcaagttt tttggggtcg aggtgccgta   1620

aagcactaaa tcggaaccct aaagggagcc cccgatttag agcttgacgg ggaaagccgg   1680

cgaacgtggc gagaaaggaa gggaagaaag cgaaaggagc gggcgctagg gcgctggcaa   1740

gtgtagcggt cacgctgcgc gtaaccacca cacccgccgc gcttaatgcg ccgctacagg   1800

gcgcgtccat tcgccattca ggctgcgcaa ctgttgggaa gggcgatcgg tgcgggcctc   1860
```

```
ttcgctatta cgccagctgg ataaaggcgc gccaaacgac ctaggaattg gagcgacctc   1920
atgctatacc tgagaaagca acctgaccta caggaaagag ttactcaaga ataagaattt   1980
tcgttttaaa acctaagagt cactttaaaa tttgtataca cttatttttt ttataactta   2040
tttaataata aaaatcataa atcataagaa attcgcttat ttagaagtgt caacaacgta   2100
tctaccaacg atttgaccct tttccatctt ttcgtaaatt tctggcaagg tagacaagcc   2160
gacaaccttg attggagact tgaccaaacc tctggcgaag aattgttaat taagagctca   2220
gatcttatcg tcgtcatcct tgtaatccat cgatactagt gcggccgctt gttttatatt   2280
tgttgtaaaa agtagataat tacttccttg atgatctgta aaaaagagaa aaagaaagca   2340
tctaagaact tgaaaaacta cgaattagaa aagaccaaat atgtatttct tgcattgacc   2400
aatttatgca agtttatata tatgtaaatg taagtttcac gaggttctac taaactaaac   2460
cacccccttg gttagaagaa aagagtgtgt gagaacaggc tgttgttgtc acacgattcg   2520
gacaattctg tttgaaagag agagagtaac agtacgatcg aacgaacttt gctctggaga   2580
tcacagtggg catcatagca tgtggtacta aaccctttcc cgccattcca gaaccttcga   2640
ttgcttgtta caaaacctgt gagccgtcgc taggaccttg ttgtgtgacg aaattggaag   2700
ctgcaatcaa taggaagaca ggaagtcgag cgtgtctggg ttttttcagt tttgttcttt   2760
ttgcaaacaa atcacgagcg acggtaattt ctttctcgat aagaggccac gtgctttatg   2820
agggtaacat caattcaaga aggagggaaa cacttccttt ttctggccct gataatagta   2880
tgagggtgaa gccaaaataa aggattcgcg cccaaatcgg catctttaaa tgcaggtatg   2940
cgatagttcc tcactctttc cttactcacg agtaattctt gcaaatgcct attatgcaga   3000
tgttataata tctgtgcgtc ttgagttgaa gtcaggaatc taaaataaaa attaaggtta   3060
ataaaaagag gaaagaaaaa aaaattaatc gatttacaga aacttgcaca ctaaaaatac   3120
acaactaaaa gcaattacag tatgggaagt catcgacgtt atctctacta tagtatatta   3180
tcatttctat tattatcctg ctcagtggta cttgcaaaac aagataagac cccattcttt   3240
gaaggtactt ccaggccggc cgcacacacc atagcttcaa aatgtttcta ctcctttttt   3300
actcttccag attttctcgg actccgcgca tcgccgtacc acttcaaaac acccaagcac   3360
agcatactaa atttcccctc tttcttcctc tagggtgtcg ttaattaccc gtactaaagg   3420
tttggaaaag aaaaaagaga ccgcctcgtt tctttttctt cgtcgaaaaa ggcaataaaa   3480
atttttatca cgtttctttt tcttgaaaat ttttttttt gatttttttc tctttcgatg   3540
acctcccatt gatatttaag ttaataaacg gtcttcaatt tctcaagttt cagtttcatt   3600
tttcttgttc tattacaact ttttttactt cttgctcatt agaaagaaag catagcaatc   3660
taatctaagt tttaattaca aggatcccgc tcgagatgag attactgacc gctgtcgatc   3720
aactctttct attgttggag agtagaaagc acccaatgca cgttggtgga ctgttcctat   3780
tcgagcttcc agagaatgct gacattagtt tcgttcacca gcttgttaag caaatgcaag   3840
attccgacgt accaccaaca ttcccattca atcaggttct ggaacacatg atgttttgga   3900
aggaggacaa aaactttgac gtagaacatc atctacacca tgtggcttta ccaaaacctg   3960
ccagagttag agaattactc atgtacgttt ccagggaaca tgggaggttg ctcgatagag   4020
caatgccact atgggagtgc catgtgatcg aaggtattca accagagact gaaggttctc   4080
cagagagatt cgcattgtat ttcaagattc atcattcctt agtcgatggt atcgccgcta   4140
tgaggttggt gaaaaagtca ttatcacagt caccaaacga accagttacc cttccaatct   4200
```

```
ggtctttgat ggctcaccat agaaaccaaa tcgatgccat cttcccaaag gaaagatcag   4260
ccttgcgtat cttaaaggaa caagtttcta caatcaagcc tgtgtttact gaactcttga   4320
ataacttcaa aaactacaat gacgatagtt acgtcagcac ttttgacgct cctagatcaa   4380
tccttaaccg tagaatttct gcctcaagac gtattgcagc gcagtcatac gatatcaaaa   4440
gattcaatga catagcggag agaatcaaca tttccaaaaa cgatgtggtt ttggcagtat   4500
gttccggtgc tattagaaga taccttatct ctatggatgc tttaccatca aaacctctga   4560
tagcattcgt tcctatgtct ttgcgaactg atgatagtat agctggaaac caattgagtt   4620
ttgtactagc gaatctgggc acacatttgg atgatccatt atctagaatc aagctcattc   4680
atcgtagcat gaacaactct aagagaagat tcagaaggat gaaccaagca caagttatca   4740
attactccat agtatcttac gcatgggaag gcattaactt ggccactgat cttttcccta   4800
aaaagcaagc ctttaactta atcatctcta acgtcccagg ctcagaaaaa cctttgtatt   4860
ggaatggtgc aagattagaa tcactatatc ctgcttcaat cgtgtttaac ggacaagcta   4920
tgaatatcac gcttgcatct tacttggaca agatggaatt cggtataact gcttgttcta   4980
aagctctacc tcatgtccaa gatatgttga tgcttattga ggaagagcta caactgctgg   5040
aatctgttag caaggaacta gaattcaatg ggattacagt aaaagataag tcagagaaaa   5100
agctgaaaaa gttggcccct taacccaagc ttggtaccgc ggctagctaa gatccgctct   5160
aaccgaaaag gaaggagtta gacaacctga agtctaggtc cctatttatt tttttatagt   5220
tatgttagta ttaagaacgt tatttatatt tcaaattttt cttttttttc tgtacagacg   5280
cgtgtacgca tgtaacatta tactgaaaac cttgcttgag aaggttttgg gacgctcgaa   5340
gatcctccgg atcgtttcgc cggcgtttat ccagctgcat taatgaatcg gccaacgcgc   5400
ggggagaggc ggtttgcgta ttgggcgctc ttccgcttcc tcgctcactg actcgctgcg   5460
ctcggtcgtt cggctgcggc gagcggtatc agctcactca aaggcggtaa tacggttatc   5520
cacagaatca ggggataacg caggaaagaa catgtgagca aaaggccagc aaaaggccag   5580
gaaccgtaaa aaggccgcgt tgctggcgtt tttccatagg ctccgccccc ctgacgagca   5640
tcacaaaaat cgacgctcaa gtcagaggtg gcgaaacccg acaggactat aaagatacca   5700
ggcgtttccc cctggaagct ccctcgtgcg ctctcctgtt ccgaccctgc cgcttaccgg   5760
atacctgtcc gcctttctcc cttcgggaag cgtggcgctt tctcatagct cacgctgtag   5820
gtatctcagt tcggtgtagg tcgttcgctc caagctgggc tgtgtgcacg aaccccccgt   5880
tcagcccgac cgctgcgcct tatccggtaa ctatcgtctt gagtccaacc cggtaagaca   5940
cgacttatcg ccactggcag cagccactgg taacaggatt agcagagcga ggtatgtagg   6000
cggtgctaca gagttcttga agtggtggcc taactacggc tacactagaa ggacagtatt   6060
tggtatctgc gctctgctga agccagttac cttcggaaaa agagttggta gctcttgatc   6120
cggcaaacaa accaccgctg gtagcggtgg tttttttgtt tgcaagcagc agattacgcg   6180
cagaaaaaaa ggatctcaag aagatccttt gatcttttct acggggtctg acgctcagtg   6240
gaacgaaaac tcacgttaag ggattttggt catgagatta tcaaaaagga tcttcaccta   6300
gatcctttta aattaaaaat gaagttttaa atcaatctaa agtatatatg agtaaacttg   6360
gtctgacagt taccaatgct taatcagtga ggcacctatc tcagcgatct gtctatttcg   6420
ttcatccata gttgcctgac tccccgtcgt gtagataact acgatacggg agggcttacc   6480
atctggcccc agtgctgcaa tgataccgcg agacccacgc tcaccggctc cagatttatc   6540
agcaataaac cagccagccg gaagggccga gcgcagaagt ggtcctgcaa ctttatccgc   6600
```

```
ctccatccag tctattaatt gttgccggga agctagagta agtagttcgc cagttaatag   6660

tttgcgcaac gttgttgcca ttgctacagg catcgtggtg tcacgctcgt cgtttggtat   6720

ggcttcattc agctccggtt cccaacgatc aaggcgagtt acatgatccc ccatgttgtg   6780

caaaaaagcg gttagctcct tcggtcctcc gatcgttgtc agaagtaagt tggccgcagt   6840

gttatcactc atggttatgg cagcactgca taattctctt actgtcatgc catccgtaag   6900

atgcttttct gtgactggtg agtactcaac caagtcattc tgagaatagt gtatgcggcg   6960

accgagttgc tcttgcccgg cgtcaatacg ggataatacc gcgccacata gcagaacttt   7020

aaaagtgctc atcattggaa aacgttcttc ggggcgaaaa ctctcaagga tcttaccgct   7080

gttgagatcc agttcgatgt aacccactcg tgcacccaac tgatcttcag catcttttac   7140

tttcaccagc gtttctgggt gagcaaaaac aggaaggcaa aatgccgcaa aaaagggaat   7200

aagggcgaca cggaaatgtt gaatactcat actcttcctt tttcaatatt attgaagcat   7260

ttatcagggt tattgtctca tgagcggata catatttgaa tgtatttaga aaaataaaca   7320

aataggggtt ccgcgcacat ttccccgaaa agtgccacct gaacgaagca tctgtgcttc   7380

attttgtaga acaaaaatgc aacgcgagag cgctaatttt tcaaacaaag aatctgagct   7440

gcatttttac agaacagaaa tgcaacgcga aagcgctatt ttaccaacga agaatctgtg   7500

cttcattttt gtaaaacaaa aatgcaacgc gagagcgcta atttttcaaa caaagaatct   7560

gagctgcatt tttacagaac agaaatgcaa cgcgagagcg ctattttacc aacaaagaat   7620

ctatacttct tttttgttct acaaaaatgc atcccgagag cgctattttt ctaacaaagc   7680

atcttagatt actttttttc tcctttgtgc gctctataat gcagtctctt gataactttt   7740

tgcactgtag gtccgttaag gttagaagaa ggctactttg gtgtctattt tctcttccat   7800

aaaaaaagcc tgactccact tcccgcgttt actgattact agcgaagctg cgggtgcatt   7860

ttttcaagat aaaggcatcc ccgattatat tctataccga tgtggattgc gcatactttg   7920

tgaacagaaa gtgatagcgt tgatgattct tcattggtca gaaaattatg aacggtttct   7980

tctattttgt ctctatatac tacgtatagg aaatgtttac attttcgtat tgttttcgat   8040

tcactctatg aatagttctt actacaattt ttttgtctaa agagtaatac tagagataaa   8100

cataaaaaat gtagaggtcg agtttagatg caagttcaag gagcgaaagg tggatgggta   8160

ggttatatag ggatatagca cagagatata tagcaaagag atacttttga gcaatgtttg   8220

tggaagcggt attcgcaata ttttagtagc tcgttacagt ccggtgcgtt tttggttttt   8280

tgaaagtgcg tcttcagagc gcttttggtt ttcaaaagcg ctctgaagtt cctatacttt   8340

ctagagaata ggaacttcgg aataggaact tcaaagcgtt tccgaaaacg agcgcttccg   8400

aaaatgcaac gcgagctgcg cacatacagc tcactgttca cgtcgcacct atatctgcgt   8460

gttgcctgta tatatatata catgagaaga acggcatagt gcgtgtttat gcttaaatgc   8520

gtacttatat gcgtctattt atgtaggatg aaaggtagtc tagtacctcc tgtgatatta   8580

tcccattcca tgcggggtat cgtatgcttc cttcagcact accctttagc tgttctatat   8640

gctgccactc ctcaattgga ttagtctcat ccttcaatgc tatcatttcc tttgatattg   8700

gatcatacta agaaaccatt attatcatga cattaaccta taaaaatagg cgtatcacga   8760

ggccctttcg tc                                                       8772
```

UNITED STATES PATENT AND TRADEMARK OFFICE
CERTIFICATE OF CORRECTION

PATENT NO. : 11,162,119 B2  
APPLICATION NO. : 16/719399  
DATED : November 2, 2021  
INVENTOR(S) : Nielsen et al.

It is certified that error appears in the above-identified patent and that said Letters Patent is hereby corrected as shown below:

In the Specification

Column 6, Line 33: Delete "1-oxidation" and insert -- β-oxidation --

Column 14, Line 18: Delete "Seri 157Ala" and insert -- Ser1157Ala --

Column 17, Line 58: Delete "DH5a" and insert -- DH5α --

Column 18, Line 9: Delete "pSP-81" and insert -- pSP-B1 --

Column 22, Line 6: Delete "DH5a" and insert -- DH5α --

Signed and Sealed this  
Twenty-eighth Day of June, 2022

Katherine Kelly Vidal  
*Director of the United States Patent and Trademark Office*